United States Patent [19]
Nagel

[11] Patent Number: 5,618,808
[45] Date of Patent: Apr. 8, 1997

[54] BENZOTHIAZEPINE AND BENZOXAZEPINE DERIVATIVES AS CHOLECYSTOKININ RECEPTOR ANTAGONISTS

[75] Inventor: Arthur A. Nagel, Gales Ferry, Conn.

[73] Assignee: Pfizer, Inc., New York, N.Y.

[21] Appl. No.: 360,843

[22] PCT Filed: Apr. 14, 1993

[86] PCT No.: PCT/US93/03389
§ 371 Date: Dec. 21, 1994
§ 102(e) Date: Dec. 21, 1994

[87] PCT Pub. No.: WO94/01421
PCT Pub. Date: Jan. 20, 1994

[51] Int. Cl.⁶ .................. C07D 267/02; C07D 281/02; A61K 31/55
[52] U.S. Cl. .................. 514/211; 514/491
[58] Field of Search .............. 540/491; 514/211

[56] References Cited

U.S. PATENT DOCUMENTS

| | | | |
|---|---|---|---|
| 4,477,464 | 10/1984 | Slade et al. | 424/275 |
| 4,564,612 | 1/1986 | Sugihara et al. | 514/211 |
| 5,055,464 | 10/1991 | Murakami et al. | 514/211 |

OTHER PUBLICATIONS

Maurice, T. et al. *J. Pharmacol. Exp. Ther.* 269(2), 665 (1994), Abstract From MEDLINE.
Sugaya, K. et al. *Jpn. J. Pharmacol.* 59(1), 125 (1992), Abstract From MEDLINE.
Yamamoto, Y. et al. *Brain Res.* 630(1–2), 353 (1993), Abstract From MEDLINE.
Piolti, R. et al. *Neurology* 41(5), 749(1991), Abstract From MEDLINE.
Goldner, F.H. et al. *Internal Medicine*, ed. by Stein, J.H. et al. (Mosby, St. Louis), p. 459 (1994).

*Primary Examiner*—Mukund J. Shah
*Assistant Examiner*—King Lit Wong
*Attorney, Agent, or Firm*—Peter C. Richardson; Paul H. Ginsburg; Grover F. Fuller, Jr.

[57] ABSTRACT

The present invention relates to novel substituted benzothiazepines and benzoxazepines of the formula

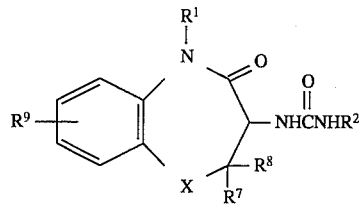

wherein $R^1$, $R^2$, $R^7$, $R^8$, $R^9$ and X are as defined below, and to novel intermediates used in the synthesis of such compounds.

Such compounds are useful in the treatment and prevention of gastrointestinal disorders, pain and anxiety disorders.

10 Claims, No Drawings

BENZOTHIAZEPINE AND BENZOXAZEPINE DERIVATIVES AS CHOLECYSTOKININ RECEPTOR ANTAGONISTS

BACKGROUND OF THE INVENTION

This is a 371 of PCT/US93/03389 filed Apr. 14, 1993.

The present invention relates to novel substituted benzothiazepines and benzoxazepines, pharmaceutical compositions comprising such compounds and the use of such compounds in the treatment and prevention of central nervous system and gastrointestinal disorders. The pharmaceutically active compounds of this invention are cholecystokinin (CCK) receptor antagonists.

Cholecystokinin (CCK) is a 33-amino acid peptide originally discovered and characterized in 1971. (See Mutt et al., *Biochem. J.*, 125, 57 (1971)). It carries out its biological responses by binding to its two receptor types: CCK-A and CCK-B. The CCK-A receptor is located primarily in the gallbladder and pancreas, and mediates CCK-induced enzyme secretion and gallbladder contraction during a meal. The CCK-B receptor is located in the stomach, where it is involved in acid secretion, and in the brain, where it mediates pain and anxiety responses.

A number of potent and selective non-peptide antagonists for these two receptors are known (See M. G. Bock, *Drugs of the Future*, 16(7), 631–640 (1991) and R. M. Freidinger, *Med. Res. Rev.*, 9, 271–290 (1989)). Merck's L-364,718 (devazepide) is a selective CCK-A antagonist. (See O'Neill et al., *Brain Res.*, 534, 287–290 (1990)). Merck's benzodiazepine L-365,260 is a selective CCK-B antagonist that was found to have an analgesic effect on squirrel monkeys. (See O'Neill et al., *Brain Res.*, 534, 287–290 (1990)). Parke-Davis' CI-988 is a selective CCK-B antagonist that was found to reverse the pentagastrin-induced anxiogenic response in rats. (See Singh et al., *Proc. Nat'l. Acad. Sci., U.S.*, 88, 1130–33 (1991)). U.S. patent application 825,677, filed Jan. 27, 1992, refers to substituted hexahydroazepinones and tetrahydrobenzazepinones that are selective CCK-B receptor antagonists.

SUMMARY OF THE INVENTION

The present invention relates to compounds of the formula

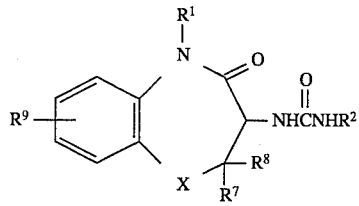

I wherein

X is oxygen, sulfur, sulfoxide or sulfone;

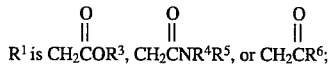

$R^1$ is $CH_2COR^3$, $CH_2CNR^4R^5$, or $CH_2CR^6$;

$R^2$ is phenyl optionally substituted with one or more substituents, preferably one or two substituents, independently selected from $(C_1-C_6)$alkyl, nitro, amino, $(C_1-C_6)$alkylamino, di-$(C_1-C_6)$alkylamino, halo, hydroxy, $CO_2H$, $CO_2(C_1-C_6)$alkyl, tetrazolyl, $SO_3H$, $SO_2NH_2$, $SO_2NH(C_1-C_6)$alkylamino, $SO_2N$-di-$(C_1-C_6)$alkylamino and a group of the formula

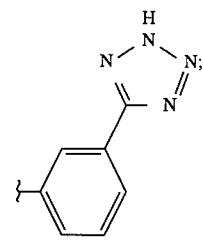

$R^3$ and $R^5$ are independently selected from $(C_1-C_6)$alkyl, 1-adamantyl and 2-adamantyl;

$R^4$ is hydrogen or $(C_1-C_6)$alkyl;

$R^6$ is a six membered saturated heterocyclic ring containing 5 carbon atoms and one nitrogen atom, wherein the nitrogen atom is the point of attachment, one of the carbon atoms may optionally be replaced by an oxygen or nitrogen atom, and one or more of said carbon atoms may optionally be substituted with one or two substituents independently selected from cyano and $(C_1-C_6)$alkyl;

$R^7$ is hydrogen or methyl;

$R^8$ is hydrogen or methyl; and $R^9$ is hydrogen, halo, phenyl or $(C_1-C_6)$alkyl.

Examples of possible $R^6$ groups are the groups having the formula

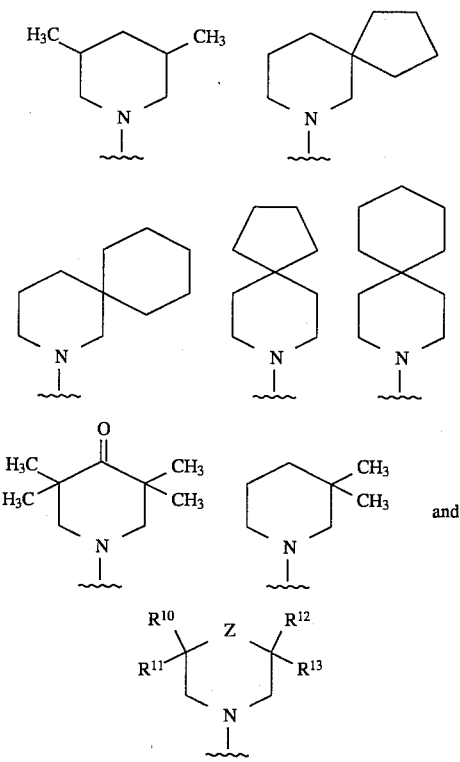

wherein Z is NH or $CH_2$ and $R^{10}$, $R^{11}$, $R^{12}$ and $R^{13}$ are independently selected from hydrogen and $(C_1-C_3)$alkyl.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The term "alkyl", as used herein, unless otherwise indicated, includes saturated monovalent hydrocarbon radicals having straight, branched or cyclic moieties or combinations thereof.

The term "halo", as used herein, unless otherwise indicated, includes chloro, fluoro, bromo and iodo.

Preferred compounds of the formula I include those wherein X is oxygen.

Preferred compounds of the formula I also include those wherein $R^1$ is

and $R^6$ is a group of the formula

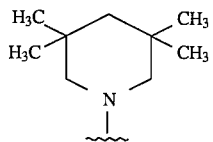

Preferred compounds of the formula I also include those having the absolute stereochemistry depicted below

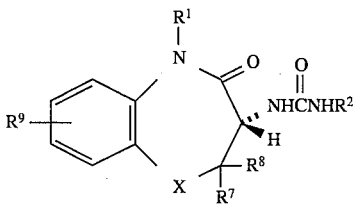

and wherein $R^2$ is as defined above.

Using the Cahn-Ingold-Prelog convention, preferred compounds of the formula I wherein X is sulfur include those having the "S" configuration at the carbon adjacent to the oxo substituent, and preferred compounds of the formula I wherein X is oxygen include those having the "R" configuration at the carbon adjacent to the oxo substituent.

Specific preferred compounds of the formula I include the following:

3(S)-1-[3,4-dihydro-4-oxo-3-[[(3-methylphenylamino)carbonyl]amino]-1,5-benzothiazepin-5(2H)-acetyl]-3,3-dimethyl piperidine;

3(S)-1-[3,4-dihydro-4-oxo-3-[[(3-methylphenylamino)carbonyl]amino]-1,5-benzothiazepin-5(2H)-acetyl]-4,4-tetramethylene piperidine;

3(S)-1-[3,4-dihydro-4-oxo-3-[[(3-methoxyphenylamino)carbonyl]amino]-1,5-benzothiazepin-5(2H)-acetyl]-3,3-dimethyl piperidine;

7(R)-1-{9-[2-(3,3,5,5-tetramethylpiperidin-1-yl)-2-oxoethyl]-8-oxo-6,7,8,9-tetrahydro-5-oxa-9-aza-benzocyclohepten-7-yl}-3-m-chlorophenyl-urea;

7(R)-1-{9-[2-(3,3,5,5-tetramethylpiperidin-1-yl)-2-oxoethyl]-8-oxo-6,7,8,9-tetrahydro-5-oxa-9-aza-benzocyclohepten-7-yl}-3-m-tolyl-urea;

7(R)-(3-dimethylamino-phenyl)-3-{8-oxo-9-[2-oxo-2(3,3,5,5-tetramethylpiperidin-1-yl)-ethyl-6,7,8,9-tetrahydro-5-oxa-9-aza-benzocyclohepten-7-yl}-urea;

7(R)-1-{9-[2-(3,3-dimethylpiperidin-1-yl)-2-oxo-ethyl]-3-fluoro-8-oxo-6,7,8,9-tetrahydro-5-oxa-9-aza-benzocyclohepten-7-yl}-3-m-tolyl-urea;

7(R)-1-{9-[2-(3,3,5,5-tetramethylpiperidin-1-yl)-2-oxo-ethyl]-3-fluoro-8oxo-6,7,8,9-tetrahydro-5-oxa-9-aza-benzocyclohepten-7-yl}-3-m-tolyl-urea;

6(S),7(R)-1{9-[2-(3,3,5,5-tetramethylpiperidin-1-yl)-2-oxo-ethyl]-6-methyl-8-oxo-6,7,8,9-tetrahydro-5-oxa-9-aza-benzocyclohepten-7-yl}-3-m-tolyl-urea;

6(S),7(R)-1-(3-dimethylamino-phenyl)-3-{6-methyl-8-oxo-9-[2-oxo-2-(3,3,-dimethylpiperidin-1-yl)-ethyl-6,7,8,9-tetrahydro-5-oxa-9-aza-benzocyclohepten-7-yl-urea;

6(S),7(R)-1-(3-dimethylamino-phenyl)-3-{6-methyl-8-oxo-9-[2-oxo-2-(3,3,5,5-tetramethylpiperidin-1-yl)-ethyl-6,7,8,9-tetrahydro-5-oxa-9-aza-benzocyclohepten-7-yl-urea;

6(S),7(R)-1{9-[2-(3,3-dimethylpiperidin-1-yl)-2-oxo-ethyl]-6-methyl-8-oxo-6,7,8,9-tetrahydro-5-oxa-9-aza-benzocyclohepten-7-yl}-3-m-chlorophenyl-urea;

6(S),7(R)-1{9-[2-(3,3,5,5-tetramethylpiperidin-1-yl)-2-oxo-ethyl]-6-methyl-8-oxo-6,7,8,9-tetrahydro-5-oxa-9-aza-benzocyclohepten-7-yl}-3-m-chlorophenyl-urea;

6(S),7(R)-1{9-[2-(3,3,5,5-tetramethylpiperidin-1-yl)-2-oxo-ethyl]-3-fluoro-6-methyl-8-oxo-6,7,8,9-tetrahydro-5-oxa-9-aza-benzocyclohepten-7-yl}-3-m-tolyl-urea; and 3(S)-1-[3,4-dihydro-4-oxo-3-[[(3-chlorophenylamino)carbonyl]amino]-1,5-benzothiazephin-5(2H)-acetyl]-3,3-dimethyl piperidine-1,1-dioxide.

Other examples of compounds of the formula I include the following:

7(S)-1-{9-[2-(3,3-dimethyl-4-oxo-piperidin-1-yl)-2-oxo-ethyl]-8-oxo-6,7,8, 9,-tetrahydro-5-oxo-9-azabicyclohepten-7-yl}-3-m-tolyl-urea;

7(S)-1-{9-[2-(3,5-dimethyl-piperidin-1-yl)-2-oxo-ethyl]-8-oxo-6,7,8,9-tetrahydro-5-oxo-9-aza-benzocyclohepten-7-yl}-3-m-tolyl-urea;

(R,S)-1-[3,4-dihydro-4-oxo-3-[[(3-methylphenylamino)carbonyl]amino]-1,5-benzothiazepin-5(2H)-acetyl]-3,3-pentamethylene piperidine;

(R,S)-1-[3,4-dihydro-4-oxo-3-[[(3-methoxyphenylamino)carbonyl]amino]-1,5-benzothiazepin-5(2H)-acetyl]-2-methyl piperidine;

(R,S)-1-[3,4-dihydro-4-oxo-3-[[(3-methoxyphenylamino)carbonyl]amino]-1,5-benzothiazepin-5(2H)-acetyl]-4,4-tetramethylene piperidine;

3(S)-2-[4-oxo-3-(3-m-tolyl-ureido)-3,4-dihydro-2H-benzo[b]-[1,4]-thiazepin-5-yl]-N-thiochroman-4-yl-acetamide;

7(S)-1-{9-[2-(3,5-dimethylpiperidin-1-yl)-2-oxo-ethyl]-8-oxo-6,7,8,9-tetrahydro-5-oxo-9-aza-benzocyclohepten-7-yl}-3-m-tolyl-urea;

7(R)-1-{9-[2-(3,3-dimethylpiperidin-1-yl)-2-oxo-ethyl]-8-oxo-6,7,8,9-tetrahydro-5-oxa-9-aza-benzocyclohepten-7-yl}-3-m-methoxyphenyl-urea;

7(R)-1-{9-[2-(7-aza-spiro[4.5]dec-7-yl)-2-oxo-ethyl]-8-oxo-6,7,8,9-tetrahydro-5-oxa-9-aza-benzocyclohepten-7-yl}-3-m-methoxyphenyl-urea;

7(R)-1-{9-[2-(3,3-dimethylpiperidin-yl)-2-oxo-ethyl]-8-oxo-6,7,8,9-tetrahydro-5-oxa-9-aza-benzocyclohepten-7-yl}-3-m-ethylphenyl-urea;

7(R)-1-(3-chloro-phenyl)-3-{8-oxo-9-[2-oxo-2-(3,3,5,5-tetramethyl-4-oxo-piperidin-1-yl)-ethyl]-6,7,8,9-tetrahydro-5-oxa-8-aza-benzocyclohepten-7-yl}-urea;

(S)-1-[3,4-dihydro-4-oxo-3-[[(3-chlorophenylamino)carbonyl]amino]-1,5-benzothiazepin-5(2H)-acetyl]-3,3-dimethyl piperidine;

(R,S)-3,4-dihydro-4-oxo-3-[[(3-methylphenylamino)carbonyl]amino]-1,5-benzothiazepine-5(2H)-acetic acid-1,1-dimethylethylester;

(R,S)-3,4-dihydro-4-oxo-3-[[(3-methylphenylamino)carbonyl]amino]-1,5-benzothiazepine-5(2H)-acetic acid-1,1-dimethylethyl ester, 1,1-dioxide;

(R,S)-1-[3,4-dihydro-4-oxo-3-[[(3-methylphenylamino)carbonyl]amino]-1,5-benzothiazepin-5(2H)-acetyl]-3,3-dimethylpiperidine-1,1-dioxide; and (S)-1-[3,4-dihydro-4-oxo-3-[[(3-methoxyphenylamino)carbonyl]amino]-1,5-benzothiazepin-5(2H)-acetyl]-3,3-dimethyl piperidine-1,1-dioxide.

This invention also relates to compounds of the formulae

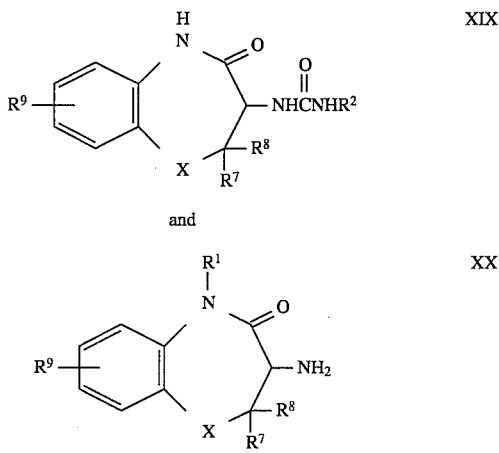

wherein X, $R^1$, $R^2$, $R^7$, $R^8$ and $R^9$ are defined as above. These compounds are useful as intermediates in the synthesis of compounds of the formula I.

Preferred compounds of the formulae XIX and XX include those wherein the substituents $R^1$, $R^2$, $R^7$, $R^8$ and $R^9$ are as defined above for the preferred compounds of formula I, and those having the preferred stereochemistry as defined above for compounds of the formula I.

Examples of compounds of the formula XIX are the following:

(S)-N-(3-methylphenyl)-N'-(2,3,4,5-tetrahydro-4-oxo-1,5-benzothiazepin-3-yl)-urea;

(S)-N-(3-methoxyphenyl)-N'-(2,3,4,5-tetrahydro-4-oxo-1,5-benzothiazepin-3-yl)-urea;

3(S)-N-(3-chlorophenyl)-N'-(2,3,4,5-tetrahydro-4-oxo-1,5-benzothiazepin-3-yl)-urea;

7(R)-1-(8-oxo-6,7,8,9-tetrahydro-5-oxa-9-aza-benzocyclohepten-7-yl)-3-m-tolyl-urea;

7(R)-1-(3-methoxy-phenyl)-3-(8-oxo-6,7,8,9-tetrahydro-5-oxa-9-aza-benzocyclohepten-7-yl)-urea;

7(R)-1-(3-chloro-phenyl)-3-(8-oxo-6,7,8,9-tetrahydro-5-oxa-9-aza-benzocyclohepten-7-yl)-urea;

7(R)-1-(3-dimethylamino-phenyl)-3-(8-oxo-6,7,8,9-tetrahydro-5-oxa-9-aza-benzocyclohepten-7-yl)-urea;

7(R)-1-(3-fluoro-8-oxo-6,7,8,9-tetrahydro-5-oxa-9-aza-benzocyclohepten-7-yl)-3-m-tolyl-urea;

7(R)-1-(3-chloro-phenyl)-3-(3-fluoro-8-oxo-6,7,8,9-tetrahydro-5-oxa-9-aza-benzocyclohepten-7-yl)-urea;

7(R)-1-(3-dimethylamino-phenyl)-3-(3-fluoro-8-oxo-6,7,8,9-tetrahydro-5-oxa-9-aza-benzocyclohepten-7-yl)-urea;

6(S),7(R)-1-(6-methyl-8-oxo-6,7,8,9-tetrahydro-5-oxa-9-aza-benzocyclohepten-7-yl)-3-m-tolyl-urea;

6(S),7(R)-1-(3-chloro-phenyl)-3-(6-methyl-8-oxo-6,7,8,9-tetrahydro-5-oxa-9-aza-benzocyclohepten-7-yl)-urea;

6(S),7(R)-1-(3-dimethylamino-phenyl)-3-(6-methyl-8-oxo-6,7,8,9-tetrahydro-5-oxa-9-aza-benzocyclohepten-7-yl)-urea;

6(S),7(R)-1-(3-fluoro-methyl-8-oxo-6,7,8,9-tetrahydro-5-oxa-9-aza-benzocyclohepten-7-yl)-3-m-tolyl-urea;

6(S),7(R)-1-(3-chloro-phenyl)-3-(3-fluoro-methyl-8-oxo-6,7,8,9-tetrahydro-5-oxa-9-aza-benzocyclohepten-7-yl)-urea; and 6(S),7(R)-1-(3-dimethylamino-phenyl)-3-(3-fluoro-6-methyl-8-oxo-6,7,8,9-tetrahydro-5-oxa-9-aza-benzocyclohepten-7-yl)-urea.

Examples of compounds of the formula XX are:

7(R)-amino-8-[2-oxo-2-(3,3-dimethyl-piperidin-1-yl)-ethyl]-6,7-dihydro-9H-5-oxa-9-aza-benzocyclohepten-8-one;

3(S)-amino-5-[2-oxo-2-(3,3-dimethyl-piperidin-1-yl)-ethyl]-3,4-dihydro-1,5-benzothiazepin-4-one;

7(R)-amino-8-[2-oxo-2-(3,3,5,5-tetramethyl-piperidin-1-yl)-ethyl]-6,7-dihydro-9H-5-oxa-9-aza-benzocyclohepten-8-one;

6(S),7(R)-6-methyl-7-amino-8-[2-oxo-2-(3,3,5,5-tetramethyl-piperidin-1-yl)-ethyl]-6,7-dihydro-9H-5-oxa-9-aza-benzocyclohepten-8-one;

7(R)-3-fluoro-7-amino-8-[2-oxo-2-(3,3,5,5-tetramethyl-piperidin-1-yl)-ethyl]-6,7-dihydro-9H-5-oxa-9-aza-benzocyclohepten-8-one; and 6(S),7(R)-3-fluoro-6-methyl-7-amino-8-[2-oxo-2-(3,3,5,5-tetramethyl-piperidin-1-yl)-ethyl]-6,7-dihydro-9H-5-oxa-9-aza-benzocyclohepten-8-one.

The present invention also relates to a pharmaceutical composition for treating or preventing a condition selected from the group consisting of pain, gastrointestinal disorders such as ulcer and colitis, and central nervous system disorders such as anxiety and panic disorder in a mammal, including a human, comprising an amount of a compound of the formula I, or a pharmaceutically acceptable salt thereof, effective in treating or preventing such condition, and a pharmaceutically acceptable carrier.

The present invention also relates to a method of treating or preventing a condition selected from the group consisting of pain, gastrointestinal disorders such as ulcer and colitis, and central nervous system disorders such as anxiety and panic disorder in a mammal, including a human, comprising administering to said mammal an amount of a compound of the formula I, or a pharmaceutically acceptable salt thereof, effective in treating or preventing such condition, The present invention also relates to a pharmaceutical composition for antagonizing the effects of cholecystokinin in a mammal, including a human, comprising a cholecystokinin antagonizing amount of a compound of the formula I, or a pharmaceutically acceptable salt thereof, and a pharmaceutically acceptable carrier.

The present invention also relates to a method of antagonizing the effects of cholecystokinin in a mammal, including a human, comprising administering to said mammal a cholecystokinin antagonizing amount of a compound of the formula I, or a pharmaceutically acceptable salt thereof.

The present invention also relates to a pharmaceutical composition for treating or preventing a cholecystokinin mediated disorder in a mammal, including a human, comprising a cholecystokinin antagonizing amount of a compound of the formula I, or a pharmaceutically acceptable salt thereof, and a pharmaceutically acceptable carrier.

The present invention also relates to a method of treating or preventing a cholecystokinin mediated disorder in a mammal, including a human, comprising administering to said mammal a cholecystokinin antagonizing amount of a compound of the formula I, or a pharmaceutically acceptable salt thereof.

The present invention also relates to a pharmaceutical composition for treating or preventing a condition selected from the group consisting of pain, gastrointestinal disorders such as ulcer and colitis, and central nervous system disorders such as anxiety and panic disorder in a mammal, including a human, comprising an amount of a compound of the formula I, or a pharmaceutically acceptable salt thereof, effective in antagonizing the effect of cholecystokinin at its receptor site, and a pharmaceutically acceptable carrier.

The present invention also relates to a method of treating or preventing a condition selected from the group consisting of pain, gastrointestinal disorders such as ulcer and colitis, and central nervous system disorders such as anxiety and panic disorder in a mammal, including a human, comprising administering to said mammal an amount of a compound of the formula I, or a pharmaceutically acceptable salt thereof, effective in antagonizing the effect of cholecystokinin at its receptor site.

The compounds of the formulae I and VII have chiral centers and therefore exist in different enantiomeric and diastereomic forms. This invention relates to all optical isomers and all stereoisomers of compounds of the formulae I and VII, and mixtures thereof.

Formula I and formula VII above include compounds identical to those depicted but for the fact that one or more hydrogen or carbon atoms are replaced by isotopes thereof. Such compounds are useful as research and diagnostic tools in metabolism pharmacokinetic studies and in binding assays.

DETAILED DESCRIPTION OF THE INVENTION

The compounds of the formulae I and II may be prepared as described in the following reaction schemes and discussion. Unless otherwise indicated, $R^1$, $R^2$, $R^3$, $R^4$, $R^5$, $R^6$, and X in the reaction schemes and discussion that follow are defined as above.

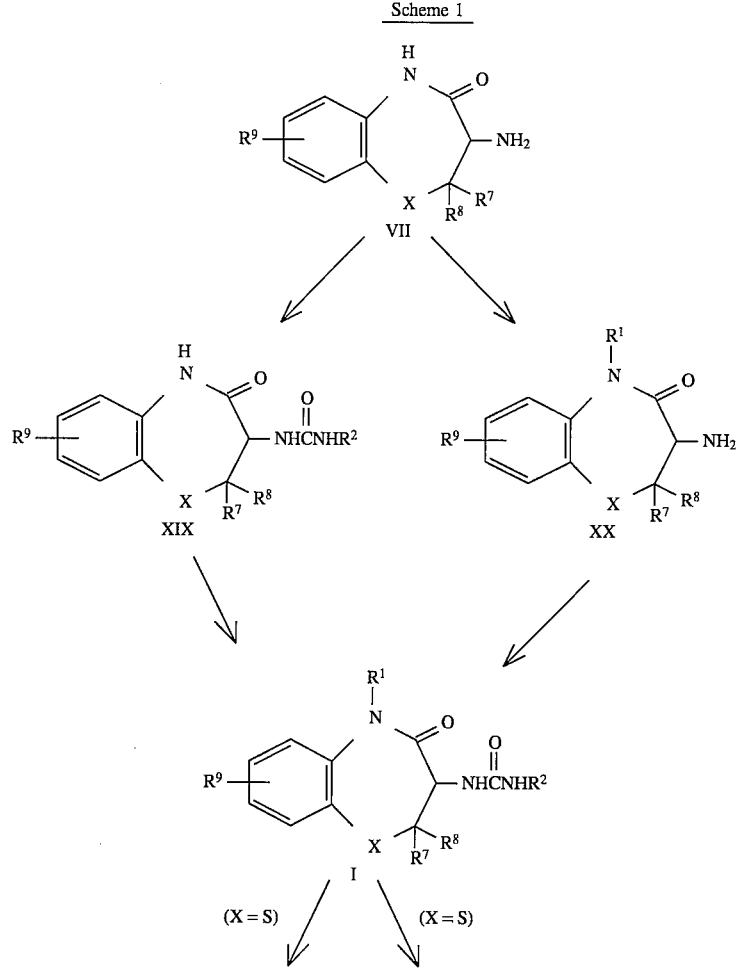

-continued
Scheme 1
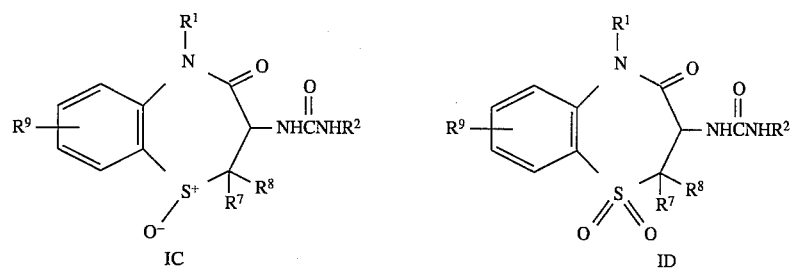
Scheme 2
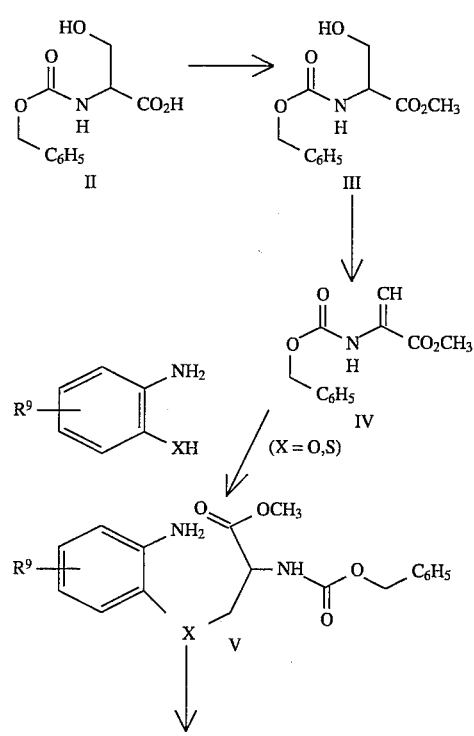
-continued
Scheme 2
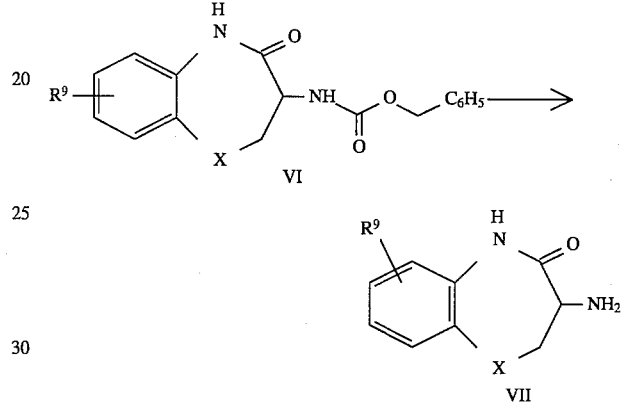
Scheme 3
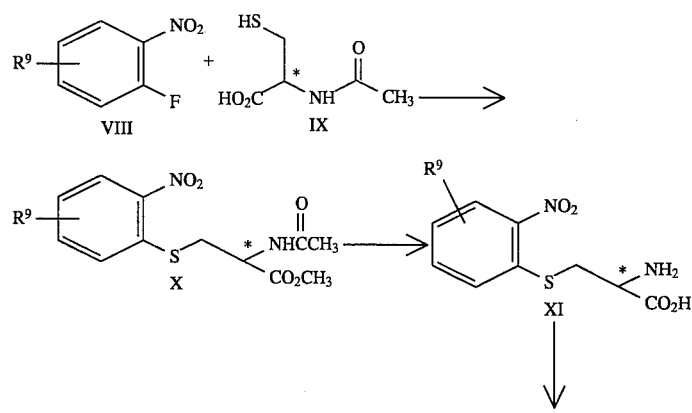

-continued
Scheme 3

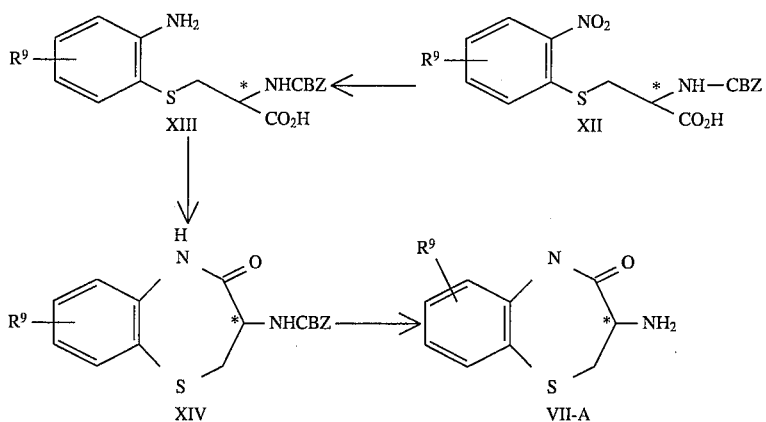

Scheme 4

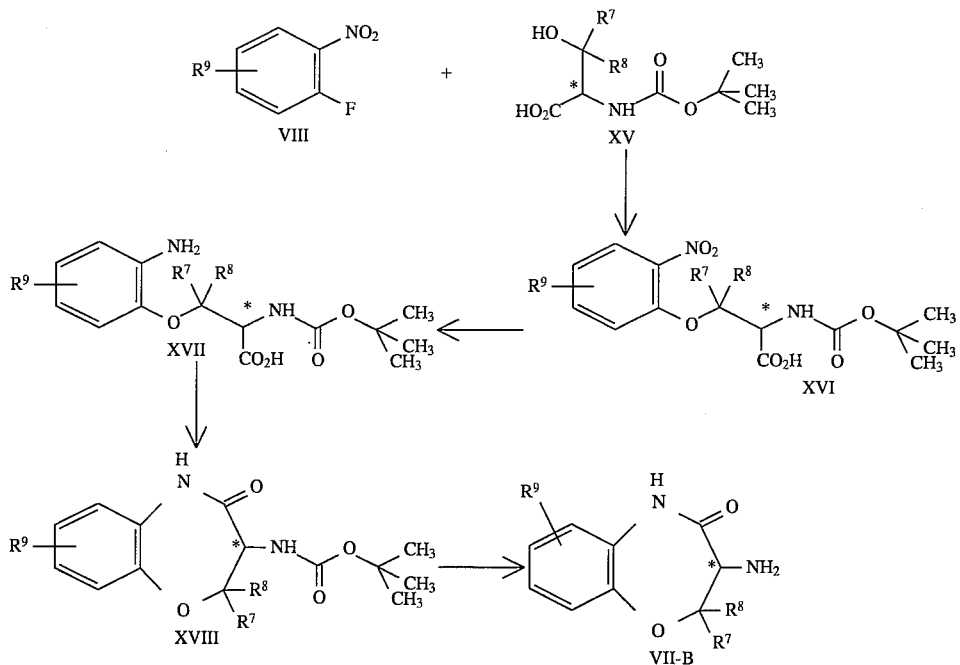

Scheme 1 illustrates the preparation of the pharmaceutically active compounds of the formula I and the intermediate compounds of the formulae XIX and XX from starting materials of the formula VII. The method illustrated in scheme 1 preserves the stereochemical configuration of the carbon adjacent to the oxo substituent in compounds of the formula VII, and therefore can be used to prepare any racemic compound or stereoisomer of the formula I from the appropriate starting material having the same configuration.

Referring to scheme 1, compounds of the formula I may be prepared by adding the $R^2$ containing sidechain to the starting material and then adding the $R^1$ substituent, or, alternatively, performing the two foregoing steps in the opposite order. If the $R^2$ containing sidechain is added first, the compounds are prepared in the following manner.

A compound of the formula VII is reacted with an isocyanate of the formula $R^2NCO$. This reaction is generally carried out at a temperature from about −78° C. to about 50° C., preferably at about 0° C., in an aprotic solvent such as methylene chloride, ethyl acetate, chloroform or ether, preferably in methylene chloride. It yields a compound of the formula XIX. The compound of formula XIX is then reacted with a compound having the formula $R^1I$ in the presence of a strong base to produce the desired compound of formula I wherein X is either oxygen or sulfur. This reaction is typically conducted at a temperature from about −78° C. to about 0° C., preferably at about −78° C., in an anhydrous, aprotic solvent such as dimethylformamide (DMF), tetrahydrofuran (THF), ether or dimethylsulfoxide (DMSO), preferably in THF. Preferably, the reactant of formula $R^1I$ is added to the reaction mixture at about −78 ° C., after which the mixture is warmed to room temperature and stirred for about two hours. Suitable strong bases include sodium hydride, potassium hydride, lithium bis(trimethylsilyl)a- mide and lithium diisopropylamide. Lithium bis(trimethylsilyl)amide is preferred.

As indicated above, the two foregoing reaction steps may be performed in the opposite order. This reverse reaction sequence is depicted in scheme 1 as sequence VII→XX→I.

Compounds of the formula I wherein X is sulfur may be converted into the corresponding compounds of the formula I wherein X is sulfoxide by reacting them with sodium periodate or metachloroperbenzoic acid. When sodium periodate is used, the reaction is generally carried out in a water/alcohol solvent, and when metachloroperbenzoic acid is used, the reaction is generally carried out in methylene chloride or peracetic acid. The reaction temperature may range from about room temperature to about 100° C. Preferably, the reactant is added and the reaction mixture is heated to about 60° C. for about five hours.

Compounds of the formula I wherein X is sulfur may be converted into the corresponding compounds of the formula I wherein X is sulfone by reacting them with hydrogen peroxide. This reaction is usually carried out in an appropriate solvent at a temperature from about −50° C. to about 100° C. Preferably, 30 percent aqueous hydrogen peroxide is added to acetic acid so that the reaction mixture contains 1 equivalent of hydrogen peroxide per equivalent of the formula I compound, and the mixture is stirred at room temperature for about 3 days. Other appropriate solvents include methanesulfonic acid and formic acid.

Scheme 2 illustrates a method of preparing racemic mixtures of the starting materials of the formula VII. This method is exemplified in Example 1 of this application for compounds of the formula VII wherein X is sulfur. Compounds of the formula VII wherein X is oxygen may be prepared in an analogous fashion, by replacing the reactant of the formula

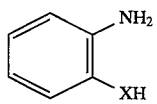

wherein X is sulfur, which is depicted in scheme 2 and referred to in Example 1B, sulfur with the corresponding reactant wherein X is oxygen.

Scheme 3 illustrates a method of synthesizing the "R" and "S" enantiomers of the starting materials of the formula VII wherein X is sulfur. These compounds are designated in scheme 3 as having the formula VII-A. (The chiral center of such compounds is designated with an asterisk in structure VII-A. Asterisks are also used to designate the same chiral carbon in the synthetic intermediates from which compounds of the formula VII-A are made.) Example 2 of this application describes the preparation of the "S" enantiomer by the method shown in scheme 3. The "R" enantiomer may be prepared in an analogous fashion by replacing the "S" enantiomer of the compound of formula IX depicted in scheme 3 and referred to in Example 3A (i.e., D-cysteine) with the corresponding "R" enantiomer (i.e., L-cysteine).

Scheme 4 illustrates a method of preparing the "R" and "S" enantiomers of compounds of the formula VII wherein X is oxygen. These compounds are referred to in scheme 4 as having the formula VII-B. (The chiral center of such compounds is designated with an asterisk in structure VII-B. Asterisks are also used to designate the same chiral carbon in the synthetic intermediates from which compounds of the formula VII-B are made.) Example 105 of this application describes the preparation of the "R" enantiomer by the method shown in scheme 4. The "S" enantiomer may be prepared in an analogous fashion, by replacing the "R" enantiomer of the compound of formula XV depicted in scheme 4 and referred to in Example 105A (i.e., N-t-butoxycarbonyl-D-serine) with the corresponding "S" enantiomer (i,e., N-t-butoxycarbonyl-L-serine). Racemic mixtures of compounds of the formula VII may be prepared in an analogous fashion according to the procedure of scheme 4, using the racemate of the starting material of formula XV.

When $R^7$ and $R^8$ are both hydrogen, the compound of formula XV employed is the N-t-butoxycarbonyl derivative ("the BOC derivative") of D-serine, L-serine or a racemic mixture of these amino acids. Other variations of $R^7$ and $R^8$ may be obtained using the BOC derivatives of D- and L-threonine, D- and L-allothreonine, and D- and L-2-amino-3-methyl-3-hydroxybutyric acid and the respective racemates of these compounds. D- and L-threonine and D- and L-serine are commercially available. D-allothreonine and L-allothreonine may be prepared as described by Pons et al., *Tetrahedron Letters*, 31, 5023 (1990). D- and L-2-amino-3-methyl-3-hydroxybutyric acid may be prepared as described by Belakon et al., *J.A.C.S.*, 107, 4252 (1985). The BOC derivatives of all of the above amino acids may be prepared as described by Keller et al., *Organic Synthesis*, 63, 160 (1984). All of the foregoing references are incorporated herein in their entirety.

The preparation of other compounds of the formulae I, XIX and XX not specifically described in the foregoing experimental section can be accomplished using combinations of the reactions described above that will be apparent to those skilled in the art.

In each of the reactions discussed or illustrated in schemes 1 to 3 above, pressure is not critical unless otherwise indicated. Pressures from about 0.5 atmospheres to about 5 atmospheres are generally acceptable, and ambient pressure, i.e., about 1 atmosphere, is preferred as a matter of convenience.

The compounds of the formula I (the active compounds of this invention) which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the active base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The active compounds of this invention and their pharmaceutically acceptable salts are useful as CCK receptor antagonists, i.e., they possess the ability to antagonize the effects of CCK at its receptor site in mammals, and therefore they are able to function as therapeutic agents in the treatment of the aforementioned disorders and diseases in an afflicted mammal.

The active compounds of this invention and their pharmaceutically acceptable salts can be administered via either the oral, parenteral or topical routes. In general, these compounds are most desirably administered in dosages ranging from about 5.0 mg up to about 1500 mg per day, although variations will necessarily occur depending upon the weight and condition of the subject being treated and the particular route of administration chosen. However, a dosage level that is in the range of about 0.07 mg to about 21 mg per kg of body weight per day is most desirably employed. Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The active compounds of the invention may be administered alone or in combination with pharmaceutically acceptable carriers or diluents by either of the three routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the active compounds of the present invention topically when treating inflammatory conditions of the skin and this may preferably be done by way of creams, jellies, gels, pastes, ointments and the like, in accordance with standard pharmaceutical practice.

The activity of the compounds of the present invention as CCK antagonists may be determined by an assay that measures their ability to inhibit the binding of 125-I-BH-CCK-8 to the CCK-B receptor in a guinea pig cortical membrane preparation. This procedure is carried out as follows. The cortex is dissected from one male Hartley Guinea pig and homogenized (15 strokes) with a teflon homogenizer in 20 volumes (w./v.) of the assay buffer, which consists of 50 mM Tris (i.e., trimethamine, which is 2-amino-2-hydroxymethyl-1,3-propanediol) hydrochloric acid having pH 7.4 and 5 mM of manganese chloride at 4° C. The homogenate is centrifuged at 4° C. for 30 minutes at 100,000×G. The pellet is resuspended in the same buffer and spun as described above. The final pellet is diluted to a concentration of 20 mg/ml with the assay buffer for use in the binding assay. The tissue is kept on ice at all times.

An incubation mixture is prepared, which consists of 50 uL of the tissue preparation, prepared as described above, 100 uL 125-I-BH-CCK-8 (to give a concentration of 50 pM in the final assay), 20 uL of a blank or the compound being tested, and 30 uL of Tris with 4% DMSO. All drugs and dilutions are made using 4% DMSO in the assay buffer yielding a final assay DMSO concentration of 1%.

The reaction is initiated with the addition of tissue to a 96-well plate containing 125-I-BH-CCK-8 and the appropriate blank or compound being tested. Non-specific binding is estimated using 1 uM sulphated CCK-8. The reaction is terminated by spinning the plates in a H1000B rotor fitted on a Sorvall RT6000 refrigerated centrifuge at 4° C. The supernatant is discarded, and the pellets washed with 200 uL of assay buffer, and the plate is spun as above. The supernatant is decanted again, and the pellet is harvested onto Betaplate filters (which have been soaked in 0.2% polyethyleneimine for a minimum of 2 hours) using a Skatron cell harvester at setting 222 using Tris HCl pH 7.4 as the wash buffer. The filtermats are counted on a Betaplate counter for 45 seconds per sample.

Data are expressed as $IC_{50}$ values (the concentration which inhibits 50% of the specific binding of 125-I-BH-CCK-8). The data is analyzed using non-linear regression analysis.

The present invention is illustrated by the following examples. It will be understood, however, that the invention is not limited to the specific details of these examples.

EXAMPLE 1

(R,S)-3-Amino-2,3-dihydro-1,5-benzothiazepin-4(5H)-one

This compound was prepared using the following procedure, which is similar to the procedure described in U.S. Pat. Nos. 4,539,150 and 4,531,151.

A. (R,S)-N-Carbobenzyloxy-D,L-serine methyl ester

To a solution of 7.69 g (0.0322M) of N-carbobenzyloxy-D,L-serine (Source: Aldrich Chemical Co.) In 75 mL of methanol was added 2.55 mL (0.0354M) of acetyl chloride (Source: Aldrich Chemical Co,). The mixture was stirred at room temperature for 16 hours. The methanol was evaporated, and the residue triturated with 100 mL of saturated sodium bicarbonate ($NaHCO_3$). The mixture was extracted with 2×100 mL of chloroform ($CHCl_3$). The $CHCl_3$ layer was dried and evaporated to yield 8.77 g of the above product as a colorless oil. TLC (10:1 $CHCl_3$: $CH_3OH$) rF=0.8.

¹H NMR (CDCl₃) δ7.28 (s, 5H), 5.85 (d, 1H), 5.16 (s, 2H), 4.44 (m, 1H), 3.95 (m, 2H), 3.82 (s, 3H).

B. N-Carbobenzyloxy-dehydroserine methyl ester

This compound was prepared by a procedure similar to that described in *J. Org Chem.*, 45, 3131 (1980). A mixture of 8.14 g (0.0321M) of N-carbobenzyloxy-D,L-serine methyl ester, 0.953 g (0.00963M) of cuprous chloride (Source: Mallinckrodt Chemical Co.) and 6.14 g (0.0320M) of 1-(3-dimethylamino-propyl)-3-ethyl carbodiimide hydrochloride (Source: Aldrich Chemical Co.) In 100 mL of $CH_3CN$ were heated to 40° C. for 2 hours under nitrogen gas ($N_2$). The mixture was cooled to room temperature and poured into a mixture of 200 mL of water and 200 mL of ethyl acetate (EtOAc). The EtOAc layer was removed, and the aqueous layer extracted with 2×100 mL of EtOAc. The EtOAc extracts were combined, dried with sodium sulfate ($Na_2SO_4$) and evaporated to yield 7.44 g of product as a yellow oil.

¹H NMR (CDCl₃) δ7.40 (s, 5H), 6.26 (s, 1H), 5.81 (s, 1H), 5.20 (s, 2H), 3.86 (s, 3H).

C. (R,S)-N-Carbobenzyloxy-S-(2-aminophenyl)cysteine methyl ester

A mixture of 8.79 g (0.037M) of N-carbobenzyloxy-dehydroserine methyl ester, 4.34 mL (0.037M) of 2-aminothiophenol (Source: Aldrich Chemical Co.) and 0.52 mL (0.0037M) of triethylamine (TEA) in 26 mL of methanol ($CH_3OH$) containing 13 mL of methylene chloride ($CH_2Cl_2$) were stirred at room temperature for 3 hours under $N_2$. The solvent was evaporated and the residue chromatographed on 600 g of silica using acetone containing 3% methanol as the eluant. The appropriate fractions were combined and evaporated to afford 11 g (83% yield) of the desired product as an oil. TLC (97:3 $CHCl_3$: Acetone) rF=0.5.

¹H NMR (CDCl₃) δ7.35–7.5 (m, 6H), 7.25 (m, 1H), 6.70 (m, 2H), 5.90 (d, 1H), 5.05 (s, 2H), 4.60 (m, 1H), 4.0–4.4 (bs, 2H), 3.52 (s, 3H), 3.30 (m, 2H).

D. (R,S)-3-Carbobenzyloxyamino-2,3-dihydro-1,5-benzothiazepin-4-(5H)-one

A mixture of 2.69 g (0.00751M) of N-carbobenzyloxy-S-(2-aminophenyl)cysteine methyl ester and 10 mg (0.0000525M) of p-toluenesulfonic acid monohydrate (Source: Aldrich Chemical Co. was refluxed in 50 mL of xylene for 3 hours. Another 20 mg of p-toluenesulfonic acid monohydrate was added and the reflux continued for 5 hours. The reaction was cooled to room temperature and stirred for 16 hours. The resulting precipitate was filtered, triturated with ether, refiltered and dried to give 2.0 g (81% yield) of the product as a white solid.

MP=127° C.

¹H NMR (CDCl₃) δ7.775 (br s, 1H), 7.0–7.4 (m, 9H), 5.85 (d, 1H), 5.05 (s, 2H), 4.53 (m, 1H), 3.85 (m, 1H), 2.95 (m, 1H).

E.   (R,S)-3-Amino-2,3-dihydro-1,5-benzothiazepin-4(5H)-one

To 8.17 mL of 25% hydrogen bromide (HBr) dissolved in acetic acid was added 1.75 g (0.00534M) of 3-carbobenzyloxyamino-2,3-dihydro-1,5-benzthiazepin-4(5H)-one, and the solution was stirred for 1 hour at room temperature. A precipitate gradually formed. To the mixture was added 35 mL of ether and the precipitate collected via filtration. The precipitate was dissolved in a minimal amount of water and the pH adjusted to 9.0 with solid $NaHCO_3$. The resulting precipitate was filtered and dried to yield 0.735 mg (70%) of product as a white solid.

M.p.=180° C.

¹H NMR (D₆DMSO) δ9.95 (br s, 1H), 7.55 (d, 1H), 7.40 (t, 1H), 7.0–7.2 (m, 2H), 3.4 (m, 1H), 3.30 (m, 1H), 280 (m, 1H).

EXAMPLE 2

(S)-3-Amino-2,3-dihydro-1,5-benzothiazepin-4(5H)-one

The title compound was synthesized by the following procedure which is similar to that outlined in *Journal of Medicinal Chemistry*, 28, 1517 (1985), with the exception that L-cysteine was used in place of D-cysteine as the starting material.

A. N-Acetyl-D-Cysteine

The title compound was prepared using a procedure similar to that reported in *Journal of Organic Chemistry*, 30, 2839 (1965) with the exception that D-cysteine hydrochloride monohydrate (Source: Aldrich Chemical Co.) was used as the starting material.

B. S-(o-Nitrophenyl)-N-acetyl-D-cysteine

A mixture of 9.28 g (56.9 mmol) of (S)-N-acetyl-cysteine, 7.43 mL (70.5 mmol) of 1-fluoro-2-nitrobenzene and 13.66 g (163 mmol) of sodium bicarbonate was refluxed in 136 mL of ethanol and 41 mL of water for 3 hours. The mixture was cooled to room temperature and the solvent evaporated. The residue was dissolved in 136 mL of water and extracted with ether. The water solution was then acidified to pH=1 with 12N hydrochloric acid (HCl). The resulting yellow precipitate was filtered to yield 13.6 g (84%) of product.

Mp=188°–190° C.

C. S-(o-Nitrophenyl)-D-cysteine

A solution of 13.6 g (47.9 mmol) of S-(o-nitrophenyl)-N-acetyl-D-cysteine was refluxed in 57 mL of 18M sulfuric acid ($H_2SO_4$) for 1 hour. The bright yellow solution was cooled to 0° C. and concentrated. Ammonium hydroxide ($NH_4OH$) was added to adjust the pH=5.4. The resulting precipitate was filtered and dried to yield 11.6 g (100% ) of product.

M.p.=186°–187° C.

D. S-(o-Nitrophenyl)-N-carbobenzyloxy-D-cysteine

A solution of 11.60 g (48 mmol) of S-(o-nitrophenyl)-D-cysteine in 36 mL of 4N sodium hydroxide (NaOH) was cooled to 0° C. To this solution was added dropwise 6.85 mL (48 mmol) of carbobenzyloxychloride, and the mixture was stirred at room temperature for 2.5 hours. The pH was maintained at 10.8 with the addition of 4N NaOH as needed. The solution was then extracted with ether and the pH adjusted to 1.0 with 12N HCl. The resulting precipitate was dissolved in $CH_2Cl_2$, dried with $Na_2SO_4$ and evaporated to yield 17.0 g of product as a yellow gum. This material was used as is in the next reaction.

E. S-(O-Aminophenyl)-N-carbobenzyloxy-D-cysteine

To a yellow solution of 17.0 g (45.2 mmol) of S-(o-nitrophenyl)-N-carbobenzyloxy-D-cysteine in 800 mL of methanol containing 4.84 g (90.4 mmol) of ammonium chloride ($NH_4Cl$) was added 41.1 g (633 mmol) of zinc dust. The resulting gray slurry was refluxed for 4 hours. The hot solution was then filtered, and the solid residue washed with an additional 200 mL of methanol. The filtrate was evaporated and the solid residue triturated with 320 mL of 1N HCl. Upon stirring for ½ hour, the initial gummy mass crystallized to a white solid. Filtration of the solid yielded 13.1 g (84%) of S-(o-aminophenyl)-N-carbobenzyloxy-D-cysteine.

M.p.=169°–170° C.

F. 3(S)-[(Carbobenzyloxy)amino]-2,3-dihydro-1,5-benzothiazepin-4(5H)-one

A mixture of 13.10 g (37.9 mmol) of S-(o-aminophenyl)-N-carbobenzyloxy-D-cysteine and 7.27 g (37.9 mmol) of 1-(3-dimethylaminopropyl)-3-ethylcarbodiimide hydrochloride in 82 mL of DMF was stirred at room temperature for 2 hours. To this solution was added 330 mL of ethyl acetate. The mixture was extracted 4 times with 200 mL of 1N NaOH. The ethyl acetate solution was dried with magnesium sulfate (MgSO$_4$) and evaporated to a white amorphous residue. The residue was triturated with ether, and the resulting white crystals were filtered to yield 6.70 g (54%) of 3(S)-[(Carbobenzyloxy)amino]-2,3-dihydro-1,5-benzothiazepin-4(5H)-one as a white solid.

M.p.=190°–191° C. [α]$_D$=+200° (c=0.99, CHCl$_3$).

G. 3-(S)-Amino-2,3-dihydro-1,5-benzothiazepin-4(5H)-one

A mixture of 6.2 g (18.9 mmol) of 3(S)-[(carbobenzyloxy)amino]-2,3 dihydro-1,5-benzothiazepin-4(5H)-one and 25 mL of a 30% HBr solution in acetic acid was stirred at room temperature for 1 hour. There was noticeable evolution of carbon dioxide gas (CO$_2$) and the initial suspension gradually went into solution. After solution was obtained, a heavy precipitate was formed. The precipitate was filtered, and the solid triturated with 75 mL of NaHCO$_3$ and 75 mL of ethyl acetate. The ethyl acetate layer was dried and evaporated. The residue was triturated to yield 1.7 g of product as a white solid. Neutralization of the filtrate and extraction yielded an additional 1.15 g of product. The two solids were combined to yield 2.85 g (78%) of 3-(S)-amino-2,3-dihydro-1,5-benthiazepin-4(5H)-one.

EXAMPLE 3

(R,S)-N-(3-Methylphenyl)-N'-(2,3,4,5-tetrahydro-4oxo-1,5-benzothiazepin-3-yl)-urea A solution of 142 mg (0.732 mM) of 3-amino-2,3-dihydro-1,5-benzthiazepin-(5H)-one in 9 mL of CH$_2$Cl$_2$ was cooled to 0° C. To this solution was added dropwise 0.094 mL (0.732 mM) of m-tolyl isocyanate (Source: Aldrich Chemical Co.) dissolved in 4 mL of CH$_2$Cl$_2$, and the reaction stirred at 0° C. for 15 minutes. The resulting precipitate was filtered and dried to yield 187 mg (78% yield) of product as a white solid.

MP=208° C.

$^1$H NMR (D$_6$DMSO) δ8.7 (s, 1H), 7.5 (d, 1H), 7.35 (t, 1H), 6.8–7.1 (m, 6H), 6.5 (m, 2H), 4.25 (m, 1H), 3.55 (m, 1H), 3.0 (m, 1H), 2.10 (s, 3H).

The title compounds of Examples 4–10 were prepared using a procedure similar to that described in Example 3.

EXAMPLE 4

(S)-N-(3-Methylphenyl)-N'-(2,3,4,5-tetrahydro-4-oxo-1,5-benzothiazepin-3-yl)-urea $^1$H NMR (D$_6$DMSO) δ10.28 (s, 1H), 8.76 (s, 1H), 7.63 (d, 1H), 6.65–7.50 (m, 8H), 4.30–4.42 (m, 2H), 3.00–3.70 (m, 2H), 2.20 (s, 3H).

EXAMPLE 5

(R,S)-N-(3-Methoxyphenyl)-N'-(2,3,4,5-tetrahydro-4-oxo-1,5-benzothiazepin -3-yl)-urea $^1$H NMR (D$_6$ DMSO) δ8.92 (s, 1H), 7.65 (d, 1H), 7.48 (t, 1H), 7.0–7.3 (m, 4H), 6.8 (m, 2H), 6.45 (d, 1H), 4.38 (m, 1H), 3.70 (s, 1H), 3.68 (m, 1H), 3.05 (t, 1H).

EXAMPLE 6

(R)-N-(3-Methoxyphenyl)-N'-(2,3,4,5-tetrahydro-4-oxo-1,5benzothiazepin-3-yl)-urea $^1$H NMR (D$_6$DMSO) δ10.28 (s, 1H), 8.84 (s, 1H), 7.62 (d, 1H), 6.45–7.50 (m, 8H), 4.30–4.42 (m, 1H), 3.70 (s, 3H), 3.0–3.75 (m, 2H).

EXAMPLE 7

(S)-N-(3-Methoxyphenyl)-N'-(2,3,4,5-tetrahydro-4-oxo-1,5-benzothiazepin-3-yl)-urea $^1$H NMR (D$_6$DMSO) δ10.28 (s, 1H), 8.84 (s, 1H), 7.62 (d, 1H), 6.45–7.50 (m, 8H), 4.30–4.42 (m, 1H), 3.70 (s, 3H), 3.0–3.75 (m, 2H).

EXAMPLE 8

(R)-N-(3-Chlorophenyl)-N'-(2,3,4,5-tetrahydro-4-oxo-1,5-benzothiazepin-3-yl)-urea $^1$H NMR (D$_6$DMSO) δ10.29 (s, 1H), 9.02 (s, 1H), 7.66 (d, 1H), 6.75–7.60 (m, 1H), 4.30–4.42 (m, 1H), 3.00–3.70 (m, 2H).

EXAMPLE 9

(S)-N-(3-Chlorophenyl)-N'-(2,3,4,5-tetrahydro-4-oxo-1,5-benzothiazepin-3-yl-urea $^1$H NMR (D$_6$DMSO) δ10.29 (s, 1H), 9.02 (s, 1H), 7.66 (d, 1H), 6.75–7.60 (m, 1H), 4.30–4.42 (m, 1H), 3.00–3.70 (m, 2H).

EXAMPLE 10

(R,S)-N-(4-chlorophenyl)-N'-(2,3,4,5-tetrahydro-4-oxo-1,5-benzothiazepin-3-yl)-urea M.p.=225° C. (decomp.).

$^1$H NMR (D$_6$DMSO) δ8.8 (d, 1H), 6.9–7.7 (m, 10H), 4.65 (m, 1H), 3.70 (m, 1H), 3.35 (t, 1H).

EXAMPLE 11 tert-Butyliodoacetate

A mixture of 9.90 mL (0.61M) of tert-butyl bromoacetate (Source: Aldrich Chemical Co.) and 10.1 g (0.67M) sodium iodide (NaI) was refluxed in acetone for 3 hours. The mixture was cooled to room temperature and filtered. The resulting filtrate was evaporated to yield a solid residue which was suspended in ether. The ether suspension was washed with water and saturated sodium chloride (NaCl). The resulting ether solution was dried with MgSO$_4$ and evaporated to yield 15 g (100% yield) of product as a yellow oil. TLC (7:3 hexanes: ethyl acetate) rF=0.57.

$^1$H NMR (CDCl$_3$) δ3.5 (s, 2H) 1.4 (s, 9H).

EXAMPLE 12

4.4-Dimethylpiperidine

To a suspension of 1.52 g (0.04 m) of lithium aluminum hydride in 30 mL of THF was added dropwise, over a 15 minutes period, a solution of 2.82 g (0.02M) of 3,3-dimethylglutarimide in 15 mL of THF. The reaction was stirred at room temperature for 1 hour and then quenched with 50 mL of water. The reaction mixture was filtered, and the filtrate extracted with ethyl acetate. The ethyl acetate extract was dried (Na$_2$SO$_4$) and evaporated to yield 1.33 g (59%) of the product as an oil.

$^1$H NMR (CDCl$_3$) δ3.05 (m, 4H), 1.60 (m, 4H), 0.85 (s, 6H).

EXAMPLE 13

4,4-Tetramethylenepiperidine

The title compound was prepared by a procedure similar to that of Example 12.

$^1$H NMR (CDCl$_3$) δ2.75 (m, 4H), 1.35–1.8 (m, 12H).

EXAMPLE 14 tert-Butylchloroacetamide

A solution of 23.91 mL (0.30M) of chloroacetyl chloride was dissolved in 600 mL of ethyl acetate and cooled to 0° C. To this was added 62.93 mL (0.60M) of tert-butyl amine (Source: Aldrich Chemical Co.) An immediate white precipitate resulted. The slurry was stirred for 12 hours at room temperature. The mixture was filtered and the filtrate washed with 1N $H_3PO_4$, saturated $NaHCO_3$ and saturated NaCl. The ethyl acetate solution was dried ($Na_2SO_4$) and evaporated to yield 34.1 g (76% yield) of product as a white solid. TLC (7:3 hexanes:ethyl acetate) rF=0.42.

$^1$H NMR ($CDCl_3$) δ3.90 (s, 2H) 1.3 (s, 9H).
MS: 149.1,151.1 (p+1).

The title compounds of Examples 15–31 (a) were prepared by a procedure similar to that of Example 14.

EXAMPLE 15

N-Chloroacetyl-3,3-dimethylpiperidine
Colorless oil, 95% yield.
$^1$H NMR ($CDCl_3$) δ4.32 (m, 2H) 3.72 (t, 1H) 3.63 (t, 1H), 3.50 (s, 1H), 3.34 (s, 1H), 1.90 (m, 1H), 1.80 (m, 1H), 1.66 (m, 2H) 1.18 (s, 3H) 1.12 (s, 3H).

EXAMPLE 16

N,N-Diisopropylchloroacetamide
Yellow crystals, 41% yield.
$^1$H NMR ($CDCl_3$) δ4.04 (s, 2H), 3.96 (m, 1H), 3.45 (m, 1H), 1.40 (d, 6H), 1.14 (d, 6H).

EXAMPLE 17

N-Chloroacetylmorpholine
Colorless oil, 28% yield. TLC (95:5 $CHCl_3$:acetone) rF=0.2.
$^1$H NMR ($CDCl_3$) δ4.04 (s, 2H), 3.68 (m, 4H), 3.56 (m, 2H), 3.48 (m, 2H).

EXAMPLE 18

N-Chloroacetyl-3,3-tetramethylenepiperidine
$^1$H NMR ($CDCl_3$) δ4.02 (d, 2H), 3.50 (m, 1H), 3.35 (m, 1H), 3.30 (s, 1H), 3.10 (s, 1H), 1.2–1.80 (m, 12H).

EXAMPLE 19

N-Chloroacetyl-4,4-tetramethylenepiperidine
Colorless oil, 92% yield.
$^1$H NMR ($CDCl_3$) δ4.04 (s, 2H), 3.55 (t, 2H), 3.40 (t, 2H), 1.2–1.7 (m, 12H).

EXAMPLE 20

N-Chloroacetyl-4,4-pentamethylenepiperidine
$^1$H NMR ($CDCl_3$) δ4.02 (s, 2H), 3.6 (m, 2H), 3.4 (m, 2H), 1.3–1.5 (m, 14H).

EXAMPLE 21

N-Chloroacetyl-4,4-ethylenedioxypiperidine
81% yield, clear oil.
$^1$H NMR ($CDCl_3$) δ4.04 (s, 2H), 3.90 (s, 4H), 3.61 (t, 2H), 3.50 (t, 2H), 1.58–1.78 (m, 4H).

EXAMPLE 22

N-Chloroacetyl-4,4-dimethylpiperidine
Colorless oil, 38% yield.
$^1$H NMR ($CDCl_3$) δ4.06 (s, 2H), 3.55 (t, 2H), 3.42 (t, 2H), 1.36 (m, 4H), 0.95 (s, 6H).

EXAMPLE 23

N-Benzyl-N-tert-butylchloroacetamide
Colorless oil, 100% yield.
$^1$H NMR ($CDCl_3$) δ7.15–7.4 (m, 5H), 4.62 (s, 2H), 3.96 (s, 3H), 1.41 (s, 9H).

EXAMPLE 24

N-Methyl-N-tert-butylchloroacetamide
Colorless oil, 77% yield.
$^1$H NMR ($CDCl_3$) δ3.69 (s, 2H), 2.87 (s, 3H), 1.36 (s, 9H).

EXAMPLE 25

N-Chloroacetyl-4phenylpiperidine
Clear oil, 97% yield.
$^1$H NMR ($CDCl_3$) δ7.04–7.56 (m, 5H), 4.71 (d, 1H), 4.1 (d, 2H), 3.98 (d, 1H), 3.21 (t, 1H), 2.74 (q, 2H), 1.90 (t, 2H), 1.70 (m, 2H).

EXAMPLE 26

N-Chloroacetyl-4-benzylpiperidine.
Colorless oil.
$^1$H NMR ($CDCl_3$) δ7.1–7.4 (m, 5H), 4.55 (d, 1H), 4.10 (s, 2H), 3.82 (d, 1H), 3.0 (t, 1H), 2.6 (m, 3H), 1.7 (m, 3H), 1.2 (m, 2H).

EXAMPLE 27

N-Chloroacetyl-4-(3-phenylpropyl)piperidine
Oil.
$^1$H NMR ($CDCl_3$) δ7.04–7.31 (m, 5H), 4.52 (d, 1H), 4.05 (s, 2H), 3.80 (d, 1H), 3.05 (t, 1H), 2.59 (m, 3H), 1.40–1.79 (m, 5H), 1.01–1.40 (m, 4H).

EXAMPLE 28

N-Chloroacetyl-2,6-dimethylpiperidine
Colorless oil (39% yield).
$^1$H NMR ($CDCl_3$) δ3.95 (s, 2H), 4.5 (m, 2H), 1.0–1.8 (m, 12H).

EXAMPLE 29

N-Chloroacetyl-3,5-dimethylpiperidine
Oil, 91% yield.
$^1$H NMR ($CDCl_3$) δ4.48 (d, 1H), 4.04 (m, 2H), 3.62 (d, 1H), 3.45 (m, 1H), 2.98–3.21 (m, 1H), 2.5 (t, 1H).

EXAMPLE 30

N-Chloroacetyl-2-methylpiperidine
Colorless oil, 30% yield,
$^1$H NMR ($CDCl_3$) δ3.95 (s, 2H), 2.5–4.5 (m, 3H), 1.0–1.7 (m, 9H).

EXAMPLE 31

N-Chloroacetyl-1,3,4,5,6,7,8-octahydroisoquinoline
Oil, 100% yield.
$^1$H NMR (CDCl$_3$) δ4.6 (d, 1H), 4.4 (d, 1H), 3.98 (s, 2H), 3.8 (d, 1H), 3.6 (d, 1H), 0.6–3.4 (m, 12H).

EXAMPLE 31(a)

N-Chloroacetyl-3,3,5,5-tetramethylpiperidine
$^1$H NMR (CDCl$_3$) δ4.05 (s, 2H), 3.70 (s, 2H), 3.02 (s, 3H), 1.25 (s, 2H), 0.92 (s, 3H), 0.90 (s, 3H).

EXAMPLE 32 tert-Butyl iodoacetamide
A mixture of 34.1 g (0.228M) of tert-butyl chloroacetamide and 37.6 g of NaI was refluxed in 600 mL of acetone for 12 hours. The reaction was cooled to room temperature and evaporated. The residue was suspended in ethyl acetate and washed with water and saturated NaCl. The ethyl acetate solution was dried (Na$_2$SO$_4$) and evaporated to yield 52.2 g (95% yield) of product as a white solid.
$^1$H NMR (CDCl$_3$) δ3.60 (s, 2H), 1.30 (s, 9H).
MS: 242.1 (p+1).
The title compounds of Examples 33–50(a) were prepared by a procedure similar to that of Example 32.

EXAMPLE 33

N-Iodoacetyl-3,3-dimethylpiperidine
Colorless oil, 97% yield.
$^1$H NMR (CDCl$_3$) δ4.90 (m, 2H), 3.50 (m, 1H), 3.30 (m, 1H), 3.22 (s, 1H), 3.00 (s, 1H), 1.70 (m, 1H), 1.50 (m, 1H), 1.38 (m, 2H), 0.96 (s, 3H), 0.90 (s, 3H).

EXAMPLE 34

N,N-Diisopropyl iodoacetamide
Yellow oil, 76% yield.
$^1$H NMR (CDCl$_3$) δ3.84 (m, 1H), 3.66 (s, 2H), 3.36 (m, 1H), 1.32 (d, 6H), 1.22 (d, 6H).

EXAMPLE 35

N-Iodoacetylmorpholine
Colorless oil, 57% yield.
$^1$H NMR (CDCl$_3$) δ3.66 (m, 4H), 3.58 (m, 1H), 3.52 (m, 1H), 3.38 (m, 2H).

EXAMPLE 36

N-Iodoacetyl-3,3-tetramethylenepiperidine
$^1$H NMR (CDCl$_3$) δ3.35 (s, 2H), 3.5 (s, 1H), 3.3 (m, 1H), 3.30 (o, 1H), 3.06 (s, 1H), 1.2–1.8 (m, 12H).

EXAMPLE 37

N-Iodoacetyl-3,3-pentamethylenepiperidine
$^1$H NMR (CDCl$_3$) δ3.72 (m, 2H), 3.06–3.50 (m, 4H), 1.13–1.74 (m, 14H).

EXAMPLE 38

N-Iodoacetyl-4,4-tetramethylenepiperidine
Colorless oil, 100% yield.
$^1$H NMR (CDCl$_3$) δ3.72 (s, 2H), 3.52 (t, 2H), 3.37 (t, 2H), 1.3–1.7 (m, 12H).

EXAMPLE 39

N-Iodoacetyl-4,4-pentamethylenepiperidine
Oil, 51% yield.
$^1$H NMR (CDCl$_3$) δ3.74 (s, 2H), 3.55 (t, 1H), 3.33 (t, 2H), 1.31–1.55 (m, 14H).

EXAMPLE 40

N-Iodoacetyl-4,4-ethylenedioxypiperidine
Oil, 78% yield.
$^1$H NMR (CDCl$_3$) δ3.95 (s, 4H), 3.73 (s, 2H), 3.68 (t, 2H), 3.5 (t, 2H), 1.8 (t, 2H), 1.68 (t, 2H).

EXAMPLE 41

N-Iodoacetyl-4,4-dimethylpiperidine
Colorless oil, 92% yield.
$^1$H NMR (CDCl$_3$) δ3.72 (s, 2H), 3.55 (t, 2H), 3.38 (t, 2H), 1.45 (t, 2H), 1.35 (t, 2H), 1.0 (s, 6H).

EXAMPLE 42

N-Benzyl-N-tert-butyl-iodoacetamide
Colorless oil, 91% yield.
$^1$H NMR (CDCl$_3$) δ7.15–7.4 (m, 5H), 4.60 (s, 2H), 3.59 (s, 2H), 1.40 (s, 9H).

EXAMPLE 43

N-Methyl-N-tert-butyl-iodoacetamide
Colorless oil, 98% yield.
$^1$H NMR (CDCl$_3$) δ3.66 (s, 2H), 2.88 (s, 3H), 1.36 (s, 9H).

EXAMPLE 44

N-Iodoacetyl-4-benzylpiperidine
Yellow oil, 93% yield.
$^1$H NMR (CDCl$_3$) δ7.1–7.4 (m, 5H), 4.5 (d, 1H), 3.7 (m, 3H), 3.0 (t, 1H), 2.5 (m, 3H), 1.7 (m, 3H), 1.3 (m, 2H).

EXAMPLE 45

N-Iodoacetyl-4-phenylpiperidine
Brown oil, 84% yield.
$^1$H NMR (CDCl$_3$) δ7.2–7.4 (m, 5H), 4.75 (d, 1H), 3.9 (d, 1H), 3.79 (d, 2H), 3.2 (t, 1H), 2.75 (m, 2H), 1.56–2.01 (m, 4H).

EXAMPLE 46

N-Iodoacetyl-4-(3-phenylpropyl)piperidine
Yellow oil, 96% yield.
$^1$H NMR (CDCl$_3$) δ7.1–7.4 (m, 5H), 4.5 (d, 1H), 3.75 (m, 3H), 3.0 (t, 1H), 2.60 (m, 3H), 1.5–1.8 (m, 5H), 1.0–1.4 (m, 4H).

EXAMPLE 47

N-Iodoacetyl-2,6-dimethylpiperidine
Yellow oil.
$^1$H NMR (CDCl$_3$) δ4.7 (m, 1H), 4.0 (M, 1H), 3.60 (s, 2H), 0.8–1.7 (m, 12H).

EXAMPLE 48

N-Iodoacetyl-3,5-dimethylpiperidine
Oil, 72% yield.
$^1$H NMR (CDCl$_3$) δ3.7 (d, 2H), 3.3–3.8 (m, 4H), 1.2–1.8 (m, 4H), 0.7–0.9 (m, 6H).

EXAMPLE 49

N-Iodoacetyl-2-methylpiperidine
Clear oil, 91% yield.
$^1$H NMR (CDCl$_3$) δ3.6 (s, 2H), 2.5–4.6 (m, 3H), 1.0–1.6 (m, 9H).

EXAMPLE 50

N-Iodoacetyl-1,3,4,5,6,7,8-octahydroisoquinoline
Yellow oil, 58% yield.
$^1$H NMR (CDCl$_3$) δ4.0–4.5 (m, 2H), 3.6 (s, 2H), 3.0–3.6 (m, 2H), 0.6–3.0 (m, 12H).

EXAMPLE 50(a)

N-Iodoacetyl-3,3,5,5-tetramethylpiperidine
$^1$H NMR (CDCl$_3$) δ3.72 (s, 2H), 3.15 (s, 2H), 2.95 (s, 2H), 1.22 (s, 2H), 0.95 (s, 3H), 0.90 (s, 3H).

EXAMPLE 51

(R,S)-3,4-Dihydro-4-oxo-3-[[(3-methylphenylamino)carbonyl]amino]-1,5-benzothiazepine-5(2H)-acetic acid-1,1-dimethylethyl ester A solution of 0.100 g (0.305 mM) of N-(3-methylphenyl)-N'-(2,3,4,5-tetrahydro-4-oxo-1,5-benzothiazepin-3-yl)-urea in 20 mL of anhydrous THF was cooled to –78° C. under nitrogen in a flame dried round-bottomed flask. To this was added 0.915 mL (0.915 mM) of a 1M solution of lithium bis(trimethylsilyl)amide in THF (Source: Aldrich Chemical Co.). The solution was stirred at –78° C. for 30 minutes. To this solution was added dropwise 0.074 g (0.305 mM) of tert-butyl iodoacetate in 3 mL of anhydrous THF. After addition was complete, the reaction was warmed to room temperature and stirred for 2 hours. To the solution was added 15 mL of water and the resulting mixture was extracted with 50 mL of ethyl acetate. The ethyl acetate layer was dried (Na$_2$SO$_4$) and evaporated to yield a solid residue. This material was triturated with ether and filtered to yield 62 mg (47% yield) of the product as a white solid.
MP=136°–137° C.
$^1$H NMR (CDCl$_3$) δ7.62 (d, 1H), 7.15–7.4 (m, 4H), 7.0 (m, 2H), 6.75 (m, 1H), 4.60 (m, 2H), 4.10 (m, 1H), 3.80 (m, 1H), 2.80 (m, 1H), 2.20 (s, 3H), 1.30 (s, 3H).

EXAMPLE 52

(R,S)-N-(3-Methylphenyl)-N'-(2,3,4-trihydro-4-oxo-5-methyl-1,5-benzothiazepin-3-yl)-urea
The title compound was prepared by a procedure similar to that of Example 51.
M.p.=229° C.
$^1$H NMR (CDCl$_3$) δ6.6–7.8 (m, 10H), 4.75 (m, 1H), 3.8 (m, 1H), 3.45 (s, 3H), 2.95 (m, 1H), 2.20 (s, 3H).

EXAMPLE 53

(R,S)-3,4-Dihydro-4-oxo-3-amino-1,5-benzothiazepine-5(2H)-acetic acid-1,1-dimethylethyl ester A solution of 0.515 g (0.00265M) of 3-amino-2,3-dihydro-1,5-benzothiazepin-4(5H)-one in 5 mL of anhydrous THF was cooled to –78° C. under nitrogen in a flame dried round-bottomed flask. To this solution was added dropwise 2.65 mL (0.265M) of lithium bis(trimethylsilyl)amine. The mixture was stirred at –78° C. for 30 minutes. To this solution was added dropwise 0.642 g (0.00265M) of tert-butyl iodoacetate dissolved in 6 mL of anhydrous THF. After the addition was complete, the reaction was warmed to room temperature and stirred for 2 hours. To this mixture was added 10 mL of water, and the mixture extracted with ethyl acetate. The ethyl acetate extract was dried (Na2SO4) and evaporated to yield 0.556 g (68% yield) of product.
$^1$H NMR (CDCl$_3$) δ7.58 (d, 1H), 7.0–7.4 (m, 3H), 4.75 (d, J=6Hz, 1H), 3.90 (d, J=6Hz, 1H), 3.55 (m, 2H), 2.76 (m, 1H), 1.84 (br s, 2H), 1.46 (s, 3H), 1.40 (s, 3H).

EXAMPLE 53A 3-(S)-Amino-5-[2-oxo-2-(3,3dimethyl-piperidin-1-yl)-ethyl]-3,4-dihydro-1,5-benzothiazepin-4-one
The title compound was prepared by a procedure similar to that described in Example 53.
$^1$H NMR (CDCl$_3$) δ7.60 (d, 1H) 7.25–7.50 (m, 2H), 7.20 (t, 1H), 5.25 (d, d, 1H), 3.90 (m, 1H), 2.7–3.7 (m, 5H), 1.3–1.7 (m, 4H), 0.8–1.0 (s, s, s, 6H).
Mass spectrum: m/e=347 (p).

EXAMPLE 54

(R,S)-3,4-Dihydro-4-oxo-3-[[(3-chlorophenylamino)carbonyl]amino]-1,5benzothiazepine-5(2H)-acetic acid-1,1-dimethylethyl ester To a cooled (0° C.) solution of 0.157 g (0.00051M) of 3,4-dihydro-4-oxo-3-amino-1,5-benzothiazepine-5(2H)-acetic acid-1,1-dimethylethyl ester in 5 mL of CH$_2$Cl$_2$ was added 0.63 mL (0.00051M) of 3-chlorophenyl isocyanate. The mixture was warmed to room temperature and stirred for 1 hour. The solvent was then evaporated and the residue triturated with ether to afford 109 mg (47% yield) of product as a white solid.
M.p.=142° C.
$^1$H NMR (D$_6$DMSO) δ9.05 (s, 1H), 7.7 (d, 1H), 7.6 (m, 2H), 7.3–7.5 (m, 2H), 7.25 (t, 1H), 7.1 (d, 1H), 6.92 (d, 1H), 6.80 (d, 1H), 4.3–4.6 (m, 3H), 3.55 (m, 1H), 3.0 (t, 3H), 1.28 (s, 9H).

The title compounds of Examples 55 and 56 were prepared by a procedure similar to that of Example 54.

EXAMPLE 55

(R,S)-3,4-Dihydro-4-oxo-3-[[(3-methoxyphenylamino)carbonyl]amino]-1,5-benzothiazepine-5(2H)-acetic acid-1,1-dimethylethyl ester
M.p.=140° C.
$^1$H NMR (D$_6$DMSO) δ8.85 (s, 1H), 7.7 (d, 1H), 7.6 (m, 1H), 7.3–7.5 (m, 2H), 7.1 (m, 2H), 6.75 (m, 2H), 6.45 (d, 1H), 4.3–5.8 (m, 3H), 3.55 (s, 3H), 3.48 (m, 1H), 3.0 (m, 1H), 1.3 (s, 9H).

EXAMPLE 56

(R,S)-3,4-Dihydro-4-oxo-3-[[(4-chlorophenylamino)carbonyl]amino]-1,5-benzothiazepine-5(2H)-acetic acid-1,1-dimethylethyl ester
MP=216° C.
$^1$H NMR (D$_6$DMSO) δ8.90 (s, 1H), 7.6 (d, 1H), 7.5 (m, 1H), 7.1–7.4 (m, 6H), 6.75 (d, 1H), 4.3–4.6 (m 3H), 3.6 (m, 1H), 3.0 (m, 1H), 1.4 (s, 9H).

EXAMPLE 57

(R,S)-N-(1,1-Dimethylethyl)-3,4-dihydro-4-oxo-3-[[(3methylphenylamino)carbonyl]amino]-1,5-benzothiazepine-5(2H)-acetamide
To a flame dried round-bottomed flask under nitrogen was added a solution of 0.100 g (0.305 mM) of N-(3-methylphenyl)-N'-(2,3,4,5-tetrahydro-4-oxo-1,5-benzothiazepin-3-yl)- urea dissolved in 20 mL of anhydrous THF. The solution was cooled to −78° C. To this solution was added 0.915 mL (0.915 mM) of a 1M solution of lithium bis(trimethylsilyl)amide dissolved in THF. The mixture was stirred for 30 minutes at −78° C. To this solution was added dropwise 0.0735 g of tert-butyl iodoacetamide dissolved in 2 mL of THF. The reaction mixture was warmed to room temperature and stirred for 2 hours. To this mixture was added 10 mL of water, and the mixture extracted with ethyl acetate. The ethyl acetate extracts were dried ($Na_2SO_4$) and evaporated. The residue was triturated with ether and filtered to yield the product as a white solid.

M.p.=233° C.

$^1$H NMR ($CDCl_3$) δ7.72 (d. 1H), 7.51 (m, 1H), 7.30 (m, 2H), 7.15 (m, 2H), 7.03 (d, 1H), 6.92 (d, 1H), 6.75 (s, 1H), 6.5 (s, 1H), 4.8 (d, 1H), 4.65 (m, 1H), 4.25 (d, 1H), 3.87 (m, 1H), 2.90 (t, 1H), 2.35 (s, 3H), 1.30 (s, 3H), 1.22 (s, 3H).

The title compounds of Examples 58–91(b) were prepared by procedures similar to that described in Example 57.

EXAMPLE 58

(R,S) -N,N-(1-Methylethyl)-3,4-dihydro-4-oxo-3-[[(3-methylphenylamino)carbonyl]amino]-1,5-benzothiazepine-5-(2H)-acetamide M.p.=150° C.

$^1$H NMR ($CDCl_3$) δ7.6 (d, 1H), 7.4 (m ,2H), 7.25 (m, 3H), 7.0 (m, 2H), 6.72 (m, 1H), 6.40 (m, 1H), 5.0 (d, 1H), 4.66 (m, 1H), 4.10 (m, 1H), 3.85 (m, 2H), 3.55 (m, 1H), 2.18 (s, 3H), 1.2–1.4 (m, 12H).

Mass spectrum: m/e=468.21643.

EXAMPLE 59

(R)-N,N-(1-Methylethyl)-3,4-dihydro-4-oxo-3-[[(3-methylphenylamino)carbonyl]amino]-1,5-benzothiazepine-5(2H)-acetamide $^1$H NMR ($CDCl_3$) δ6.52–7.65 (m, 10H), 5.10 (d, 1H), 4.70 (m, 1H), 4.10 (d, 1H), 3.90 (m, 1H), 3.75 (m, 1H), 3.58 (br s, 1H), 3.00 (t, 1H), 2.14 (s, 3H), 1.00–1.50 (m, 12H).

EXAMPLE 60

(R,S)-1-[3,4-Dihydro-4-oxo-3-[[(3-methylphenylamino)carbonyl]amino]-1,5-benzothiazepin-5(2H)-acetyl]-3,3-dimethylpiperidine M.p.=228° C.

$^1$H NMR ($CDCl_3$) δ7.60 (d, 1H), 7.38 (m, 2H), 7.20 (m, 3H), 7.0 (m, 2H), 6.72 (m, 1H), 6.4 (m, 1H), 5.0 (m, 1H), 4.20 (m, 1H), 3.75 (m, 1H), 3.45 (m, 2H), 3.25 (m, 2H), 3.0 (m, 2H), 2.2 (s, 3H), 1.3–1.6 (m, 4H), 0.95 (s, 3H), 0.90 (s, 3H).

Mass spectrum: m/e=480.21339.

EXAMPLE 61

(R)-1-[3,4-Dihydro-4-oxo-3-[[(3-methylphenylamino)carbonyl]amino]-1,5-benzothiazepin-5(2H)-acetyl]-3,3-dimethylpiperidine $^1$H NMR ($CDCl_3$) δ6.60–7.68 (m, 10H), 5.00–5.14 (m, 1H), 4.68–4.83 (m, 1H), 4.05–4.32 (m, 1H), 3.60–3.80 (m, 2H), 2.90–3.36 (m, 4H), 2.10–2.20 (m, 3H), 1.30–1.65 (m, 4H).

EXAMPLE 62

(S)-1-[3,4-Dihydro-4-oxo-3-[[(3-methylphenylamino)carbonyl]amino]-1,5-benzothiazepin-5(2H)-acetyl]-3,3-dimethylpiperidine $^1$H NMR ($CDCl_3$) δ6.60–7.68 (m, 10H), 5.00–5.14 (m, 1H), 4.68–4.83 (m, 1H), 4.05–4.32 (m, 1H), 3.60–3.80 (m, 2H), 2.90–3.36 (m, 4H), 2.10–2.20 (m, 3H), 1.30–1.65 (m, 4H), 0.80–1.00 (m, 6H).

EXAMPLE 63

(S)-1-[3,4-Dihydro-4-oxo-3-[[(3-methylphenylamino)carbonyl]amino]-1,5-benzothiazepin-5(2H)-acetyl]-4,4-tetramethylenepiperidine $^1$H NMR ($CDCl_3$) δ6.52–7.70 (m, 10H), 5.03 (d, 1H), 4.65–4.78 (m, 1H), 4.20 (d, 1H), 3.70–3.83 (m, 1H), 3.25–3.58 (m, 4H), 3.10 (t, 1H), 2.19 (s, 3H), 1.25–1.67 (m, 12H).

EXAMPLE 64

(R,S)-1-[3,4-Dihydro-4-oxo-3-[[(3-methylphenylamino)carbonyl]amino]-1,5-benzothiazepin-5(2H)-acetyl]-4,4-ethylenedioxylpiperidine M.p.=214°–216° C.

$^1$H NMR ($D_6DMSO$) δ8.95 (s, 1H), 7.75 (d, 1H), 7.62 (m, 1H), 7.45 (m, 2H), 7.25 (s, 1H), 7.15 (m, 2H), 6.75 (m, 2H), 5.20 (d, 1H), 4.55 (m, 1H), 4.35 (d, 1H), 4.02 (s, 4H), 3.65 (m, 5H), 3.02 (m, 1H), 2.25 (s, 3H), 1.6–1.9 (m, 4H).

Mass spectrum (fab): m/e=511 (P +1).

EXAMPLE 65

(R,S) -1-[3,4-Dihydro-4-oxo-3-[[(3-methylphenylamino)carbonyl]amino]-1,5-benzothiazepin-5(2H)-acetyl]-4-phenylpiperidine M.p.=234°–236° C.

$^1$H NMR ($D_6DMSO$) δ8.72 (s, 1H), 7.68 (d, 1H), 7.55 (m, 1H), 7.0–7.48 (m, 10H), 6.68 (m, 2H), 5.10 (m, 1H), 4.5 (m, 2H), 4.38 (m, 1H), 4.02 (m, 1H), 3.60 (m, 1H), 3.20 (m, 1H), 2.97 (m, 1H), 2.75 (m, 2H), 2.20 (s, 3H), 1.4–1.9 (m 4H).

Mass Spectrum (lab): m/e=529 (p+1).

EXAMPLE 66

(R,S)-1-[3,4-Dihydro-4-oxo-3-[[(3-methylphenylamino)carbonyl]amino]-1,5-benzothiazepin-5(2H)-acetyl]-3,5-dimethylpiperidine M.p.=241°–242° C.

$^1$H NMR ($CDCl_3$) δ7.60 (d, 1H), 7.40 (m, 2H), 7.08 (m, 2H), 6.9 (m, 1H), 6.82 (d, 1H), 6.25 (m, 1H), 5.07 (m, 1H), 4.72 (m, 1H), 4.55 (d, 1H), 4.15 (m, 1H), 3.87 (m, 1H), 3.60 (m, 1H), 3.0 (m, 1H), 2.20 (s, 3H), 0.7–2.2 (m, 12H).

Mass spectrum: m/e=480.21613.

EXAMPLE 67

(R,S)-1-[3,4-Dihydro-4-oxo-3-[[(3-methylphenylamino)carbonyl]amino]-1,5-benzothiazepin-5(2H)-acetyl]-1,3,4,5,6,7,8-octahydroisoquinoline M.p.=125° C.

$^1$H NMR ($D_6DMSO$) δ8.15 (s, 1H), 6.6–7.6 (m, 9H), 3.5–5.5 (m, 9H), 2.5–3.1 (m, 2H), 2.20 (s, 3H), 0.6–1.9 (10H).

Mass spectrum: m/e=506.22422.

EXAMPLE 68

(R,S)-1-[3,4-Dihydro-4-oxo-3-[[(3-methylphenylamino)carbonyl]amino]-1,5-benzothiazepin-5(2H)-acetyl]-3,3-tetramethylenepiperidine $^1$H NMR (CDCl$_3$) δ7.65 (d, 1H), 7.42 (m, 2H), 7.25 (m, 3H), 7.02 (m, 2H), 6.75 (t, 1H), 6.50 (m, 1H), 5.02 (m, 1H), 4.75 (m, 1H), 4.20 (m, 1H), 3.78 (m, 1H), 3.60 (m, 1H), 3.35 (m, 2H), 3.12 (m, 3H), 2.25 (s, 3H), 1.0–1.8 (m, 14H).

Mass spectrum: m/e=506.24259.

EXAMPLE 69

(R,S)-1-[3,4-Dihydro-4-oxo-3-[[(3-methylphenylamino)carbonyl]amino]-1,5-benzothiazepin-5(2H)-acetyl]-4,4-pentamethylenepiperidine $^1$H NMR (CDCl$_3$) δ7.65 (d, 1H), 7.40 (m, 2H), 6.9–7.3 (m, 5H), 6.80 (d, 1H), 6.25 (d, 1H), 5.05 (d, 1H), 4.75 (m, 1H), 4.15 (d, 1H), 3.90 (m, 1H), 3.52 (m, 2H), 3.38 (m, 2H), 3.0 (t, 1H), 2.28 (s, 3H), 1.3–1.6 (m, 14H).

Mass spectrum (lab): m/e=521 (p+1).

EXAMPLE 70

(R,S)-1-[3,4-Dihydro-4-oxo-3-[[(3-methylphenylamino)carbonyl]amino]-1,5-benzothiazepin-5(2H) -acetyl]-3,3pentamethylenepiperidine $^1$H NMR (CDCl$_3$) δ6.52–7.70 (m, 10H), 5.00 (t, 1H), 4.67–4.82 (m, 1H), 4.25 (t, 1H), 3.70–3.80 (m, 1H), 2.93–3.61 (m, 5H), 2.19 (m, 3H), 1.10–1.60 (m, 14H).

EXAMPLE 71

(R,S)-N-(1,1-Dimethylethyl)-3,4-dihydro-4-oxo-3-[[(3-methoxyphenylamino)carbonyl]-amino]-1,5-benzothiazepine -5(2H)-acetamide M.p.=230° C., 40% yield.

$^1$H NMR (D$_6$DMSO) δ8.84 (s, 1H), 7.72 (d, 1H), 7.54 (m, 2H), 7.48 (m, 1H), 7.36 (m, 1H), 7.08 (m, 2H), 6.74 (m, 2H), 6.50 (d, 1H), 4.65 (d, 1H), 4.40 (m, 1H), 4.00 (d, 1H), 3.68 (s, 3H), 3.60 (m, 1H), 3.00 (t, 1H), 1.28 (s, 6H).

EXAMPLE 72

(R,S)-N-(1,1-Dimethylethyl)-N-(benzyl)-3,4-dihydro-4-oxo-3-[[(3,-methoxyphenylamino)-carbonyl]amino]-1,5-benzothiazepine-5(2H)-acetamide M.p.=185° C.

$^1$H NMR (CDCl$_3$) δ8.9 (s, 1H), 7.6–7.75 (m, 2H), 7.25–7.55 (m ,7H), 7.10 (m, 2H), 6.80 (m, 2H), 6.48 (d, 1H), 4.9 (d, 1H), 4.45 (m, 1H), 4.20 (d, 1H), 3.65 (s, 3H), 3.60 (m, 1H), 3.35 (m, 2H), 2.90 (m, 1H), 1.40 (s, 9H).

Mass spectrum: m/e=546.22427.

EXAMPLE 73

(R,S)-N-(1,1-Dimethylethyl)-N-(methyl)-3,4-dihydro-4-oxo-3-[[(3-methoxyphenylamino)carbonyl]amino]-1,5-benzothiazepine-5(2H)-acetamide M.p.=160° C.

$^1$H NMR (CDCl$_3$) δ8.85 (s, 1H), 7.67 (d, 1H), 7.52 (m, 1H), 7.30 (m, 2H), 7.07 (m, 2H), 6.70 (m, 2H), 6.45 (d, 1H), 4.98 (d, 1H), 4.47 (m, 1H), 4.16 (d, 1H), 3.65 (s, 3H), 3.60 (m, 1H), 2.93 (m, 1H), 2.89 (s, 3H), 1.40 (s, 9H).

Mass Spectrum: m/e=470.19553.

EXAMPLE 74

(R,S)-4-[3,4-Dihydro-4-oxo-3-[[(3-methoxyphenylamino)carbonyl]amino]-1,5-benzothiazepin-5(2H)-acetyl]-morpholine M.p.=145° C.

$^1$H NMR (CDCl$_3$) δ7.62 (d, 1H), 7.4 (m, 2H), 7.22 (m, 2H), 7.05 (m, 2H), 6.70 (d, 1H), 6.50 (d, 1H), 6.32 (d, 1H), 4.98 (d, 1H), 4.70 (m, 1H), 4.10 (d, 1H), 3.80 (m, 1H), 3.70 (s, 3H), 3.4–3.65 (m, 8H), 3.0 (t, 1H).

EXAMPLE 75

(R,S)-N,N-(1-Methylethyl)-3,4-dihydro-4-oxo-3-[[(3-methoxyphenylamino)carbonyl]amino]-1,5-benzothiazepine-5(2H)-acetamide M.p.=243° C. $^1$H NMR (CDCl$_3$) δ7.6 (d, 1H), 7.4 (m, 2H), 7.2 (m, 2H), 7.03 (m, 2H), 6.70 (d, 1H), 6.45 (d, 1H), 6.35 (d, 1H), 5.08 (d, 1H), 4.65 (m, 1H), 4.0 (d, 1H), 3.80 (m, 3H), 3.68 (s, 3H), 3.0 (t, 1H), 1.05–1.45 (m, 12H).

EXAMPLE 76

(R)-N,N-(1-Methylethyl)-3,4-dihydro-4-oxo-3-[[(3-methoxyphenylamino)carbonyl]amino]-1,5-benzothiazepine-5(2H)-acetamide $^1$H NMR (CDCl$_3$) δ6.38–7.66 (m, 10H), 5.10 (d, 1H), 4.70–4.80 (m, 1H), 4.09 (d, 1H), 3.85–3.96 (m, 1H), 3.68–3.78 (m, 1H), 3.59 (s, 3H), 3.47–3.64 (m, 1H), 3.00 (t, 1H), 1.10–1.42 (m, 12H).

EXAMPLE 77

(R,S)-1-[3,4-Dihydro-4-oxo-3-[[(3-methoxyphenylamino)carbonyl]amino]-1,5-benzothiazepin-5(2H)-acetyl]-3,3-dimethylpiperidine $^1$H NMR (CDCl$_3$) δ7.65 (m,2H), 7.40 (m, 2H), 7.20 (m, 1H), 7.10 (m, 1H), 6.95 (m, 1H), 6.7 (m, 1H), 6.65 (m, 1H), 6.45 (m, 1H), 505 (m, 1H), 4.75 (m, 1H), 4.05–4.3 (m, 1H), 3.75 (m, 1H), 3.68 (s, 3H), 3.55 (s, 1H), 2.9–3.4 (m, 5H), 1.3–1.6 (m, 4), 0.8–0.95 (m, 6H).

EXAMPLE 78

(R)-1-[3,4-Dihydro-4-oxo-3-[[(3-methoxyphenylamino)carbonyl]amino]-1,5-benzothiazepin-5(2H)-acetyl]-3,3-dimethylpiperidine $^1$H NMR (CDCl$_3$) δ6.35–7.70 (m, 10H), 5.01–5.13 (m, 1H), 4.70–4.83 (m, 1H), 4.05–4.28 (m, 1H), 3.61 (s, 3H), 2.90–3.80 (m, 6H), 1.30–1.69 (m, 4H), 0.80–1.00 (m, 6H).

EXAMPLE 79

(S)-1-[3,4-Dihydro-4-oxo-3-[[(3-methoxyphenylamino)carbonyl]amino]-1,5-benzothiazepin-5(2H)-acetyl]-3,3-dimethylpiperidine $^1$H NMR (CDCl$_3$) δ6.35–7.70 (m, 10H), 5.01–5.13 (m, 1H), 4.70–4.83 (m, 1H), 4.05–4.28 (m, 1H), 3.61 (s, 3H), 2.90–3.8 (m, 6H), 1.30–1.69 (m, 4H), 0.80–1.00 (m, 6H).

EXAMPLE 80

(R,S)-1-[3,4-dihydro-4-oxo-3-[[(3-methoxyphenylamino)carbonyl]amino]-1,5-benzothiazepin-5(2H)-acetyl]-4-(2-hydroxyethyl)piperidine M.p.=147° C. (decomp.).

$^1$H NMR (CDCl$_3$) δ7.62 (m, 1H), 7.57 (m, 1H), 7.48 (m, 2H), 7.22 (m, 2H), 7.05 (m, 2H), 6.75 (d, 1H), 6.48 (d, 1H), 5.05 (t, 1H), 4.75 (m, 1H), 4.55 (m, 1H), 4.0–4.3 (m, 2H), 3.80 (m, 3H), 3.72 (s, 3H), 3.0 (m, 2H), 2.58 (m, 1H), 2.05 (s, 1H), 1.4–1.85 (m, 5H), 1.1–1.4 (m, 2H).
Mass Spectrum (fab): m/e=513 (p+1).

EXAMPLE 81

(R,S)-1-[3,4-Dihydro-4-oxo-3-[[(3-methoxyphenylamino)carbonyl]amino]-1,5-benzothiazepin-5(2H)-acetyl]-4-(methylenephenyl)piperidine
M.p.=223°–225° C.
$^1$H NMR (CDCl$_3$) δ7.65 (d, 1H), 7.45 (m, 3H), 7.0–7.35 (m, 8H), 6,75 (d, 1H), 6.5 (m, 2H), 5.05 (m, 1H), 4.75 (m, 1H), 4.55 (m, 1H), 4.28 (m, 1H), 3.82 (m, 2H), 3.72 (s, 3H), 2.85–3.15 (m, 2H), 2.55 (m, 3H), 1.4–1.8 (m, 4H), 1.10 (m, 1H).
Mass spectrum (fab): m/e=559 (P+1).

EXAMPLE 82

(R,S)-1-[3,4-Dihydro-4-oxo-3-[[(3-methoxyphenylamino)carbonyl]amino]-1,5-benzothiazepin-5(2H)-acetyl]-4-(3-phenylpropyl)piperidine
M.p.=201° C.
$^1$H NMR (CDCl$_3$) δ7.62 (d, 1H), 7.50 (m, 1H), 7.40 (m, 2H), 6.95–7.35 (m, 8H), 6.75 (d, 1H), 6.50 (m, 2H), 5.05 (m, 1H), 4.80 (m, 1H), 4.52 (m, 1H), 4.18 (m, 1H), 3.80 (m, 2H), 3.72 (s, 3H), 2.9–3.2 (m, 2H), 2.60 (m, 3H), 0.9–1.9 (m, 9H).
Mass spectrum (fab): m/e=587 (P+1).

EXAMPLE 83

(R,S)-1-[3,4-Dihydro-4-oxo-3-[[(3-methoxyphenylamino)carbonyl]amino]-1,5-benzothiazepin-5(2H)-acetyl]-2,6-dimethylpiperidine
M.p.=167° C.
$^1$H NMR (D$_6$DMSO) δ8.82 (s, 1H), 7.67 (d, 1H), 7.55 (m, 1H), 7.40 (m, 2H), 7.08 (m, 2H), 6.70 (m, 2H), 6.45 (d, 1H), 4.9–5.25 (m, 1H), 3.9–4.6 (m, 4H), 3.65 (s, 3H), 3.62 (m, 1H), 2.95 (m, 1H), 1.0–1.6 (m, 12H).
Mass spectrum: m/e=496.21078.

EXAMPLE 84

(R,S)-1-[3,4-Dihydro-4-oxo-3-[[(3-methoxyphenylamino)carbonyl]amino]-1,5-benzothiazepin-5(2H)-acetyl]-2-methylpiperidine
M.p.=160° C.
$^1$H NMR (D$_6$DMSO) δ8.82 (d, 1H), 7.68 (d, 1H), 7.58 (m, 1H), 7.32 (m, 2H), 7.08 (m, 2H), 6.8 (m, 2H), 6.45 (d, 1H), 5.05 (d, 1H), 4.05–4.8 (m, 4H), 3.65 (s, 3H), 3.60 (m, 1H), 3.35 (m, 1H), 2.95 (m, 1H), 1.0–1.9 (m, 9H),
Mass spectrum: m/e=482.19472.

EXAMPLE 85

(R,S)-1-[3,4-Dihydro-4-oxo-3-[[(3-methoxyphenylamino)carbonyl]amino]-1,5-benzothiazepin-5(2H)-acetyl]-4,4-dimethylpiperidine
M.p.=228° C.
$^1$H NMR (D$_6$DMSO) δ8.82 (s, 1H), 7.70 (d, 1H), 7.52 (t, 1H), 7.38 (m, 2H), 7.08 (m, 2H), 6.70 (m, 2H), 6.44 (d, 1H), 5.06 (d, 1H), 4.42(m, 1H), 4.20 (d, 1H), 3.68 (s, 3H), 3.24–3.80 (m, 5H), 1.20–1.40 (m, 4H), 0.96 (s, 3H).
Mass spectrum: m/e=496.21152.

EXAMPLE 86

(R,S)-1-[3,4-Dihydro-4-oxo-3-[[(3-methoxyphenylamino)carbonyl]amino]-1,5-benzothiazepin-5(2H)-acetyl]-4,4-tetramethylene piperidine
M.p.=232°–233° C.
$^1$H NMR (D$_6$DMSO) δ8.80 (s, 1H), 7.66 (d, 1H), 7.50 (m, 1H), 7.30 (m, 2H), 7.05 (m, 2H), 6.90 (m, 2H), 6.42 (d, 1H), 5.05 (d, 1H), 4.42 (m, 1H), 4.20 (d, 1H), 3.66 (s, 3H), 3.20–3.80 (m, 5H), 2.92 (t, 1H), 1.20–1.80 (m, 12H).
Mass spectrum: m/e=522.24349.

EXAMPLE 87

(R,S)-N,N-(1-Methylethyl)-3,4-dihydro-4-oxo-3-[[(3-chlorophenylamino)carbonyl]amino]-1,5-benzothiazepine-5(2H)- acetamide
$^1$H NMR (CDCl$_3$) δ7.65 (d, 1H), 7.45 (m, 3H), 7.25 (m, 2H), 7.13 (d, 1H), 7.05 (m, 1H), 6.85 (m, 1H), 6.50 (m, 1H), 5.20 (d, 1H), 4.72 (m, 1H), 4.05 (d, 1H), 3.90 (m, 1H), 3.75 (m, 1H), 3.62 (m, 1H), 3.05 (m, 1H), 1.2–1.4 (m, 2H).
Mass spectrum: m/e=488 (P).

EXAMPLE 88

(R)-N,N-(1-Methylethyl)-3,4-dihydro-4-oxo-3-[[(3-chlorophenylamino)carbonyl]amino]-1,5-benzothiazepine-5(2H)-acetamide
$^1$H NMR (CDCl$_3$) δ6.70–7.90 (m, 10H), 5.15 (d, 1H), 4.69–4.82 (m, 1H), 4.04 (d, 1H), 3.82–3.96 (m, 1H), 3.50–3.70 (m, 2H), 3.03 (t, 1H), 1.12–1.50 (m, 12H).

EXAMPLE 89

(R,S)-1-[3,4-Dihydro-4-oxo-3-[[(3-chlorophenylamino)carbonyl]amino]1,5-benzothiazepin-5(2H)-acetyl]-3,3-dimethylpiperidine
$^1$H NMR (CDCl$_3$) δ7.60 (d, 1H), 7.35 (m, 3H), 7.15 (m, 2H), 7.0 (m, 2H), 6.80 (m, 1H), 6.56 (m, 1H), 5.05 (d, 1H), 4.65 (m, 1H), 4.0–4.3 (m, 1H), 3.60 (m, 2H), 3.26 (m, 1H), 2.8–3.2 (m, 3H), 1.3–1.6 (m, 4H), 0.6–1.0 (m, 6H).
Mass spectrum (fab): m/e=501 (P+1).

EXAMPLE 90

(R)-1-[3,4-Dihydro-4-oxo-3-[[(3-chlorophenylamino)carbonyl]amino]-1,5-benzothiazepin-5(2H) -acetyl]-3,3-dimethylpiperidine
$^1$H NMR (CDCl$_3$) δ6.70–7.78 (m, 10H), 5.10–5.22 (m, 1H), 4.70–4.83 (m, 1H), 4.00–4.25 (m, 1H), 2.90–3.82 (m, 6H), 1.30–1.70 (m, 4H), 0.80–1.10 (m, 6H).

EXAMPLE 91

(S)-1-[3,4-Dihydro-4-oxo-3-[[(3-chlorophenylamino)carbonyl]amino]-1,5-benzothiazepin-5(2H)-acetyl]-3,3-dimethyl piperidine
$^1$H NMR (CDCl$_3$) δ6.70–7.78 (m, 10H), 5.10–5.22 (m, 1H), 4.70–4.83 (m, 1H), 4.00–4.25 (m, 1H), 2.90–3.82 (m, 6H), 1.30–1.70 (m, 4H), 0.80–1.10 (m, 6H).

EXAMPLE 91(a)

3-(S)-2-[4-Oxo-3-(3-m-tolyl-ureido)-3,4-dihydro-2H-benzo[b]-[1,4]-thiazepin-5-yl]N-thiochroman-4-yl-acetamide
$^1$H NMR (CDCl$_3$) δ7.6–7.85 (m, 2H), 7.37–7.5 (m, 2H), 7.06–7.32 (m, 7H), 6.88–7.0 (m, 2H), 6.75–6.85 (m, 2H), 4.85–5.15 (m, 2H), 4.58 (m, 1H), 4.25 (m, 1H), 3.65 (m, 1H), 2.82 (m, 1H), 2.50 (m, 1H), 2.25 (s, 3H), 1.95 (m, 1H), 1.22 (m, 2H).
Mass spectrum: m/e=532.15153±0.38 ppm.

EXAMPLE 91(b)

3-(S)-1-[4-Oxo -5-(2-oxo-2-{4-[4-(3-phenoxy-phenyl-but-3-enyl]-piperazin-1-yl}ethyl)-2,3,4,5-tetrahydro-benzyl[b]-[1,4]-thiazepin-3-yl]-m-tolyl-urea $^1$H NMR (CDCl$_3$) δ6.35–7.8 (m, 20H), 5.62 (m, 1H), 5.02 (d, 1H), 4.72 (m, 1H), 4.15 (d, 1H), 3.75 (m, 1H), 3.3–3.7 (m, 4H), 3.05 (t, 1H), 2.2–2.55 (m, 9H), 2.15 (s, 3).

Mass spectrum: m/e=676.28938±9.42 ppm.

EXAMPLE 92

(R,S)-3,4-Dihydro-4-oxo-3-[[(3-methylphenylamino)carbonyl]amino]-1,5-benzothiazepine-5(2H)-acetic acid-1,1-dimethylethyl ester, 1-alpha-oxide A mixture of 200 mg (0.45 mM) of 3,4-dihydro-4-oxo-3-[[(3-methylphenylamino)carbonyl]amino]-1,5-benzothiazepine-5(2H)-acetic acid-1,1-dimethylethyl ester and 232 mg (1.08 mM) of sodium periodate was heated to 60° C. In 40 mL of methanol and 15 mL of water (H$_2$O) for 5 hours. The mixture was cooled to room temperature and stirred an additional 16 hours. The solvent was evaporated, and the residue was triturated with 25 mL of H$_2$O. This mixture was extracted with ethyl acetate. The ethyl acetate extracts were dried (Na$_2$SO$_4$) and concentrated to yield 214 mg of an amorphous solid. The residue was chromatographed on 16 g of silica using 4:1 ethyl acetate:hexanes as the eluant. Appropriate fractions were combined to yield 75 mg of the α-sulfoxide. rF (4:1 ethyl acetate:hexanes)=0.62.

$^1$H NMR (CDCl$_3$) δ7.90 (m, 1H), 7.58 (m, 2H), 7.30 (m, 2H), 7.04–7.2 (m, 3H), 6.95 (d, 1H), 6.8 (d, 1H), 6.25 (m, 1H), 4.75 (m, 1H), 4.4 (m, 2H), 3.85 (m, 1H), 3.60 (m, 1H), 2.24 (s, 3H), 1.40 (s, 9H).

Mass Spectrum: m/e=458.2 (p+1).

EXAMPLE 92(a)

(R,S)-3,4-Dihydro-4-oxo-3-[[(3-methylphenylamino)carbonyl]amino]-1,5-benzothiazepine-5(2H)-acetic acid-1,1-dimethylethyl ester, 1-beta-oxide Continued elution of the product from Example 92 yielded 105 mg of the β-sulfoxide. rF (4:1 ethyl acetate:hexanes)=0.45.

$^1$H NMR (CDCl$_3$) δ8.04 (d, 1H), 4.78 (m, 1H), 4.60 (m, 3H), 7.14 (m, 2H), 6.98 (d, 1H), 6.85 (d, 1H), 6.38 (d, 1H), 4.90 (m, 2H), 4.20 (m, 1H), 3.80 (m, 1H), 3.60 (m, 1H), 2.28 (s, 3H), 1.50 (s, 9H).

Mass Spectrum: m/e=458.2 (p+1).

EXAMPLE 93

(R,S)-3,4-Dihydro-4-oxo-3-[[(3-methylphenylamino)carbonyl]amino]-1,5-benzothiazepine-5(2H)-acetic acid-1,1-dimethylethyl ester, 1,1-dioxide To a solution of 50 mg (0.113 mM) of 3,4-dihydro-4-oxo-3-[[(3methylphenylamino)carbonyl]amino]-1,5-benzothiazepine-5(2H)-acetic acid-1,1-dimethylethyl ester in 1 mL of acetic acid was added 0.115 mL (0.113 mM) of 30% hydrogen peroxide and the mixture was stirred at room temperature for 3 days. To the mixture was added 5 mL of H$_2$O. The resulting precipitate was collected via filtration. The residue was chromatographed on silica using 4:1 ethyl acetate:hexanes as the eluant. Appropriate fractions were combined to yield 22 mg of product as an amorphous solid. rF (95:5 CHCl$_3$:acetone)=0.20.

$^1$H NMR (CDCl$_3$) δ8.05 (d, 1H), 7.78 (m, 1H), 7.60 (m, 2H), 7.10 (m, 3H), 6.95 (d, 1H), 6.82 (d, 1H), 6.35 (d, 1H), 4.85 (m, 2H), 4.16–4.3 (m, 1H), 3.78 (m, 1H), 3.60 (m. 1H), 2.25 (s, 3H), 1.40 (s, 9H).

Mass Spectrum: m/e=473.16558.

The title compounds of Examples 94–104 were prepared using procedures similar to that of Example 93.

EXAMPLE 94

(R,S)-N,N-(1-Methylethyl)-3,4-dihydro-4-oxo-3-[[(3-methylphenylamino)carbonyl]amino]-1,5-benzothiazepine-5(2H)-acetamide-1,1-dioxide $^1$H NMR (CDCl$_3$) δ8.05 (d, 1H), 7.75 (d, 2H), 7.55 (m, 1H), 7.12 (m, 2H), 6.95 (d, 1H), 6.85 (d, 1H), 6.68 (s, 1H), 6.12 (d, 1H), 5.20 (d, 1H), 4.80 (m, 1H), 4.28 (m, 1H), 3.87 (m, 1H), 3.75 (d, 1H), 3.55 (m, 2H), 2.28 (s, 3H), 1.40 (m, 6H), 1.35 (m, 6H).

Mass spectrum: m/e=500.20090.

EXAMPLE 95

(R)-N,N-(1-Methylethyl)-3,4-dihydro-4-oxo-3-[[(3-methylphenylamino)carbonyl]amino]-1,5-benzothiazepine-5(2H)-acetamide-1,1-dioxide $^1$H NMR (CDCl$_3$) δ6.30–8.05 (m, 10H), 4.70–5.24 (m, 2H), 3.40–4.25 (m, 5H), 2.22 (s, 3H), 1.10–1.51 (m, 12H).

EXAMPLE 96

(R,S)-1-[3,4-Dihydro-4-oxo-3-[[(3-methylphenylamino)carbonyl]amino]-1,5-benzothiazepin-5(2H)-acetyl]-3,3-dimethylpiperidine-1,1-dioxide $^1$H NMR (CDCl$_3$) δ8.02 (d, 1H), 7.68 (m, 2H), 7.50 (m, 1H), 7.04 (m, 4H), 6.75 (d, 1H), 6.25 (d, 1H), 5.20 (m, 1H), 4.85 (m, 1H), 4.25 (m, 1H), 3.4–3.9 (m, 3H), 3.30 (m, 2H), 3.0 (s, 1H), 2.25 (s, 3H), 1.1–1.9 (m, 4H), 0.9 (m, 6H).

Mass spectrum: m/e=512.20561.

EXAMPLE 97

(R)-1-[3,4-Dihydro-4-oxo-3-[[(3-methylphenylamino)carbonyl]amino]1,5-benzothiazepin-5(2H)-acetyl]-3,3-dimethylpiperidine-1,1-dioxide $^1$H NMR (CDCl$_3$) δ6.43–8.07 (m, 10H), 5.10–5.24 (m, 1H), 4.78–4.95 (m, 1H), 2.90–4.22 (m, 7H), 2.19 (s, 3H), 1.30–1.70 (m, 4H), 0.80–1.03 (m, 6H).

EXAMPLE 98

(S)-1-[3,4-Dihydro-4-oxo-3-[[(3-methylphenylamino)carbonyl]amino]-1,5-benzothiazepin-5(2H)-acetyl]-3,3-dimethylpiperidine-1,1-dioxide $^1$H NMR (CDCl$_3$) δ6.43–8.07 (m, 10H), 5.10–5.24 (m, 1H), 4.78–4.95 (m, 1H), 2.90–4.22 (m, 7H), 2.19 (s, 3H), 1.30–1.70 (m, 4H), 0.80–1.03 (m, 6H).

EXAMPLE 99

(R)-N,N-(1-Methylethyl)-3,4-dihydro-4-oxo-3-[[(3-methoxyphenylamino)carbonyl]amino]-5-benzothiazepine-5(2H)-acetamide-1,1-dioxide $^1$H NMR (CDCl$_3$) δ6.80–8.08 (m, 10H), 5.00–5.20 (m, 1H), 4.68–4.80 (m, 1H), 3.30–4.49 (m, 8H), 0.90–1.50 (m, 12H).

EXAMPLE 100

(R)-1-[3,4-Dihydro-4-oxo-3-[[(3-methoxyphenylamino)carbonyl]amino]-1,5-benzothiazepin-5(2H)-acetyl]-3,3-dimethylpiperidine-1,1-dioxide $^1$H NMR (CDCl$_3$) δ6.44–8.05 (m, 10H), 5.07–5.25 (m, 1H), 4.80–4.95 (m, 1H), 3.65 (s, 3H), 2.85–4.23 (m, 7H), 1.30–1.70 (m, 4H), 0.80–1.04 (m, 6H).

EXAMPLE 101

(S)-1-[3,4-Dihydro-4-oxo-3-[[(3-methoxyphenylamino)carbonyl]amino]-1,5-benzothiazepin-5(2H)-acetyl]-3,3-dimethylpiperidine-1,1-dioxide $^1$H NMR (CDCl$_3$) δ6.44–8.05 (m, 10H), 5.07–5.25 (m, 1H), 4.80–4.95 (m, 1H), 3.65 (s, 3H), 2.85–4.23 (m, 7H), 1.30–1.70 (m, 4H), 0.80–1.04 (m, 6H).

EXAMPLE 102

(R)-N,N-(1-Methylethyl)-3,4-dihydro-4-oxo-3-[[(3-chlorophenylamino)carbonyl]amino]-1,5-benzothiazepine-5(2H)-acetamide-1,1-dioxide $^1$H NMR (CDCl$_3$) δ6.40–8.05 (m, 10H), 5.15–5.30 (d, 1H), 4.82–4.96 (m, 1H), 3.49–4.18 (m, 5H), 1.12–1.54 (m, 12H).

EXAMPLE 103

(R)-1-[3,4-Dihydro-4-oxo-3-[[(3-chlorophenylamino)carbonyl]amino]-1,5-benzothiazepin-5(2H)-acetyl]-3,3-dimethylpiperidine-1,1-dioxide $^1$H NMR (CDCl$_3$) δ6.62–8.06 (m, 10H), 5.10–5.26 (m, 1H), 4.84–4.98 (m, 1H), 2.90–4.15 (m, 7H), 1.30–1.72 (m, 4H), 0.78–1.03 (m, 6H).

EXAMPLE 104

(S)-1-[3,4-Dihydro-4-oxo-3-[[(3-chlorophenylamino)carbonyl]amino]-1,5-benzothiazepin-5(2H)-acetyl]-3,3-dimethylpiperidine-1,1-dioxide $^1$H NMR (CDCl$_3$) δ6.62–8.06 (m, 10H), 5.10–5.26 (m, 1H), 4.84–4.98 (m, 1H), 2.90–4.15 (m, 7H), 1.30–1.72 (m, 4H), 0.78–1.03 (m, 6H).

EXAMPLE 105

(R)-1-{9-[2-(3,5-Dimethylpiperidin-1-yl)-2-oxo-ethyl]-8-oxo-6,7,8,9-tetrahydro-5-oxa-9-aza-benzocyclohepten-7-yl}-3-m-tolyl-urea A. O-(o-Nitrophenyl)-N-t-butoxycarbonyl-D-serine To a suspension of 1.84 g (0.0768M) of sodium hydride (NaH) in 50 mL of DMF at 0° C. under a nitrogen atmosphere was added dropwise a slurry of 7.39 g (0.0360M) of N-t-butoxycarbonyl-D-serine. After addition was complete, the reaction was warmed to room temperature and stirred for 45 minutes. The reaction was cooled to –5° C. and 4.04 mL (0.0384M) of 2-fluoronitrobenzene was added dropwise. The reaction was then warmed to room temperature and stirred for 1 hour. The reaction was quenched with an equal volume of water and extracted with ethyl acetate. The ethyl acetate extracts were reextracted with water (pH=9). The water layer was then adjusted to pH=7 and extracted with ethyl acetate. The water layer was then adjusted to pH=2 and extracted with ethyl acetate. The pH=2 ethyl acetate extracts were combined, dried, and evaporated to yield 8.98 g of product as an oil.

$^1$H NMR (CDCl$_3$) δ7.8 (d, 1H), 7.42 (t, 1H), 6.95 (m, 2H), 4.62 (m, 1H), 4.55 (d, 1H), 4.30 (d, 1H), 1.38 (s, 9H).

B. O-(o-Aminophenyl)-N-t-butoxycarbonyl-D-serine

A mixture of 8.98 g (0.0275M) of O-(o-nitrophenyl)-N-t-butoxycarbonyl-D-serine, 2.95 g (0.0551M) of ammonium chloride (NH$_4$Cl) and 25 g (0.3856M) of zinc dust in 200 mL of methanol was stirred at room temperature for 18 hours. The solvent was evaporated and the residue dissolved in 200 mL of a 50/50 mixture of ethyl acetate and chloroform. The mixture was filtered and the filtrate evaporated to yield 8.15 g (100%) of product as an oil.

$^1$H NMR (D$_6$DMSO) δ6.9 (d, 1H), 6.5–6.9 (m, 2H), 6.45 (t, 1H), 4.7 (m, 1H), 4.2–4.4 (m, 2H), 1.38 (s, 9H).

C. D-3-t-Butoxycarbonyl-amino-2,3-dihydro-1,5-benzoxazepin-4(5H)-one

A solution of 1.0 g (0.00337M) of O-(o-aminophenyl)-N-t-butoxycarbonyl-D-serine was dissolved in 5.6 mL of DMF and cooled to 0° C. under a nitrogen atmosphere. To this solution was added dropwise 0.654 mL (0.00432M) of diethyl cyanophosphonate. Stirring was continued at 0° C. for 5 minutes, at which time 0.327 mL (0.00236M) of triethylamine was added. The reaction mixture was stirred ½ hour at 0° C. and then warmed to room temperature. After 1 hour at room temperature, 6 mL of water was added, and the mixture stirred for an additional 16 hours. The resulting precipitate was filtered, washed with hexanes, and dried to yield 464 mg (50% yield) of product.

$^1$H NMR (D$_6$DMSO) δ7.0–7.1 (m, 4H), 4.3–4.4 (m, 3H), 1.3 (s, 9H).

D. D-3-Amino-2,3-dihydro-1,5-benzoxazepin-4(5H)-one

To 30 mL of ethyl acetate saturated with hydrogen chloride (HCl) gas was added 593 mg (0.00214M) of D-3-t-butoxycarbonyl-amino-2,3-dihydro-1,5-benzoxazepin-4(5H)-one. The mixture was stirred for 2 hours at room temperature, and evaporated to dryness. The residue was suspended in 25 mL of water and 25 mL of ethyl acetate, and the pH adjusted to 9.5. The organic layer was separated from the water, dried, and evaporated to yield 139 mg (37%) of product as a brown solid.

$^1$H NMR (CDCl$_3$) δ8.26 (s, 1H), 6.98–7.15 (m, 4H), 4.42 (m, 1H), 4.18 (t, 1H), 3.82 (m, 1H), 1.8 (br s, 2H).

E. (R)-(8-Oxo-6,7,8,9-tetrahydro-5-oxa-9-aza-benzocyclohepten-7yl)-3-m-tolyl-urea A solution of 0.64 g (0.00359M) of D-3-amino-2,3-dihydro-1,5-benzoxazepin-4-(5H)-one dissolved in 5 mL of methylene chloride was cooled to 0° C. under a nitrogen atmosphere. To this solution was added 0.046 mL (0.00359M) of m-tolyl isocyanate, and the reaction was stirred at ambient temperature for 2 hours. The solvent was evaporated and the resulting residue was triturated with ether. The resulting solids were filtered to yield 86 mg (77%) of product.

$^1$H NMR (CDCl$_3$) δ8.05 (br s, 1H), 7.95 (br s, 1H), 7.25 (d, 1H), 6.9–7.1 (m, 5H), 6.8 (m, 1H), 6.45 (m, 1H), 4.9 (m, 1H), 4.65 (m, 1H), 4.15 (1, 1H), 2.22 (s, 3H).

F. (R)-1-{9-[2-(3,5-Dimethylpiperidin-1-yl)-2-oxo-ethyl]-8-oxo-6,7,8,9-tetrahydro-5-oxa-9-aza-benzocyclohepten-7-yl}-3-m-tolyl-urea A solution of 0.100 g (0.000325M) (R)-(8-oxo-6,7,8,9-tetrahydro-5-oxa-9-aza-benzocyclohepten-7-yl)-3-m-tolyl-urea in 5 ml of THF was cooled to –78° C. under a nitrogen atmosphere. To this solution was added dropwise 0.321 mL (0.000325M) of lithium bis-hexamethyldisilylamide (1M solution in THF) and the reaction was stirred for 15 minutes. To this mixture was added 0.090 ml (0.000325M) of N-iodoacetyl-3,5-dimethyl piperidine. After addition was complete, the reaction was warmed to room temperature and stirred for 30 minutes. The reaction mixture was quenched with 5 mL of water, and extracted with ethyl acetate. The ethyl acetate extracts were dried and evaporated. The residue was chromatographed on 15 g of silica using 10:1 chloroform:methanol as the eluant. The appropriate fractions were combined and evaporated to yield 109 mg (72% yield) of product as a white solid.

$^1$H NMR (CDCl$_3$) δ7.5 (m, 1H), 7.1–7.3 (m, 5H), 6.98 (m, 2H), 6.75 (m, 1H), 6.45 (m, 1H), 5.0 (m, 2H), 4.7 (m, 1H), 4.2–4.5 (m, 3H), 3.6 (m, 1H), 3.9–3.7 (m, 3H), 2.2 (s, 3H), 0.7–1.9 (m, 10H).

Mass spectrum (fab) m/e=465 (p).

The title compounds of Examples 108–114 were prepared by a procedure similar to that of Example 105A.

EXAMPLE 108

O-(2-Nitro-4-methyl-phenyl)-N-t-butoxycarbonyl-D-serine $^1$H NMR (CDCl$_3$) δ7.65 (s, 1H), 7.32 (d, 1H), 6.95 (d, 1H), 5.58 (d, 1H), 4.72 (d, 1H), 4.60 (m, 1H), 4.32 (m, 1H), 2.35 (s, 3H), 1.45 (s, 9H).

EXAMPLE 109

O-(2-Nitro-4-fluoro-phenyl)-N-t-butoxycarbonyl-D-serine $^1$H NMR (CDCl$_3$) δ7.62 (m, 1H), 7.30 (m, 1H), 7.05 (m, 1H), 5.65 (d, 1H), 4.77 (m, 1H) 4.62 (m, 1H), 4.45 (m, 1H), 1.40 (s, 9H).

EXAMPLE 110

O-(2-Nitro-5-methyl-phenyl)-N-t-butoxycarbonyl-D-serine $^1$H NMR (CDCl$_3$) δ7.76 (d, 1H), 6.90 (s, 1H), 6.85 (d, 1H), 5.72 (d, 1H), 4.75 (m, 1H), 4.62 (m, 1H), 4.38 (m, 1H), 2.40 (s, 3H), 1.48 (s, 9H).

EXAMPLE 111

O-(2-Nitro-5-fluoro-phenyl)-N-t-butoxycarbonyl-D-serine $^1$H NMR (CDCl$_3$) δ8.0 (m, 1H), 6.75 (m, 2H), 5.6 (m, 1H), 4.70 (m, 1H), 4.5 (m, 1H), 4.32 (m, 1H), 1.45 (s, 9H).

EXAMPLE 112

O-(2Nitro-phenyl)-N-t-butoxycarbonyl-D-threonine $^1$H NMR (CDCl$_3$) δ7.4–8.5 (m, 3H), 5.55 (m, 1H), 5.22 (m, 1H), 4.60 (m, 1H), 1,40 (m, 12H).

EXAMPLE 113

O-(2-Nitro-4-fluoro-phenyl)-N-t-butoxycarbonyl-D-threonine $^1$H NMR (CDCl$_3$) δ7.0–7.9 (m, 3H), 5.5 (m, 1H) 5.15 (m, 1H), 4.55 (m, 1H), 1.40 (m, 12H).

Mass spectrum: m/e=358.11705±1.61 ppm.

EXAMPLE 114

O-(2-Nitro-5-fluoro-phenyl)-N-t-butoxycarbonyl-D-threonine $^1$H NMR (CDCl$_3$) δ7.92 (m, 1H), 6.6–6.8 (m, 2H), 5.6 (m, 1H), 4.62 (m, 1H), 4.25 (m, 1H), 1.40 (s, 3H), 1.20 (d, 1H).

Mass spectrum: m/e=358.11882±3.33 ppm.

The title compounds of Examples 115 and 116 were prepared by a procedure similar to that of Example 105B.

EXAMPLE 115

O-(2-Amino-4-fluoro-phenyl)-N-t-butoxycarbonyl-D-serine $^1$H NMR (D$_6$DMSO) δ6.1–7.0 (m, 3H), 5.1 (m, 1H), 4.0–4.4 (m, 2H), 3.5 (m, 2H), 1.40 (s, 9H).

EXAMPLE 116

O-(2-Amino-5-fluoro-phenyl) -N-t-butoxycarbonyl-D-serine $^1$H NMR (D$_6$DMSO) δ6.55–7.0 (m, 3H), 4.60 (bs, 2H), 4.0–4.4 (m, 3H), 1.35 (s, 9H).

A procedure for reducing the nitro group that is an alternative to that of Example 105B is illustrated below in Example 117.

EXAMPLE 117

O-(2-Amino-phenyl)-N-t-butoxycarbonyl-D-threonine

A mixture of 6.0 g (0.0176M) of 0-(2-Nitro-phenyl)-N-t-butoxycarbonyl-D-threonine, 2.94 mL (0.02112M) of triethylamine and 600 mG of 10% palladium on carbon in 200 mL of ethanol was hydrogenated at room temperature at 50 psi for 1.5 h. The mixture was filtered and the solvent evaporated to yield 4.30 g (74%) of product as an oil. $^1$H NMR (CDCl$_3$) δ6.6–7.0 (m, 4H), 4.90 (m, 1H), 4.2–4.4 (m, 1H), 1.40 (m, 12H). Mass spectrum: m/e=310.15303±0.51 ppm.

The title compounds of Examples 118 to 121 were prepared by a procedure similar to that of Example 117.

EXAMPLE 118

O-(2-Amino-4-methyl-phenyl)-N-t-butoxycarbonyl-D-serine $^1$H NMR (CDCl$_3$) δ6.4–6.6 (m, 3H), 6.0 (d, 1H), 4.55 (m, 1H), 4.25 (m, 1H), 4.10 (m, 1H), 2.12 (s, 3H), 1.35 (s, 9H),

EXAMPLE 119

O-(2-Amino-5-methyl-phenyl)-N-t-butoxycarbonyl-D-serine $^1$H NMR (D$_6$DMSO) δ7.50 (d, 1H), 6.46–6.66 (m, 3H), 4.46 (m, 1H), 4.28 (m, 1H), 4.0 (m, 1H), 1.42 (s, 9H).

EXAMPLE 120

O-(2-Amino-4-fluoro-phenyl)-N-t-butoxycarbonyl-D-threonine $^1$H NMR (CDCl$_3$) δ6.0–7.0 (m, 4H), 3.7–5.0 (m, 2H), 1.42 (m, 12H).

Mass spectrum: m/e=328.14319±0.78 ppm.

EXAMPLE 121

O-(2-Amino-5-fluoro-phenyl)-N-t-butoxycarbonyl-D-threonine $^1$H NMR (CDCl$_3$) δ6.60 (m, 1H), 6.45 (m, 1H), 6.35 (m, 1H), 4.82 (m, 1H), 4.20 (m, 1H), 1.15 (s, 9H), 1.10 (d, 3H).

Mass spectrum: m/e=328.14277±2.08 ppm.

The title compounds of Example 122–128 were prepared by a procedure similar to that of Example 105C.

EXAMPLE 122

D-3-t-Butoxycarbonyl-amino-2,3-dihydro-7-methyl-1,5-benzoxazepin-4(5H)-one $^1$H NMR (CDCl$_3$) δ7.75 (s, 1H), 7.0 (m, 2H), 6.80 (s, 1H), 5.5 (d, 1H), 4.60 (m, 1H), 4.20 (m, 2H), 2.25 (s, 3H), 1.42 (s, 9H).

EXAMPLE 123

D-3-t-Butoxycarbonyl-amino-2,3-dihydro-7-fluoro-1,5-benzoxazepin-4(5H)-one $^1$H NMR (CDCl$_3$) δ8.50 (s, 1H), 7.0 (m, 1H), 6.62–6.8 (m, 2H), 5.44 (d, 1H), 4.44–4.7 (m, 2H), 4.10 (m, 1H), 1.35 (s, 9H).

EXAMPLE 124

D-3-t-Butoxycarbonyl-amino-2,3-dihydro-8-methyl-1,5-benzoxazepin-4(5H)-one $^1$H NMR (CDCl$_3$) δ8.50 (s, 1H), 6.8–7.0 (s, 3H), 5.58 (d, 1H), 4.60 (m, 1H), 4.20 (m, 2H), 2.30 (s, 3H), 1.42 (s, 9H).

EXAMPLE 125

D-3-t-Butoxycarbonyl-amino-2,3-dihydro-8-fluoro-1,5-benzoxazepin-4(5H)-one

MP=172°–174° C.

$^1$H NMR (CDCl$_3$) δ8.65 (s, 1H), 6.95 (m, 1H), 6.82 (m, 2H), 5.52 (d, 1H), 4.65 (m, 2H), 4.25 (m, 1H), 1.45 (s, 9H).

Mass spectrum: m/e=296.11724±0.00 ppm.

EXAMPLE 126

2(S)-Methyl-3(R)-t-butyloxycarbonyl-amino-2,3-dihydro-1,5-benzoxazepin-4(5H)-one $^1$H NMR (CDCl$_3$) δ9.05 (s, 1H), 6.9–7.1 (m, 4H), 4.60 (m, 1H), 3.82 (d, 1H), 2.10 (bs, 2H), 1.43 (d, 3H).

Mass spectrum: m/e=292.14228±0.10 ppm.

EXAMPLE 127

2(S)-Methyl-3(R)4-butyloxycarbonyl-amino-7-fluoro-2,3-dihydro-1,5-benzoxazepin-4(5H)-one $^1$H NMR (CDCl$_3$) δ8.70 (s, 1H), 7.10 (m, 1H), 6.82 (m, 1H), 6.75 (m, 1H), 5.52 (d, 1H), 4.82 (m, 1H), 4.72 (m, 1H), 1.38 (s, 9H), 1.35 (d, 3H).

Mass spectrum: m/e=310.13195±3.03 ppm.

EXAMPLE 128

2(S)-Methyl-3(R)-t-butyloxycarbonyl-amino-8-fluoro-2,3-dihydro-1,5-benzoxazepin-4(5H)-one $^1$H NMR (CDCl$_3$) δ9.35 (S, 1H), 6.95 (m, 1H), 6.8 (d,d, 1H), 6.62 (m, 1H), 5.67 (d, 1H), 4.82 (m, 1H), 4.70 (m, 1H), 1.37 (s, 9H), 1.34 (d, 3H).

EXAMPLE 129

7(R)-Amino-8-[2-oxo-2-(3,3-dimethyl-piperidin-1-yl)ethyl]-6,7-dihydro-9H-5-oxa-9-aza-benzocyclohepten-8-one The title compound was prepared by a procedure similar to that of Example 33 using the benoxazepine nucleus employed in Example 105D.

$^1$H NMR (CDCl$_3$) δ7.0–7.3 (m, 4H), 5.12 (d, 1H), 4.45 (m, 1H), 3.8–4.2 (m, 3H), 3.0–3.65 (m, 4H), 1.85 (bs, 2H), 1.3–1.7 (m, 4H), 0.8–1.05 (s, s, s, s, 6H).

The title compounds of Examples 130–135 were prepared by a procedure similar to that of Example 105D.

EXAMPLE 130

3-D-Amino-2,3-dihydro-7-methyl-1,5-benzoxazepin-4(5H)-one

MP=139° C.

$^1$H NMR (CDCl$_3$) δ8.75 (bs, 1H), 7.0 (d, 1H), 6.88 (d, 1H), 6.82 (s, 1H), 4.44 (m, 1H), 4.15 (m, 1H), 3.80 (m, 1H), 2.32 (s, 3H).

$[\alpha]_D^{25}$=+294° (C=1, CH$_3$OH).

EXAMPLE 131

3-D-Amino-2,3-dihydro-7-fluoro-1,5-benzoxazepin-4(5H)-one

MP=176°–178° C.

$^1$H NMR (D$_6$DMSO) δ10.20 (s, 1H) 7.05 (m, 1H), 6.84 (m, 2H), 4.25 (M, 1H), 3.98 (m, 1H), 3.68 (m, 1H), 3.28 (bs, 2H).

$[\alpha]_D^{25}$=+278.5° (C=1 CH$_3$OH).

EXAMPLE 132

3-D-Amino-2,3-dihydro-8-methyl-1,5-benzoxazepin-4(5H)-one

MP=145.8° C.

$^1$H NMR (CDCl$_3$) δ7.62 (bs, 1H), 6.92 (s, 1H), 6.8–6.92 (m, 2H), 4.44 (m, 1H), 4.16 (m, 1H), 3.82 (m, 1H), 2.32 (s, 3H).

$[\alpha]_D^{25}$=+378.8° (C=1; CH$_3$OH).

EXAMPLE 133

3-D-Amino-2,3-dihydro-8-fluoro-1,5-benzoxazepin-4(5H)-one

MP=178.4°–179.5° C.

$^1$H NMR (CDCl$_3$) δ7.56 (bs, 1H), 7.76–8.0 (m, 3H), 4.46 (m, 1H), 4.20 (t, 1H), 3.82 (m, 1H), 1.80 (bs, 2H).

$[\alpha]_D^{25}$=+233.80 (C=1; CH$_3$OH).

EXAMPLE 134

2(S)-Methyl-3(R)-amino-2,3-dihydro-1,5-benzoxazepin-4(5H)-one $^1$H NMR (CDCl$_3$) δ9.05 (bs, 1H), 6.88–7.2 (m, 4H), 4.62 (m, 1H), 3.85 (d, 1H), 2.05 (bs, 2H), 1.33 (d, 3H).

EXAMPLE 135

2(S)-Methyl-3(R)-amino-8-fluoro-2,3-dihydro-1,5-benzoxazepin-4(5H)-one

MP=165°–166° C.

$^1$H NMR (CDCl$_3$) δ9.0 (bs, 1H), 6.96 (m, 1H), 6.72–6.88 (m, 2H), 4.65 (m, 1H), 3.87 (bs, 1H), 1.62 (bs, 2H), 1.38 (d, 3H).

$[\alpha]_D^{25}$=155.1° (C=0.5, CH$_2$Cl$_2$).

The title compounds of Examples 136–159 were prepared by a procedure similar to that of Example 105E.

EXAMPLE 136

7(S)-1-(8-Oxo-6,7,8,9-tetrahydro-5-oxa-9-aza-benzocyclohepten-7-yl)-3-m-tolyl-urea

MP=216° C.

$^1$H NMR (D$_6$DMSO) δ8.86 (s, 1H), 7.0–7.25 (m, 8H), 6.72 (d, 1H), 6.58 (s, 1H), 4.60 (m, 1H), 3.95 (m, 1H), 4.70 (m, 1H), 2.25 (s, 3H).

EXAMPLE 137

7(R)-1-(3-Chloro-phenyl)-3-(8-oxo-6,7,8,9-tetrahydro-5-oxa-9-aza-benzocyclohepten-7-yl)-urea

MP=219° C.

$^1$H NMR (D$_6$DMSO) δ9.15 (s, 1H), 7.62 (m, 1H), 6.9–7.3 (m, 8H), 6.65 (m, 1H), 4.55 (m, 1H), 4.45 (m, 1H), 4.22 (m, 1H).

EXAMPLE 138

7(R)-1-(3-Methoxy-phenyl)-3-(8-oxo-6,7,8,9-tetrahydro-5-oxa-9-aza-benzocyclohepten-7-yl)-urea

MP=199° C.

$^1$H NMR (D$_6$DMSO) δ8.95 (s, 1H), 7.1–7.25 (m, 7H), 6.8 (m, 1H), 6.62 (m, 1H), 6.48 (m, 1H), 4.55 (m, 1H), 4.45 (m, 1H), 4.22 (m, 1H), 3.63 (s, 3H).

EXAMPLE 139

7(R)-1-(2-Fluoro-8-oxo-6,7,8,9-tetrahydro-5-oxa-9-aza-benzocyclo-hepten-7-yl)-3-m-tolyl-urea
MP=226° C.
$^1$H NMR (CDCl$_3$) δ8.86 (s, 1H), 6.9–7.25 (m, 7H), 6.72 (m, 1H), 6.56 (m, 1H), 4.62 (m, 1H), 4.45 (m, 1H), 4.22 (m, 1H), 2.20 (s, 3H).

EXAMPLE 140

7(R)-1-(3-Ethyl-phenyl)-3-(8-oxo-6,7,8,9-tetrahydro-5-oxa-9-aza-benzocyclohepten-7-yl)-urea
MP=208° C.
$^1$H NMR (CDCl$_3$) δ8.36 (s, 1H), 6.90–7.10 (m, 8H), 6.70 (m, 1H), 4.80 (m, 1H), 4.55 (m, 1H), 4.16 (m, 1H), 2.24 (q, 2H), 1.08 (t, 3H).

EXAMPLE 141

7(R)-1(2-Methyl-8-oxo-6,7,8,9-tetrahydro-5-oxa-9-aza-benzocyclo-hepten-7-yl)-3-m-tolyl-urea
MP=173° C.
$^1$H NMR (D$_6$DMSO) δ10.1 (s, 1H), 8.8 (s, 1H), 6.85–7.2 (m, 7H), 6.72 (d, 1H), 6.55 (d, 1H), 4.60 (m, 1H), 4.45 (m, 1H), 4.18 (m, 1H), 2.28 (s, 3H), 2.25 (s, 3H).

EXAMPLE 142

7(R)-1-(4-Nitro-phenyl)-3-(8-oxo-6,7,8,9-tetrahydro-5-oxa-9-aza-benzocyclohepten-7-yl)-urea
MP=>250° C.
$^1$H NMR (D$_6$DMSO) δ9.68 (s, 1H), 8,14 (d, 2H), 7.60 (d, 2H), 7,0–7.22 (m, 5H), 6.90 (m, 1H), 4.60 (m, 1H), 4.52 (m, 1H), 4.26 (m, 1H).

EXAMPLE 143

7(R)-1-(1-Naphthalen-1-yl-ethyl)-3-(8-oxo-6,7,8,9-tetrahydro-5-oxa-9-aza-benzocyclohepten-7-yl)-urea
MP=242° C.
$^1$H NMR (D$_6$DMSO) δ10.5 (s, 1H), 8.08 (d, 1H), 7.92 (d, 1H), 7.80 (m, 1H), 7.4–7.6 (m, 4H), 6.94–7.2 (m, 5H), 6.30 (d, 1H), 5.5 (t, 1H), 4.55 (m, 1H), 4.33 (m, 1H), 4.10 (m, 1H), 1.42 (d, 3H).

EXAMPLE 144

7(R)-1-(8-Oxo-6,7,8,9-tetrahydro-5-oxa-9-aza-benzocyclohepten-7-yl)-3-(2-trifluoromethyl-phenyl)-urea
MP=243° C.
$^1$H NMR (D$_6$DMSO) δ10.30 (s, 1H), 7.92 (d, 1H), 7.55–7.7 (m, 3H) 7.10–7.30 (m, 5H), 4.67 (m, 1H), 4.55 (m, 1H), 4.25 (m, 1H).

EXAMPLE 145

7(R)-1-(2-Nitro-phenyl)-3-(8-oxo-6,7,8,9-tetrahydro-5-oxa-9-aza-benzocyclohepten-7-yl)-urea
$^1$H NMR (D$_6$DMSO) δ10.05 (s, 1H), 9.87 (s, 1H), 8.06 (d, 1H), 7.95 (d, 1H), 7.72 (t, 1H), 7.26 (t, 1H), 7.05 (s, 4H), 4.27 (m, 1H), 4.0 (m, 1H), 3.60 (m, 1H).

EXAMPLE 146

7(R)-1-(2-Methoxy-phenyl) 3-(8-oxo-6,7,8,9-tetrahydro-5-oxa-9-aza-benzocyclohepten-7-yl)-urea
MP=153° C.
$^1$H NMR (D$_6$DMSO) δ10.3 (s, 1H), 8.45 (s, 1H), 8.06 (d, 1H), 7.48 (d, 1H), 7.15–7.25 (m, 4H), 6.8–7.0 (m, 3H), 4.68 (m, 1H), 4.52 (m, 1H), 4.25 (m, 1H) 3.92 (s, 3H).

EXAMPLE 147

7(R)-2-[3-(8-oxo-6,7,8,9-tetrahydro-5-oxa-9-aza-benzocyclohepten-7-yl)-ureido]-benzoic acid ethyl ester
$^1$H NMR (D$_6$DMSO) δ9.95 (s, 1H), 9.80 (s, 1H), 8.15 (d, 1H), 7.85 (d, 1H), 7.80 (d, 1H), 7.40 (t, 1H), 6.9–7.1 (m, 6H), 4.55 (m, 1H), 4.1–4.4 (m, 4H), 1.22 (t, 3H).

EXAMPLE 148

7(R)-1-(2-Isopropyl-phenyl)-3-(8-oxo-6,7,8,9-tetrahydro-5-oxa-9-aza-benzocyclohepten-7-yl)-urea
$^1$H NMR (D$_6$DMSO) δ10.3 (s, 1H), 8.4 (s, 1H), 7.7 (d, 1H), 7.35 (d, 1H), 7.05–7.30 (m, 7H), 4.75 (m, 1H), 4.62 (m, 1H), 4.33 (m, 1H), 3.25 (m, 1H), 1.30 (d, 6H).

EXAMPLE 149

7(R)-2-[3-(8-Oxo-6,7,8,9-tetrahydro-5-oxa-9-aza-benzocyclohepten-7-yl)-ureido]benzoic acid t-butyl ester
$^1$H NMR (D$_6$DMSO) δ11.1 (s, 1H), 9.15 (s, 1H), 8.02 (s, 1H), 7.4–7.52 (m, 2H), 7.31 (t, 1H), 7.10 (m, 4H), 6.58 (d, 1H), 4.59 (m, 1H), 4.45 (m, 1H), 4.24 (m, 4H), 1.26 (t, 3H).

EXAMPLE 150

7(R)-2-[3-(8-Oxo-6,7,8,9-tetrahydro-5-oxa-9-aza-benzocyclohepten-7-yl)-ureido]benzoic acid methyl ester
$^1$H NMR (D$_6$DMSO) δ10.15 (s, 1H), 9.95 (s, 1H), 8.28 (d, 1H), 8.05 (d, 1H), 7.95 (d, 1H), 7.55 (t, 1H), 7.05–7.25 (m, 5H), 4.65 (m, 1H), 4.46 (m, 1H), 4.32 (m, 1H), 3.95 (s, 3H).

EXAMPLE 151

7(R)-1-(3-Methyl-8-oxo-6,7,8,9-tetrahydro-5-oxa-9-aza-benzocyclo-hepten-7-yl)-3-(m-tolyl)-urea
$^1$H NMR (D$_6$DMSO) δ10.12 (s, 1H). 8.85 (s, 1H), 6.8–7.2 (m, 6H), 6.7 (d, 1H), 6.6 (d, 1H), 4.58 (m, 1H), 4.42 (m, 1H), 4.18 (m, 1H), 2.28 (s, 3H), 2.25 (s, 3H).

EXAMPLE 152

7(R)-1-(3-Fluoro-8-oxo-6,7,8,9-tetrahydro-5-oxa-9-aza-benzocyclo-hepten-7-yl)-3-m-tolyl)-urea
$^1$H NMR (D$_6$DMSO) δ10.1 (s, 1H), 8.85 (s, 1H), 6.92–7.25 (m, 5H), 6.75 (d, 1H), 6.58 (d, 1H), 4.58 (m, 1H), 4.48 (m, 1H), 4.22 (m, 1H), 2.28 (s, 3H).

EXAMPLE 153

7(R)-1-(3-Chloro-phenyl)-3-(2-fluoro-8-oxo-6,7,8,9-tetrahydro-5-oxa-9-aza-benzocyclohepten-7-yl)-urea
MP=243° C.
$^1$H NMR (D$_6$DMSO) δ10.2 (s, 1H), 9.15 (s, 1H), 7.62 (m, 1H), 7.12–7.32 (m, 3H), 6.9–7.05 (m, 3H), 6.7 (d, 1H), 4.65 (m, 1H), 4.48 (m, 1H), 4.20 (m, 1H).

EXAMPLE 154

7(R)-1-(3-Chloro-phenyl)-3-(3-fluoro-8-oxo-6,7,8,9-tetrahydro-5-oxa-9-aza-benzocyclohepten-7-yl)-urea
$^1$H NMR (D$^6$DMSO) δ9.18 (s, 1H), 7.61 (m, 1H), 6.9–7.3 (m, 7H), 6.65 (d, 1H), 4.42–4.63 (m, 2H), 4.25 (t, 1H).
Mass spectrum: m/e=350 (P+1).

EXAMPLE 155

6(S),7(R)-1-(6-Methyl-8-oxo-6,7,8,9-tetrahydro-5-oxa-9-aza-benzocyclo-hepten-7-yl)-3-(m-tolyl)-urea
$^1$H NMR (D$_6$DMSO) δ10.20 (s, 1H), 8.82 (s, 1H), 7.08–7.2 (m, 7H), 6.72 (d, 1H), 6.63 (d, 1H), 4.70 (m, 2H), 2.20 (s, 3H), 1.30 (d, 3H).

EXAMPLE 156

6(S),7(R)-1-(3-Chloro-phenyl)-3-(6-methyl-8-oxo-6,7,8,9-tetrahydro-5-oxa-9-aza-benzocyclohepten-7-yl)-urea $^1$H NMR (CDCl$_3$) δ8.45 (s, 1H), 7.90 (s, 1H), 7.40 (s, 1H), 6.75–7.2 (m, 8H), 5.05 (m, 1H), 4.85 (m, 1H), 1.45 (d, 1H).

EXAMPLE 157

7(R)-1-(8-Oxo-6,7,8,9-tetrahydro-5-oxa-9-aza-benzocyclohepten-7-yl)-3-(2-thiophen-2-yl-ethyl)-urea $^1$H NMR (CDCl$_3$) δ6.8–7.4 (m, 8H), 4.90 (m, 1H), 4.65 (m, 1H), 4.20 (m, 1H), 3.45 (m, 2H), 2.95 (m, 2H).

EXAMPLE 158

6(S),7(R)-1-(3-Chloro-phenyl)-3-(3-fluoro-6-methyl-8-oxo-6,7,8,9-tetrahydro-5-oxa-9-aza-benzocyclohepten-7-yl)-urea $^1$H NMR (D$_6$DMSO) δ10.2 (s, 1H), 9.15 (s, 1H), 7.62 (m, 1H), 7.12–7.32 (m, 3H), 6.9–7.05 (m, 3H), 6.7 (d, 1H), 5.0 (m, 1H), 4.9 (m, 1H), 1.42 (d, 3H).

EXAMPLE 159

6(S),7(R)-1-(3-Fluoro-6-methyl-8-oxo-6,7,8,9-tetrahydro-5-oxa-9-aza-benzocyclohepten-7-yl)-3-(m-tolyl)-urea $^1$H NMR (D$_6$DMSO) δ10.1 (s, 1H), 8.85 (s, 1H), 6.92–7.25 (m, 6H), 6.75 (d, 1H), 6.58 (d, 1H), 5.0 (m, 1H), 4.9 (m, 1H), 2.28 (s, 3H), 1.42 (d, 3H).

As an alternate to the procedure of Example 105E, the procedure of Example 160 may be used to prepare compounds having an m-dimethylamino-phenyl-urea substituent.

EXAMPLE 160

6(S),7(R)-1-(3-Dimethylamino-phenyl)-3-(6-methyl-8-oxo-6,7,8,9-tetrahydro-5-oxa-9-aza-benzocyclohepten-7-yl)-urea A mixture of 0.192 g (0.001M) of 2(S)-Methyl-3(R)-amino-2,3-dihydro-1,5-benzoxazepin-4(5H)-one, 0.165 g (0.001M) of 3-dimethylaminobenzoic acid, 0.215 mL (0.001M) of diphenylphosphoryl azide and 0.14 mL (0.001M) of triethylamine in 10 mL of dioxane was refluxed under nitrogen for 2 hours. The reaction was cooled to room temperature and the solvent evaporated to yield a yellow gum. To the residue was added 20 ml of water and the pH adjusted to 9.5 with 1N NaOH. The mixture was extracted 3 times with 25 mL of ethyl acetate. The ethyl acetate layers were combined, dried and evaporated. The residue was chromatographed on silica using 1:1 ethyl acetate:hexane as the elutant. Appropriate fractions were combined and evaporated to yield 0.150 g (50%) of product as a yellow amorphous solid.

$^1$H NMR (CDCl$_3$) δ8.58 (s, 1H), 7.68 (s, 1H), 6.8–7.2 (m, 7H), 6.58 (d, 1H), 6.38 (d, 1H), 5.05 (m, 1H), 4.92 (m, 1H), 2.83 (s, 6H), 1.40 (d, 3H).

Mass spectrum: m/e=354.16582±9.54 ppm.

The title compounds of Examples 161–164 were prepared using a procedure similar to that of Example 160.

EXAMPLE 161

7(R)-1-(3-Dimethylamino-phenyl)-3-(8-oxo-6,7,8,9-tetrahydro-5-oxa-9-aza-benzocyclohepten-7-yl)-urea $^1$H NMR (CDCl$_3$) δ7.72 (s, 1H), 6.96–7.22 (m, 7H), 6.85 (m, 1H), 6.48 (m, 1H), 6.19 (m, 1H), 4.99 (m, 1H), 4.72 (m, 1H), 4.22 (m, 1H) 2.95 (s, 6H).

EXAMPLE 162

7(R)-1-(3-Dimethylamino-phenyl)-3-(2-fluoro-8-oxo-6,7,8,9-tetrahydro-5-oxa-9-aza-benzocyclohepten-7-yl)-urea $^1$H NMR (CDCl$_3$) δ8.60 (s, 1H), 7.0–7.3 (m, 4H), 6.68–6.9 (m, 3H), 6.45 (m, 1H), 6.28 (m, 1H), 4.95 (m, 1H), 4.65 (m, 1H), 4.29 (m, 1H), 2.90 (s, 3H).

EXAMPLE 163

7(R)-1-(3-Dimethylamino-phenyl)-3-(3-fluoro-8-oxo-6,7,8,9-tetrahydro-5-oxa-9-aza-benzocyclohepten-7-yl)-urea $^1$H NMR (CD$_3$OD) δ7.0–7.2 (m, 3H), 6.8–7.0 (m, 3H), 6.60 (d, 1H), 6.42 (d, 1H), 4.80 (m, 1H), 4.55 (m, 1H), 4.25 (t, 1H), 2.92 (5, 6H).

EXAMPLE 164

6(S),7(R)-1-(3-Dimethylamino-phenyl)-3-(3-fluoro-6-methyl-8-oxo-6,7,8,9-tetrahydro-5-oxa-9-aza-benzocyclohepten-7-yl)-urea $^1$H NMR (CDCl$_3$) δ8.45 (s, 1H), 7.42 (s, 1H), 7.08 (t, 1H), 6.82–7.0 (m, 3H), 6.8 (m, 1H), 6.45 (m, 3H), 5.02 (t, 1H), 4.92 (t, 1H), 2.88 (s, 6H), 1.41 (d, 3H).

The title compounds of Examples 165–220 were prepared by a procedure similar to that of Example 105.

EXAMPLE 165

(R)-1-{9-[2-(3,3-Dimethylpiperidin-1-yl)-2-oxo-ethyl]-8oxo-6,7,8,9-tetrahydro-5-oxa-9-aza-benzocyclohepten-7-yl}-3-m-tolyl-urea $^1$H NMR (CDCl$_3$) δ7.65 (m, 1H), 7.20 (m, 6H), 7.05 (d, 2H), 6.70 (m, 1H), 6.50 (m, 1H), 4.0–5.1 (m, 5H), 2.9–3.6 (m, 4H), 2.15 (s, 3H), 1.3–1.5 (m, 4H), 1.0 (s, 3H), 0.9 (s, 3H).

EXAMPLE 166

7(R)-1-{9-[2-(3,5-Dimethylpiperidin-1-yl-4-one)-2-oxoethyl]-8-oxo-6,7,8, 9-tetrahydro-5-oxa-9-aza-benzocyclohepten-7-yl}-3-m-tolyl-urea $^1$H NMR (CDCl$_3$)7.15–7.4 (m, 6H), 6.9–7.1 (m, 2H), 6.8 (d, 1H), 6.4 (d, 1H), 5.0 (m, 2H), 4.65 (t, 1H), 4.2–4.4 (m, 2H), 3.55 (m, 1H), 3.5 (m, 3H), 2.20 (s, 3H), 1.32 (s, 3H), 1.15 (s, 3H), 1.10 (s, 3H), 1.05 (s, 3H).

EXAMPLE 167

7(R)-3-(3-{9-[2-(3,3-Dimethylpiperidin-1-yl)-2-oxo-ethyl]-8-oxo-6,7,8,9-tetrahydro-5-oxa-9-aza-benzocyclohepten-7-yl}-ureido)-benzoic acid ethyl ester $^1$H NMR (CDCl$_3$) δ7.93 (d, 2H), 7.34–7.52 (m, 2H), 7.0–7.2 (m, 5H), 6.62 (t, 1H), 4.8–5.0 (m, 2H), 4.54 (m, 1H), 4.12–4.40 (m, 4H), 3.8–4.35 (m, 4H), 1.20–1.60 (m, 7H), 0.80–1.0 (s, s, s, s, 6H).

EXAMPLE 168

7(S)-1-{9-[2-(3,3-Dimethylpiperidin-1-yl) -2-oxo-ethyl]-8-oxo -6,7,8,9-tetrahydro-5-oxa-9-aza-benzocyclohepten-7-yl}-3-m-tolyl-urea $^1$H NMR (CDCl$_3$) δ6.85–7.3 (m, 8H), 6.75 (d, 1H), 6.28 (m, 1H), 4.9–5.1 (m, 2H), 4.68 (m, 1H), 4.15–4.4 (m, 2H), 3.0–3.6 (m, 4H), 2.20 (s, 3H), 1.5–1.9 (m, 4H), 1.0 (s, 6H).

Mass spectrum: m/e=465 (P+1).

EXAMPLE 169

7(R)-1-{9-[2-(N,N-Diisopropylamino-1-yl)-2-oxo-ethyl]-8-oxo-6,7,8,9-tetrahydro-5-oxa-9-aza-benzocyclohepten-7-yl}-3-m-tolyl-urea $^1$H NMR (D$_6$ DMSO) δ7.0–7.3 (m, 8H), 6.72 (d, 1H), 6.60 (d, 1H), 4.95 (m, 1H), 4.65 (m, 1H), 4.45 (m, 1H), 4.20 (m, 2H), 4.0 (m, 1H), 3.5 (m, 1H), 2.2 (s, 3H), 1.1–1.35 (m, 12H).

Mass spectrum: m/e=453 (P+1).

EXAMPLE 170

7(R)-1-{9-[2-(8-Aza-spiro[4.5]dec-8-yl)-2-oxo-ethyl]-8-oxo-6,7,8,9-tetrahydro-5-oxa-9-aza-benzocyclohepten-7-yl}-3-m-tolyl-urea $^1$H NMR (CDCl$_3$) δ7.0–7.3 (m, 8H), 6.78 (d, 1H), 6.20 (d, 1H), 4.9–5.1 (m, 2H), 4.7 (m, 1H), 4.2–4.35 (m, 2H), 3.3–3.6 (m, 4H), 2.22 (s, 3H), 1.3–1.7 (m, 12H).

Mass spectrum: m/e=491 (P+1).

EXAMPLE 171

7(R)-1-{9-[2-(2,6-Dimethylpiperidin-1-yl)-2-oxo-ethyl]-8-oxo-6,7,8,9-tetrahydro-5-oxa-9-aza-benzocyclohepten-7-yl}-3-m-tolyl-urea $^1$H NMR (CDCl$_3$) δ7.45 (s, 1H), 7.1–7.3 (m, 6H), 6.95–7.03 (m, 2H), 6.75 (d, 1H), 5.05 (m, 2H), 4.70 (m, 2H), 4.35 (m, 2H)<4.0 (m, 1H), 2.20 (s, 3H), 1.1–1.8 (m, 12H).

Mass spectrum: m/e=465 (P+1).

EXAMPLE 172

7(R)-1-[9-(2-Azocan-1-yl-2-oxo-ethyl)-8-oxo-6,7,8,9-tetrahydro-5-oxa-9-aza -benzocyclohepten-7-yl]-3-m-tolyl-urea $^1$H NMR (CDCl$_3$) δ7.55 (bs, 1H), 7.1–7.3 (m, 5H), 6.95 (m, 2H), 6.70 (m, 1H), 6.50 (bs, 1H), 4.9–5.1 (m, 2H), 4.62 (m, 1H), 4.35 (t, 1H), 4.20 (d, 1H), 3.35–3.6 (m, 4H), 2.15 (s, 3H), 1.4–1.9 (m, 10H).

Mass spectrum: m/e=465 (P+1).

EXAMPLE 173

7(R)-2-[8-Oxo-7-(3-m-tolyl-ureido)-6,7-dihydro-8H-(5-oxa-9-aza-benzocyclohepten-9-yl]-N-(1,2,3,4-tetrahydro-naphthalen-1-ylmethyl)-acetamide $^1$H NMR (CDCl$_3$) δ7.62 (bs, 1H), 6.9–7.3 (m, 11H), 6.8 (d, 1H), 6.72 (m, 1H), 6.30 (m, 1H), 4.9 (m, 1H), 4.72 (d, 1H), 4.58 (m, 1H), 4.32 (d, 1H), 4.0 (m, 1H), 3.3–3.6 (m, 2H), 2.88 (m, 1H), 2.62 (m, 2H), 2.20 (s, 3H), 1.4–1.8 (m, 4H).

Mass spectrum: m/e=513 (P+1).

EXAMPLE 174

7(R)-1-{9-[2-(3,3-Dimethylpiperidin-1-yl)-2-oxo-ethyl]-8-oxo-6,7,8,9-tetrahydro-5-oxa-9-aza-benzocyclohepten-7-yl}-3-m-methoxyphenyl-urea $^1$H NMR (CDCl$_3$) δ7.7 (m, 1H) 6.9–7.3 (m, 6H), 6.72 (d, 1H), 6.6 (m, 1H), 6.45 (m, 1H), 4.9–5.15 (m, 2H), 4.65 (m, 1H), 4.1–4.4 (m, 2H), 3.65 (s, 3H), 2.9–3.4 (m, 4H), 1.1–1.7 (m, 4H), 0.7–1.0 (s,s,s, 6H).

Mass spectrum: m/e=481 (P+1).

EXAMPLE 175

7(R)-1-{9-[2-(3,3-Dimethylpiperidin-1-yl)-2-oxo-ethyl]-8-oxo-6,7,8,9-tetrahydro-5-oxa-9-aza-benzocyclohepten-7-yl}-3-m-chlorophenyl-urea $^1$H NMR (CDCl$_3$) δ7.90 (s, 1H), 7.45 (s, 1H), 6.9–7.25 (m, 6H), 6.8 (d, 1H), 6.67 (d, 1H), 4.9–5.1 (d, 2H), 4.6 (m, 1H), 4.1–4.4 (m, 2H) 1.35–1.7 (m, 4H), 0.7–1.0 (s,s,s,s 6H).

Mass spectrum: m/e=484 (P+1).

EXAMPLE 176

7(R)-1-{9-[2-(7-Aza-spiro[4.5]dec-7-yl)-2-oxo-ethyl]-8-oxo-6,7,8,9tetrahydro-5-oxa-9-aza-benzocyclohepten-7-yl}-3-m-methoxyphenyl-urea $^1$H NMR (CDCl$_3$) δ7.5 (m, 1H), 6.95–7.3 (m, 6H), 6.75 (d, 1H), 6.50 (m, 2H), 4.9–5.15 (m, 2H), 4.65 (m, 1H), 4.1–4.4 (m, 2H), 3.65 (s, 3H), 3.0–3.4 (m, 4H), 1.3–1.8 (m, 12H).

Mass spectrum: m/e=507 (P+1).

EXAMPLE 177

7(R)-1-{9-[2-(7-Aza-spiro[4.5]dec-7-yl)-2-oxo-ethyl]-8-oxo-6,7,8,9-tetrahydro-5-oxa-9-aza-benzocyclohepten-7-yl}-3-m-chlorophenyl-urea $^1$H NMR (CDCl$_3$) δ7.77 (d, 1H), 7.4 (s, 1H), 6.9–7.3 (m, 6H), 6.85 (d, 1H), 6.62 (m, 1H), 4.9–5.1 (m, 2H), 4.55 (m, 1H), 4.1–4.45 (m, 2H), 3.0–3.4 (m, 4H), 1.3–1.95 (m, 12H).

Mass spectrum: m/e=511 (P+1).

EXAMPLE 178

7(R)-1-{9-[2-(Piperidin-1-yl)-2-oxo-ethyl]-8-oxo-6,7,8,9-tetrahydro-5-oxa-9-aza-benzocyclohepten-7-yl}-3-m-tolyl-urea $^1$H NMR (CDCl$_3$) δ6.9–7.22 (m, 8H), 6.82 (d, 1H), 6.20 (d, 1H), 4.9–5.1 (m, 2H), 4.72 (m, 1H), 4.2–4.4 (m, 2H), 3.60 (m, 2H), 3.40 (m, 2H), 2.22 (s, 3H), 1.5–1.75 (m, 6H).

Mass spectrum: m/e=437 (P+1).

EXAMPLE 179

7(R)-1-{9-[2-(7-Aza-spiro[4.5]dec-7-yl)-2-oxo-ethyl]-8-oxo-6,7,8,9tetrahydro-5-oxa-9-aza-benzocyclohepten-7-yl}-3-m-tolyl-urea $^1$H NMR (CDCl$_3$) δ6.8–7.4 (m, 8H), 6.68 (m, 1H), 6.30 (m, 1H), 4.8–5.0 (m, 2H), 4.60 (m, 1H), 4.0–4.26 (m, 2H), 2.9–3.3 (m, 4H), 2.10 (s, 3H), 1.0–1.7 (m, 12H).

Mass spectrum: m/e=491 (P+1).

EXAMPLE 180

7(R)-1-{9-[2-(3,3,5,5-Tetramethylpiperidin-1-yl)-2-oxo-ethyl]-8-oxo-6,7,8,9-tetrahydro-5-oxa-9-aza-benzocyclohepten-7-yl}-3-m-chlorophenyl-urea $^1$H NMR (CDCl$_3$) δ7.68 (s, 1H), 7.40 (m, 1H), 7.0–7.25 (m, 5H), 6.95 (m, 2H), 6.75 (d, 1H), 4.95–5.1 (m, 2H), 4.55 (t, 1H), 4.32 (t, 1H), 4.18 (d, 1H), 3.34 (m, 1H), 2.9–3.1 (m, 3H), 1.30 (s, 2H), 1.08 (s, 3H), 0.95 (s, 3H), 0.89 (s, 3H), 0.85 (s, 3H).

Mass spectrum: m/e=513 (P+1).

EXAMPLE 181

7(R)-1-{9-[2-(3,3-Dimethylpiperidin-1-yl)-2-oxo-ethyl]-2-fluoro-8-oxo-6,7, 8,9-tetrahydro-5-oxa-9-aza-benzocyclohepten-7-yl}-3-m-tolyl-urea

MP=138°–142° C.

$[α]_D^{25}$=223.8°, (C=1, CDCl$_3$).

¹H NMR (CDCl₃) δ6.85–7.2 (m, 7H), 6.80 (m, 1H), 6.20 (m, 1H0, 4.9–5.1 (m, 2H), 4.68 (m, 1H), 4.1–4.35 (m, 2H), 2.9–3.6 (m, 4H), 2.22 (s, 3H), 1.3–1.65 (m, 4H), 0.7–1.05 (s,s,s 6H).

Mass spectrum: m/e=483 (P+1).

EXAMPLE 182

7(R)-1-{9-[2-(7-Aza-spiro-[4,5]dec-7-yl)-2-oxo-ethyl]-2-fluoro-8-oxo-6,7,8,9-tetrahydro-5-oxa-9-aza-benzocyclohepten-7-yl}-3-m-tolyl-urea

MP=132° C.

[α]$_D^{25}$=198° C., (C=1, CDCl₃).

¹H NMR (CDCl₃) δ6.85–7.2 (m, 7H), 6.75 (m, 1H), 6.20 (m, 1H), 4.9–5.1 (m, 2H), 4.70 (m, 1H), 4.1–4.35 (m, 2H), 3.0–3.4 (m, 4H), 2.25 (s,s 3H), 1.2–1.8 (m, 12H).

Mass spectrum: m/e=508 (P+1).

EXAMPLE 183

7(R)-1-{9-[2-(3,3,5,5-Tetramethylpiperidin-1-yl)-2-oxo-ethyl]-8-oxo-6,7,8,9-tetrahydro-5-oxa-9-aza-benzocyclohepten-7-yl}-3-m-tolyl-urea ¹H NMR (CDCl₃) δ7.46 (s, 1H), 7.06–7.22 (m, 5H), 6.95 (m, 2H), 6.67 (m, 1H), 6.55 (m, 1H), 5.0 (m, 2H), 4.60 (m, 1H), 4.18–4.40 (m, 2H), 2.95–3.4 (m, 4H), 2.15 (s, 3H), 1.26 (s, 2H), 1.06 (s, 3H), 0.95 (s, 3H), 0.92 (s, 3H), 0.85 (s, 3H).

Mass spectrum: m/e=492.27044±6.53 ppr.

EXAMPLE 184

7(R)-N-benzhydryl-2-[8-oxo-7-(3-m-tolyl-ureido)-6,7-dihydro-8H-5-oxa-9-aza-benzocyclohepten-9-yl]-acetamide

MP=137° C.

¹H NMR (CDCl₃) δ6.7–7.6 (m, 19H), 6.30 (d, 1H), 6.18 (d, 1H), 4.85–5.0 (m, 2H), 4.58 (m, 1H), 4.30 (m, 1H), 4.0 (m, 1H), 2.22 (s, 3H).

Mass spectrum: m/e=535 (P+1).

EXAMPLE 185

7(R)-1-{9-[2-(3,3-Dimethylpiperidin-1-yl)-2-oxo-ethyl]-8-oxo-6,7,8,9-tetrahydro-5-oxa-9-aza-benzocyclohepten-7-yl}-3-m-ethylphenyl-urea

MP=107° C.

¹H NMR (CDCl₃) δ7.42 (m, 1H), 6.92–7.28 (m, 7H), 6.8 (d, 1H), 6.45 (m, 1H), 4.8–5.18 (m, 2H), 4.68 (m, 1H), 4.1–4.43 (m, 2H), 2.9–3.7 (m, 4H), 2.50 (q, 2H), 1.28–1.65 (m, 4H), 1.13 (t, 3H), 0.8–1.05 (s,s,s, 6H).

Mass spectrum: m/e=479 (P+1).

EXAMPLE 186

7(R)-1-{9-[2-(7-Aza-spiro[4,5]dec-7-yl)-2-oxo-ethyl]-8-oxo-6,7,8,9-tetrahydro-5-oxa-9-aza-benzocyclohepten-7-yl}-3-m-methylphenyl-urea

MP=115° C.

¹H NMR (CDCl₃) δ7.45 (s, 1H), 6.92–7.35 (m, 7H), 6.75 (d, 1H), 6.45 (m, 1H), 4.82–5.1 (m, 2H), 4.70 (m, 1H), 4.05–4.45 (m, 2H), 2.9–3.45 (m, 4H), 2.50 (t, 2H), 1.0–1.7 (m, 15H).

Mass spectrum: m/e=505 (P+1).

EXAMPLE 187

7(R)-1-(3-Dimethylamino-phenyl)-3-{8-oxo-9-[2-oxo-2-(3,3-dimethyl-piperidin-1-yl)-ethyl-6,7,8,9-tetrahydro-5-oxa-9-aza-benzocyclohepten-7-yl-urea ¹H NMR (CDCl₃) δ6.93–7.3 (m, 6H), 6.85 (s, 1H), 6.5 (d, 1H), 6.42 (d, 1H), 6.33 (m, 1H), 4.85–5.15 (m, 2H), 4.72 (m, 1H), 4.15–4.45 (m, 2H), 2.8–3.6 (m, 4H), 2.90 (s, 6H), 1.15–1.7 (m, 4H), 0.8–1.05 (s,s,s, 6H).

EXAMPLE 188

7(R)-2-[8-Oxo-7-(3-m-tolyl-ureido)-6,7-dihydro-8H-5-oxa-9-aza-benzocyclohepten-9-yl]-N-thiochroman-4-yl-acetamide ¹H NMR (CDCl₃) δ6.65–7.75 (m, 14H), 5.05 (m, 1H), 4.90 (m, 1H), 4.76 (d, 1H), 4.50 (m, 1H), 4.22 (m, 1H), 4.08, 3.80 (m, 1H), 2.6–3.0 (m, 3H), 2.23 (s, 3H), 2.0 (m, 1H).

Mass spectrum: m/e=517 (P+1).

EXAMPLE 189

7(R)-1-{9-2-(3,3-Dimethylpiperidin-1-yl)-2-oxo-ethyl]-8-oxo-6,7,8,9-tetrahydro -5-oxa-9-aza-benzocyclohepten-7-yl}-3-(2-thiophen-2-yl-ethyl)-urea ¹H NMR (CDCl₃) δ7.08–7.22 (m, 4H), 7.06 (m, 1H), 6.85 (m, 1H), 6.75 (m, 1H), 6.12 (m, 1H), 5.25 (m, 1H), 4.82–5.08 (m, 2H), 4.62 (m, 1H), 4.02–4.28 (m, 2H), 6.63 (m, 1H), 3.2–3.45 (m, 4H), 2.9–3.05 (m, 3H), 1.35–1.7 (m, 4H) 0.8–1.1 (s,s,s, 6H).

Mass spectrum: m/e=485 (P+1).

EXAMPLE 190

7(R)-1-(3-Chloro-phenyl)-3-{8-oxo-9-[2-oxo-2-(3,3,5,5-tetramethyl-4-oxo-piperidiyl )-ethyl]-6,7,8,9-tetrahydro-5-oxa-8-aza-benzocyclohepten-7-yl-urea

MP=106° C.

¹H NMR (CDCl₃) δ7.55 (s, 1H), 7.4 (m, 1H), 7.15–7.3 (m, 4H), 6.9–7.1 (m, 2H), 6.85 (d, 1H), 6.6 (d, 1H), 4.95–5.2 (m, 2H), 4.60 (m, 1H), 4.75–4.9 (m, 2H), 3.80 (d, 1H), 3.50 (q, 3H), 1.30 (s, 3H), 1.22 (s, 3H), 1.15 (s, 3H), 1.10 (s, 3H).

Mass spectrum: m/e=527 (P+1).

EXAMPLE 191

7(R)-1-{9-[2-(3,3-Dimethylpiperidin-1-yl)-2-oxo-ethyl]-8-oxo-6,7,8,9-tetrahydro-5-oxa-9-aza-benzocyclohepten-7-yl}-3-p-nitrophenyl-urea

MP=112° C.

¹H NMR (CDCl₃) δ8.95 (d, 1H), 7.95 (m, 2H), 7.40 (m, 2H), 7.15 (m, 4H), 6.75 (m, 1H), 4.8–5.1 (m, 2H), 4.65 (m, 1H), 4.0–4.25 (m, 2H), 2.9–3.6 (m, 4H), 1.2–1.7 (m, 4H), 0.75–1.0 (s,s,s, 6H).

Mass spectrum: m/e=496 (P+1).

EXAMPLE 192

7(R)-1-{9-[2-(3,3-Dimethylpiperidin-1-yl)-2-oxo-ethyl]-8-oxo-6,7,8,9-tetrahydro-5-oxa-9-aza-benzocyclohepten-7-yl}-3-(1(R)-naphthalen-1-yl-ethyl)-urea

MP=151° C.

¹H NMR (CDCl₃) δ8.20 (d, 1H), 7.85 (d, 1H), 7.75 (d, 1H), 7.35–7.6 (m, 4H), 7.05–7.2 (m, 4H), 6.28 (m, 1H), 5.95 (m, 1H), 5.65 (m, 1H), 5.05 (m, 1H), 4.45–4.7 (m, 2H), 3.95–4.3 (m, 2H), 2.75–3.5 (m, 4H), 1.58 (d, 3H), 1.2–1.6 (m, 4H), 0.7–0.95 (s,s,s,s, 6H).

Mass spectrum: m/e=529 (P+1).

EXAMPLE 193

7(R)-1-{9-[2-(3,3-Dimethylpiperidin-1-yl)-2-oxo-ethyl]-2-methyl-8-oxo-6,7, 8,9-tetrahydro-5-oxa-9-aza-benzocyclohepten-7-yl}-3-m-tolyl-urea

MP=165° C.

$^1$H NMR (CDCl$_3$) δ7.45 (d, 2H), 7.18 (s, 1H), 6.92–7.10 (m, 5H), 6.74 (m, 1H), 6.5 (m, 1H), 4.88–5.1 (m, 2H), 4.62 (m, 1H0, 4.2–4.4 (m, 2H), 3.55–3.8 (m, 1H), 2.95–3.4 (m, 3H), 2.35 (s, 3H), 2.2 (s, 3H), 1.3–1.7 (m, 4H), 0.8–1.1 (s,s,s, 6H).

Mass spectrum: m/e=479 (P+1).

EXAMPLE 194

7(R)-1-{9-[2-(3,3,5,5-Tetramethyl-4-oxo-piperidin-1-yl)-2-oxo-ethyl]-2-methyl-8-oxo-6,7,8,9-tetrahydro-5-oxa-9-aza-benzocyclohepten-7-yl}-3-m-tolyl-urea

MP=167° C.

$^1$H NMR (CDCl$_3$) δ6.9–7.2 (m, 7H), 6.75 (d, 1H), 6.40 (d, 1H), 4.95–5.1 (m, 2H), 4.63 (m, 1H), 4.2–4.5 (m, 2H), 3.4–3.85 (m, 4H), 2.32 (s, 3H), 2.18 (s, 3H), 1.28 (s, 3H), 1.18 (s, 3H), 1.12 (s, 3H), 1.10 (s, 3H).

Mass spectrum: m/e=521 (P+1).

EXAMPLE 195

7(R)-1-{9-[2-(3,3-Dimethylpiperidin-1-yl)-2-oxo-ethyl]-8-oxo-6,7,8,9-tetrahydro-5-oxa-9-aza-benzocyclohepten-7yl}-3-o-(trifluoromethyl)-phenyl-urea $^1$H NMR (CDCl$_3$) δ7.76 (m, 1H), 7.48 (d, 1H), 7.38 (m, 1H), 7.0–7.2 (m, 5H), 6.92 (s, 1H), 6.24 (d, 1H), 4.8–5.1 (m, 2H), 4.68 (m, 1H), 4.0–4.3 (m, 2H), 3.0–3.6 (m, 4H), 1.25–1.7 (m, 4H), 0.8–1.0 (s,s,s,s, 6H).

Mass spectrum: m/e=519 (P+1).

EXAMPLE 196

7(R)-1-{9-[2-(3,3-Dimethylpiperidin-1-yl)-2-oxo-ethyl]-8-oxo-6,7,8,9-tetrahydro-5-oxa-9aza-oxa-9-aza-benzocyclohepten-7-yl}-3-o-nitrophenyl-urea $^1$H NMR (CDCl$_3$) δ8.48 (d, 1H), 8.16 (d, 1H), 7.60 (m, 1H), 7.0–7.2 (m, 7H), 5.05 (m, 1H), 4.40 (m, 1H), 3.0–4.1 (m, 7H), 1.4–1.8 (m, 4H), 0.8–1.0 (s,s,s,s, 6H).

EXAMPLE 197

7(R)-1-{9-[2-(3,3-Dimethylpiperidin-1-yl)-2-oxo-ethyl]-8-oxo-6,7,8,9-tetrahydro-5-oxa-9-aza-benzocyclohepten-7-yl}-3-o-methoxyphenyl-urea $^1$H NMR (CDCl$_3$) δ7.88 (d, 1H), 6.7–7.2 (m, 8H), 5.95 (m, 1H), 4.8–5.0 (m, 2H), 4.73 (m, 1H), 4.0–4.3 (m, 2H), 3.76 (s, 3H), 3.45 (m, 1H), 3.1–3.35 (m, 2H), 3,0 (s, 1H), 1.2–1.6 (m, 4H), 0.8–1.0 (s,s,s,s, 6H).

Mass spectrum: m/e=481 (P+1).

EXAMPLE 198

7(R)-1-{9-[2-(3,3-Dimethylpiperidin-1-yl)-2-oxo-ethyl]-8-oxo-6,7,8,9-tetrahydro-5-oxa-9-aza-benzocyclohepten-7-yl}-3-o-isopropylphenyl-urea $^1$H NMR (CDCl$_3$) δ7.12–7.42 (m, 8H), 6.38 (bs, 1H), 5.85 (m, 1H), 4.62–5.08 (m, 3H), 4.08–4.38 (m, 2H), 2.95–3.7 (m, 5H), 1.35–1.85 (m, 4H), 1.20 (m, 6H), 0.8–1.0 (s,s,s,s, 6H).

Mass spectrum: m/e=493 (P+1).

EXAMPLE 199

7(R)-2-(3-{9-[2-(3,3-Dimethylpiperdin-1-yl)-2-oxo-ethyl]-8-oxo-6,7,8,9-tetrahydro-5-oxa-9-aza-benzocyclohepten-7-yl}-ureido)-benzoic acid methyl ester MP=126° C. $^1$H NMR (CDCl$_3$) δ8.38 (d, 1H), 7.95 (d, 1H), 7.45 (m, 1H), 7.1–7.3 (m, 5H), 6.95 (m, 1H), 5.85 (m, 1H), 4.9–5.1 (m, 2H), 4.78 (m, 1H), 4.05–4.35 (m, 2H), 3.90 (s, 3H), 3.18–3.6 (m, 3H), 3.10 (bs, 1H), 1.2–1.75 (m, 4H), 0.8–1.05 (s,s, s,s, 6H).

Mass spectrum: m/e=509 (P+1).

EXAMPLE 200

7(R)-2-(3-{9-[2-(3,3-Dimethylpiperidin-1-yl)-2-oxo-ethyl]-8-oxo-6,7,8,9-tetrahydro-5-oxa-9-aza-benzocyclohepten-7-yl}-ureido)-benzoic acid ethyl ester $^1$H NMR (CDCl$_3$) δ8.26 (d, 1H), 7.86 (d, 1H), 7.30 (m, 1H), 7.0–7.2 (m, 5H), 6.84 (m, 1H), 5.76 (m, 1H), 4.8–5.0 (m, 2H), 4.66 (m, 1H), 4.0–4.32 (m, 4H), 3.1–3.5 (m, 3H), 3,0 (bs, 1H), 1.0–1.6 (m, 7H), 0.8–1.0 (s,s,s,s, 6H).

Mass spectrum: m/e=523 (P+1).

EXAMPLE 201

7(R)-2-(3-{9-[2-(3,3-Dimethylpiperidin-1-yl)-2-oxo-ethyl]-6,7,8,9-tetrahydro-5-oxa-9-aza-benzocyclohepten-7-yl}-ureido)-benzoic acid-t-butyl ester $^1$H NMR (CDCl$_3$) δ8.24 (d, 1H), 7.84 (d, 1H), 7.30 (m, 1H), 7.0–7.22 (m, 5H), 6.85 (m, 1H), 5.72 (m, 1H), 4.8–5.0 (m, 2H), 4.68 (m, 1H), 4.0–4.3 (m, 2H), 3.1–3.5 (m, 3H), 3.0 (bs, 1H), 1.0–1.7 (m, 4H), 0.7–1.0 (m, 15H).

EXAMPLE 202

7(R)-1-[8-oxo-9-(2-oxo-2-{4-[4-(3-phenoxy-phenyl-but-3-enyl]-piperazyn-1-yl}-ethyl)-6,7,8,9-tetrahydro-5-oxa-9-aza-benzocyclohepten-7-yl]-3-m-tolyl-urea $^1$H NMR (CDCl$_3$) δ6.8–7.5 (m, 18H), 6.72 (d, 1H), 6.42 (d, 1H), 6.32 (d, 1H), 5.65 (m, 1H), 5.0 (m, 1H), 4.9 (d, 1H), 4.67 (m, 1H), 4.28 (m, 2H), 3.5 (m, 4H), 2.25–2.57 (m, 8H), 2.22 (s, 3H).

Mass spectrum: m/e=660.31528±5.03 ppm.

EXAMPLE 203

7(R)-(3-Dimethylamino-phenyl)-3-{8-oxo-9-[2-oxo-2-(3,3,5,5-tetramethylpiperidin-1-yl)-ethyl-6,7,8,9-tetrahydro-5-oxa-9-aza-benzocyclohepten -7-yl-urea $^1$H NMR (CDCl$_3$) δ7.08–7.3 (m, 6H), 6.86–7.08 (m, 2H), 6.35–6.65 (m, 2H), 4.9–5.1 (m, 2H), 4.62 (m, 1H), 4.17–4.35 (m, 2H), 2.9–3.35 (m, 4H), 2.82 (m, 6H), 1.25 (s, 2H), 1.05 (s, 3H), 0.98 (s, 3H), 0.95 (s, 3H), 0.91 (s, 3H).

Mass spectrum: m/e=521.29811±4.02 ppm,

EXAMPLE 204

7(R)-1-{9-[2-(3,3-Dimethylpiperidin-1-yl)-2-oxo-ethyl]-3-fluoro-8-8-oxo-6,7,8,9-tetrahydro-5-oxa-9-aza-benzocyclohepten-7yl}-3-m-tolyl-urea

MP=149° C.

$^1$H NMR (CDCl$_3$) δ7.72 (m, 1H), 7.20 (m, 2H), 7.02 (m, 2H), 6.90 (m, 2H), 6.75 (m, 1H), 6.52 (m, 1H), 5.05 (m, 1H), 4.87 (m, 1H), 4.65 (m, 1H), 4.35 (m, 1H), 4.17 (m, 1H), 3.62 (m, 1H), 2.9–3.4 (m, 3H), 2.18 (s, 3H), 1.3–1.7 (m, 4H), 0.78–1.0 (s,s,s,s, 6H).

Mass spectrum: m/e=483 (P+1).

EXAMPLE 205

7(R)-1-{9-[2-(3,3-Dimethylpiperidin-1-yl)-2-oxo-ethyl]-3-methyl-8-oxo-6,7, 8,9-tetrahydro-5-oxa-9-aza-benzocyclohepten-7-yl}-3-m-tolyl-urea
MP=146° C.
$^1$H NMR (CDCl$_3$) δ6.9–7.3 (m, 7H), 6.82 (m, 1H), 6.45 (mn, 1H), 4.85–5.1 (m, 2H), 4.65 (m, 1H), 4.1–4.4 (m, 2H), 2.9–3.7 (m, 4H), 2.32 (s, 3H), 2.2 (s, 3H), 1.32–1.82 (m, 4H), 0.8–1.0 (s,s,s, 6H).
Mass spectrum: m/e=479 (P+1).

EXAMPLE 206

7(R)-1-{9-[2-(3,3,5,5-Tetramethylpiperidin-1-yl)-2-oxo-ethyl]-3-fluoro-8-oxo-6,7,8,9-tetrahydro-5-oxa-9-aza-benzocyclohepten-7-yl}-3-m-tolyl-urea
$^1$H NMR (CDCl$_3$) δ6.8–7.2 (m, 7H), 6.72 (d, 1H), 6.22 (d, 1H), 4.86–5.0 (d, 2H), 4.48 (m, 1H), 4.0–4.3 (m, 2H), 2.9–3.3 (m, 4H), 2.18 (S, 3H), 1.26 (s, 2H), 1.02 (s, 3H), 0.92 (s, 3H), 0.90 (s, 3H), 0.88 (s, 3H).
Mass spectrum: m/e=511 (P+1).

EXAMPLE 207

7(R)-1-{9-[2-(3,3,5,5-Tetramethylpiperidin-1-yl)-2-oxo-ethyl]-2-fluoro-8-oxo-6,7,8,9-tetrahydro-5-oxa-9-aza-benzocyclohepten-7-yl}-3-m-chlorophenyl-urea
MP=129° C.
$^1$H NMR (CDCl$_3$) δ7.55 (s, 1H), 7.45 (m, 1H), 6.8–7.2 (m, 6H), 6.62 (d, 1H), 4.95–5.15 (m, 2H), 4.58 (m, 1H), 4.15–4.4 (m, 2H), 3.0–3.6 (m, 4H), 1.35 (s, 2H), 1.09 (s. 3H), 1.03 (s, 3H), 0.97, (s, 3H), 0.91 (s, 3H).
Mass spectrum: m/e=531 (P+1).

EXAMPLE 208

7(R)-(3-Dimethylamino-phenyl)-3-{2-fluoro-8-oxo-9-[2-oxo-2-(3,3,5,5-tetramethylpiperidin-1-yl)-ethyl-6,7,8,9-tetrahydro-5-oxa-9-aza-benzocyclohepten-7-yl-urea
$^1$H NMR (CDCl$_3$) δ6.95–7.2 (m, 5H), 6.78 m(m, 1H), 6.45 (m, 2H), 6.05 (d, 1H), 4.9–5.1 (m, 2H) 4.72 (m, 1H), 4.05–4.25 (m, 2H), 2.95–3.4 (m, 4H), 2.88 (s, 6H), 1.32 (s, 2H), 1.08 (s, 3H), 1.02 (s, 3H), 0.97 (s, 3H), 0.95 (s, 3H).
Mass spectrum: m/e=540 (P+1).

EXAMPLE 209

7(R)-1-{9-[2-(3,3,5,5-Tetramethylpiperidin-1-yl)-2-oxo-ethyl]-3-fluoro-8-oxo-6,7,8,9-tetrahydro-5-oxa-9-aza-benzocyclohepten-7-yl}-3-m-chlorophenyl-urea
$^1$H NMR (CDCl$_3$) δ7.54 (s, 1H), 7.36(s, 1H), 7.10 (m, 1H), 7.04 (m, 1H), 6.78–7.0 (m, 3H), 6.65 (d, 1H), 4.94–5.10 (m, 2H), 4.52 (m, 1H), 4.32 (t, 1H), 4.10 (m, 1H), 2.92 –3.52 (m, 4H), 1.30 (s, 2H), 1.06 (s, 3H), 0.96 (s, 3H), 0.91 (s, 3H), 0.87 (s, 3H).

EXAMPLE 210

7(R)-(3-Dimethylamino-phenyl)-3-{3-fluoro-8-oxo-9-[2-oxo-2-(3,3,5,5-tetramethylpiperidin-1-yl)-ethyl-6,7,8,9-tetrahydro-5-oxa-9-aza-benzocyclohepten-7-yl-urea
$^1$H NMR (CDCl$_3$) δ7.25 (m, 1H), 6.98–7.10 (m, 2H), 6.82–6.93 (m, 3H), 6.48 (d, 1H), 6.40 (d, 1H), 6.28 (d, 1H), 5.02 (m, 1H), 4.62 (d, 1H), 4.65 (m, 1H), 4.25 (t, 1H), 4.22 (d, 1H), 2.92–3.40 (m, 4H), 2.88 (s, 6H), 1.28 (s, 2H), 1.05 (s, 3H), 0.99 (s, 3H), 0.96 (s, 3H), 0.94 (s, 3H).

EXAMPLE 211

6(S),7(R)-1{9-[2-(3,3-Dimethylpiperidin-1-yl)-2-oxo-ethyl]-6-methyl-8-oxo-6,7,8,9-tetrahydro-5-oxa-9-aza-benzocyclohepten-7-yl}-3-m-tolyl-urea
$^1$H NMR (CDCl$_3$) δ7.45 (m, 1H), 7.05–7.25 (m, 4H), 6.9–7.05 (m, 3H), 6.72 (m, 1H), 6.62 (m, 1H), 4.8–5.1 (m, 3H), 4.1–4.45 (m, 1H), 2.9–3.67 (m, 4H), 2.20 (s, 3H), 1.42 (d, 3H), 1.3–1.68 (m, 4H), 0.8–1.0 (s,s,s,s, 6H).
Mass spectrum: m/e=478.25615±3.89 ppm.

EXAMPLE 212

6(S),7(R)-1-{9-[2-(3,3,5,5-Tetramethylpiperidin-1-yl)-2-oxo-ethyl]-6-methyl-8-oxo-6,7,8,9-tetrahydro-5-oxa-9-aza-benzocyclohepten-7-yl}-3-m-tolyl-urea
$^1$H NMR (CDCl$_3$) δ7.32 (s, 1H), 7.08–7.25 (m, 5H), 6.9–7.05 (m, 2H), 6.72 (d, 1H), 6.59 (m, 1H), 5.11 (m, 1H), 5.0 (d, 1H), 4.83 (m, 1H), 4.27 (d, 1H), 2.95–3.38 (m, 4H), 2.16 (s, 3H), 1.45 (d, 3H), 1.25 (s, 2H), 1.0 (s, 3H), 0.94 (s, 3H), 0.92 (s, 3H), 0.89 (s, 3H).
Mass spectrum: m/e=506.28836±1.86 ppm.

EXAMPLE 213

6(S),7(R)-1-(3-Dimethylamino-phenyl)-3-{6-methyl-8-oxo-9-[2-oxo-2-(3, 3,-dimethylpiperidin-1-yl)-ethyl-6,7,8, 9-tetrahydro-5-oxa-9-aza-benzocyclohepten-7-yl-urea
$^1$H NMR (CDCl$_3$) δ7.0–7.3 (m, 6H), 6.85 (m, 1H), 6.32–6.5 (m, 2H), 4.85–5.15 (m, 3H), 4.1–4.45 (m, 1H), 2.92–3.6 (m, 4H), 2.90 (s, 6H), 1.42 (m, 3H), 1.2–1.67 (m, 4H), 0.8–1.05 (s,s,s,s, 6H).
Mass spectrum: m/e=507.28334±2.40 ppm.

EXAMPLE 214

6(S),7(R)-1-(3-Dimethylamino-phenyl)-3-{6-methyl-8-oxo-9-[2-oxo-2-(3,3,5,5,-tetramethylpiperidin-1-yl)-ethyl-6,7,8,9-tetrahydro-5-oxa-9-aza-benzocyclohepten-7-yl-urea
$^1$H NMR (CDCl$_3$) δ7.08–7.22 (m, 5H), 7.03 (t, 1H), 6.88 (m, 1H), 6.4–6.55 (m, 3H), 4.8–5.05 (m, 3H), 4.22 (d, 1H), 2.90–3.55 (m, 4H), 2.86 (s, 6H), 1.42 (d, 3H), 1.28 (s, 2H), 1.05 (s, 3H), 0.95 (s, 3H), 0.92 (s, 3H), 0.88 (s, 3H).
Mass spectrum: m/e=531.31034±10.30 ppm.

EXAMPLE 215

6(S),7(R)-1{9-[2-(3,3-Dimethylpiperidin-1-yl)-2-oxo-ethyl]-6-methyl-8-6,7, 8,9-tetrahydro-5-oxa-9-aza-benzocyclohepten-7-yl}-3-m-chlorophenyl-urea
$^1$H NMR (CDCl$_3$) δ7.4–7.65 (m, 2H), 6.92–7.22 (m, 6H), 6.72–6.9 (m, 2H), 5.0–5.2 (m, 2H), 4.82 (m, 1H), 4.03–4.33 (m, 1H), 2.95–3.75 (m, 4H), 2.2–2.35 (m, 1H), 1.3–1.7 (m, 3H), 1.5 (d, 3H), 0.8–1.05 (s,s,s, 6H).
Mass spectrum: m/e=498.20076±5.27 ppm.

EXAMPLE 216

6(S),7(R)-1{9-[2-(3,3,5,5-Tetramethylpiperidin-1-yl)-2-oxo-ethyl]-6-methyl-8-oxo-6,7,8,9-tetrahydro-5-oxa-9-aza-benzocyclohepten-7-yl}-3-m-chlorophenyl-urea
$^1$H NMR (CDCl$_3$) δ6.72–7.55 (m, 10H), 5.02–5.15 (m, 2H), 4.75 (m, 1H), 4.18 (d, 1H), 3.38 (d, 1H), 2.95–3.18 (m, 3H), 1.47 (d, 3H), 1.30 (s, 2H), 1.08 (s, 3H), 0.99 (s, 3H), 0.95 (s, 3H), 0.89 (s, 3H).
Mass spectrum: m/e=526.23887±7.95 ppm.

EXAMPLE 217

6(S),7(R)-1-(3-Dimethylamino-phenyl)-3-{3-fluoro-6-methyl-8-oxo-9-[2-oxo -2-(3,3,5,5-tetramethylpiperidin-1-yl)-ethyl-6,7,8,9-tetrahydro-5-oxa-9-aza-benzocyclohepten-7-yl-urea $^1$H NMR (CDCl$_3$) δ7.20 (m, 1H), 7.08 (t, 1H), 6.7–7.0 (m, 4H), 6.42 (m, 2H), 4.88–5.10 (m, 3H), 4.13 (m, 1H), 2.9–3.4 (m, 4H), 2.90 (s, 6H), 1.40 (d, 3H), 1.30 (s, 2H), 1.05 (s, 3H), 0.97 (s, 3H), 0.96 (s, 3H), 0.95 (s, 3H).

EXAMPLE 218

6(S),7(R)-1{9-[2-(3,3,5,5-Tetramethylpiperidin-1-yl)-2-oxo-ethyl]-3-fluoro-6-methyl-8-oxo-6,7,8,9tetrahydro-5-oxa-9-aza-benzocyclohepten-7-yl}-3-m-tolyl-urea $^1$H NMR (CDCl$_3$) δ7.28 (m, 1H), 7.18 (m, 1H), 6.90–7.05 (m, 2H), 6.82 (m, 2H), 6.72 (d, 1H), 6.50 (d, 1H), 5.08 (t, 1H), 4.95 (d, 1H), 4.83 (t, 1H), 4.17 (d, 1H), 2.92–3.35 (m, 4H), 2.16 (s, 3H), 1.45 (d, 1H), 1.25 (s, 1H), 0.97 (s, 3H), 0.96 (s, 3H), 0.90 (s, 3H), 0.88 (s, 3H).

EXAMPLE 219

6(S),7(R)-1{9-[2-(3,3,5,5-Tetramethylpiperidin-1-yl)-2-oxo-ethyl]-3-fluoro-6-methyl-8-oxo-6,7,8,9-tetrahydro-5-oxa-9-aza-benzocyclohepten-7-yl}-3-m-chlorophenyl-urea $^1$H NMR (CDCl$_3$) δ6.65–7.5 (m, 9H), 5.15 (m, 2H), 4.75 (t, 1H), 4.10 (, 1H), 2.9–3.4 (m, 4H), 1.42 (d, 3H), 1.25 (s, 2H), 1.08 (s, 3H), 0.98 (s, 3H), 0.90 (s, 3H), 0.86 (s, 3H).

EXAMPLE 220

7(R)-3-(3-{9-[2-(3,3-Dimethylpiperidin-yl)-2-oxo-ethyl]-8-oxo-6,7,8,9-tetrahydro-5-oxa-9-aza-benzocyclohepten-7-yl}ureido)-benzoic acid To a solution of 0.316 g (0.000605M) of 7(R)-3-(3-{9-[2-(3,3-dimethylpiperidin-1-yl)-2-oxo-ethyl]-8-oxo-6,7,8,9-tetrahydro-5-oxa-9-aza-benzocyclohepten-7-yl}-ureido)-benzoic acid ethyl ester (Example 168) in 10 mL of absolute ethanol was added 104.0 mg (0.00187M) of KOH in 1.87 mL of ethanol. The reaction was heated to 40° C. for 2 hours. The solution was cooled to room temperature and the mixture made acidic with gaseous hydrogen chloride (HCl) dissolved in ethyl acetate (EtOAc). The reaction mixture was evaporated to dryness. The residue was chromatographed on silica using 80/20 methylene chloride/methanol as the elutant. Appropriate fractions were combined and evaporated to yield 200 mg of final product.

$^1$H NMR (D$_6$ DMSO) δ12.90 (s, 1H), 8.85 (s, 1H), 8.05 (s, 1H), 7.15–7.65 (m, 4H), 6.65–7.0 (m, 4H), 5.05 (m, 1H), 4.50 (m, 1H), 3.0–3.7 (m, 6H), 1.3–1.8 (m, 5H), 0.8–1.0 (s, s, s, 6H).

Mass spectrum: m/e=455 (p+1).

I claim:
1. A compound of the formula

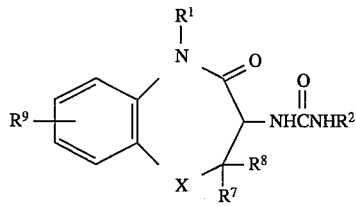

wherein

X is oxygen, sulfur, sulfoxide or sulfone;

$R^2$ is phenyl optionally substituted with one or more substituents independently selected from (C$_1$–C$_6$)alkyl, nitro, amino, (C$_1$–C$_6$)alkylamino, di-(C$_1$–C$_6$)alkylamino, halo, hydroxy, CO$_2$H, CO$_2$(C$_1$–C$_6$)alkyl, tetrazolyl, SO$_3$H, SO$_2$NH$_2$, SO$_2$NH(C$_1$–C$_6$)alkylamino, SO$_2$N-di-(C$_1$–C$_6$)alkylamino and a group of the formula

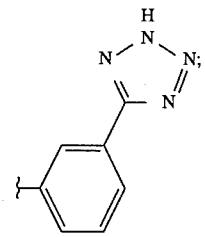

$R^3$ and $R^5$ are independently selected from (C$_1$–C$_6$)alkyl, 1-adamantyl and 2-adamantyl;

$R^4$ is hydrogen or (C$_1$–C$_6$)alkyl;

$R^6$ is a six membered saturated heterocyclic ring containing 5 carbon atoms and one nitrogen atom, wherein the nitrogen atom is the point of attachment, one of the carbon atoms may optionally be replaced by an oxygen or nitrogen atom, and one or more of said carbon atoms may optionally be substituted with one or two substituents independently selected from cyano and (C$_1$–C$_6$)alkyl;

$R^7$ is hydrogen or methyl;

$R^8$ is hydrogen or methyl; and $R^9$ is hydrogen, halo, phenyl or (C$_1$–C$_6$)alkyl;

or a pharmaceutically acceptable salt thereof.

2. A compound according to claim 1, wherein $R^6$ is selected from the group consisting of

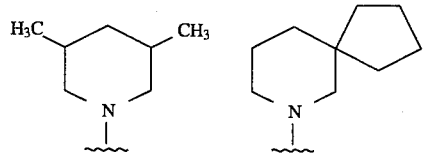

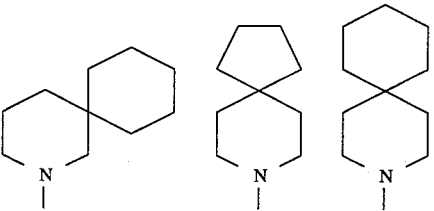

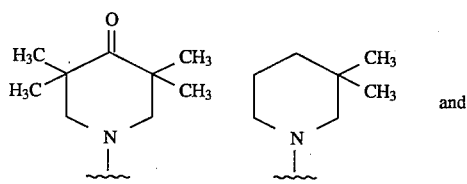

and

-continued

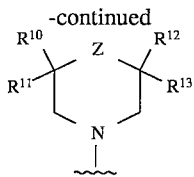

wherein Z is NH or CH$_2$ and R$^{10}$, R$^{11}$, R$^{12}$ and R$^{13}$ are independently selected from hydrogen and (C$_1$-C$_3$)alkyl.

3. A compound according to claim 1 wherein X is oxygen.

4. A compound according to claim 1, having the absolute stereochemistry depicted below

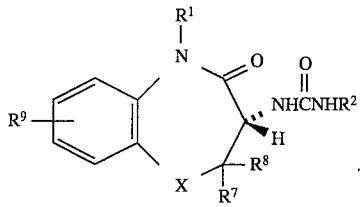

5. A compound according to claim 4, wherein X is oxygen, R$^7$ is hydrogen and R$^8$ is methyl.

6. A compound according to claim 4, wherein X is oxygen and which has the "R" stereochemical configuration at the carbon adjacent to the oxo substituent.

7. A compound according to claim 1 wherein R$^1$ is

and R$^6$ is a group of the formula

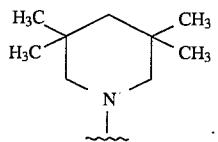

8. A compound according to claim 1, wherein said compound is selected from the group consisting of:

3(S)-1-[3,4-dihydro-4-oxo-3-[[(3-methylphenylamino)carbonyl]amino]-1,5-benzothiazepin-5(2H)-acetyl]-3,3-dimethyl piperidine;

3(S)-1-[3,4-dihydro-4-oxo-3-[[(3-methylphenylamino)carbonyl]amino]-1,5-benzothiazepin -5(2H)-acetyl]-4,4-tetramethylene piperidine;

3(S)-1-[3,4-dihydro-4-oxo-3-[[(3-methoxyphenylamino)carbonyl]amino]-1,5-benzothiazepin -5(2H)-acetyl]-3,3-dimethyl piperidine;

7(R)-1{9-[2-(3,3,5,5-tetramethylpiperidin-1-yl)-2-oxo-ethyl]-8-oxo-6,7,8,9-tetrahydro-5-oxa-9-aza-benzocyclohepten-7-yl}-3-m-chlorophenyl-urea;

7(R)-1{9-[2-(3,3,5,5-tetramethylpiperidin-1-yl)-2-oxo-ethyl]-8-oxo-6,7,8,9-tetrahydro-5-oxa-9-aza-benzocyclohepten-7-yl}-3-m-tolyl-urea;

7(R)-(3-dimethylamino-phenyl)-3-{8-oxo-9-[2-oxo-2-(3,3,5,5-tetramethylpiperidin-1-yl)-ethyl-6,7,8,9-tetrahydro-5-oxa-9-aza-benzocyclohepten-7-yl-urea;

7(R)-1-{9-[2-(3,3-dimethylpiperidin-1-yl)-2-oxo-ethyl]-3-fluoro-8-oxo-6,7, 8,9-tetrahydro-5-oxa-9-aza-benzocyclohepten-7-yl}-3-m-tolyl-urea;

7(R)-1-{9-[2-(3,3,5,5-tetramethylpiperidin-1-yl)-2-oxo-ethyl]-3-fluoro-8-oxo -6,7,8,9-tetrahydro-5-oxa-9-aza-benzocyclohepten-7-yl}-3-m-tolyl-urea;

6(S),7(R)-1{9-[2-(3,3,5,5-tetramethylpiperidin-1-yl)-2-oxo-ethyl]-6-methyl-8-oxo-6,7,8,9-tetrahydro-5-oxa-9-aza-benzocyclohepten-7-yl}-3-m-tolyl-urea;

6(S),7(R)-1-(3-dimethylamino-phenyl)-3-{6-methyl-8-oxo-9-[2-oxo-2-(3,3-dimethylpiperidin-1-yl)-ethyl-6,7,8,9-tetrahydro-5-oxa-9-aza-benzocyclohepten-7-yl-urea;

6(S),7(R)-1-(3-dimethylamino-phenyl)-3-{6-methyl-8-oxo-9-[2-oxo-2-(3,3, 5,5-tetramethylpiperidin-1-yl)-ethyl-6,7,8,9-tetrahydro-5-oxa-9-aza-benzocyclohepten-7-yl-urea;

6(S),7(R)-1{9-[2-(3,3-dimethylpiperidin-1-yl)-2-oxo-ethyl]-6-methyl-8-oxo-6,7,8,9-tetrahydro-5-oxa-9-aza-benzocyclohepten-7-yl}-3-m-chlorophenyl-urea;

6(S),7(R)-1{9-[2-(3,3,5,5-tetramethylpiperidin-1-yl)-2-oxo-ethyl]-6-methyl-8-oxo-6,7,8,9-tetrahydro-5-oxa-9-aza-benzocyclohepten-7-yl}-3-m-chlorophenyl-urea;

6(S),7(R)-1{9-[2-(3,3,5,5-tetramethylpiperidin-1-yl)-2-oxo-ethyl]-3-fluoro-6-methyl-8-oxo-6,7,8,9-tetrahydro-5-oxa-9-aza-benzocyclohepten-7-yl}-3-m-tolyl-urea; and 3(S)-1-[3,4-dihydro-4-oxo-3-[[(3-chlorophenylamino)carbonyl]amino]-1,5-benzothiazepin-5(2H)-acetyl]-3,3-dimethyl piperidine-1,1-dioxide.

9. A pharmaceutical composition for treating or preventing a condition selected from the group consisting of pain, ulcer, colitis, anxiety and panic disorder in a mammal, including a human, comprising an amount of a compound according to claim 1 effective in antagonizing the effect of cholecystokinin at its receptor cite, and a pharmaceutically acceptable carrier.

10. A method of treating or preventing a condition selected from the group consisting of pain, ulcer, colitis, anxiety and panic disorder in a mammal, including a human, comprising administering to said mammal an amount of a compound according to claim 1 effective in antagonizing the effect of cholecystokinin at its receptor site.

\* \* \* \* \*